United States Patent
Connor et al.

(10) Patent No.: US 7,544,707 B2
(45) Date of Patent: Jun. 9, 2009

(54) BICYCLIC DERIVATIVES AS PPAR MODULATORS

(75) Inventors: Scott Eugene Connor, Indianapolis, IN (US); Nathan Bryan Mantlo, Brownsburg, IN (US); Guoxin Zhu, Noblesville, IN (US); Robert Jason Herr, Voorheesville, NY (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/596,322

(22) PCT Filed: Dec. 16, 2004

(86) PCT No.: PCT/US2004/039773

§ 371 (c)(1),
(2), (4) Date: Jun. 9, 2006

(87) PCT Pub. No.: WO2005/066136

PCT Pub. Date: Jul. 21, 2005

(65) Prior Publication Data

US 2007/0106081 A1    May 10, 2007

Related U.S. Application Data

(60) Provisional application No. 60/532,139, filed on Dec. 22, 2003.

(51) Int. Cl.
*A61K 31/416* (2006.01)
*C07D 231/56* (2006.01)

(52) U.S. Cl. ............... 514/403; 514/406; 548/361.1

(58) Field of Classification Search ............ 548/361.1; 514/403, 406
See application file for complete search history.

(56) References Cited

U.S. PATENT DOCUMENTS 6,982,274 B2    1/2006   Oinuma et al.

FOREIGN PATENT DOCUMENTS

| WO | WO 97/28137 A | 8/1997 |
|---|---|---|
| WO | WO 02/10137 A | 2/2002 |
| WO | WO 02/083648 A | 10/2002 |
| WO | WO 03/084916 A | 10/2003 |
| WO | WO 2004/063155 A | 7/2004 |

OTHER PUBLICATIONS

Morissette et al. Advanced Drug Delivery Reviews 2004, 56, 275-300.*

* cited by examiner

*Primary Examiner*—Rebecca L Anderson
*Assistant Examiner*—Jason Nolan
(74) *Attorney, Agent, or Firm*—MaCharri Vorndran-Jones

(57) ABSTRACT

The present invention is directed to compounds represented by the following structural formula, Formula (I), and stereoisomers, pharmaceutically acceptable salts, solvates and hydrates thereof, wherein: (a) R2 is selected from the group consisting of $C_0$-$C_8$ alkyl and $C_{1-4}$-heteroalkyl; (b) X is selected from the group consisting of a single bond, O, S, $S(O)_2$ and N; (c) U is an aliphatic linker wherein one carbon atom of the aliphatic linker is optionally replaced with O, NH or S, and wherein such aliphatic linker is optionally substituted with from one to four substituents each independently selected from R30; (d) Y is selected from the group consisting of C, O, S, NH and a single bond; and (e) E is C(R3)(R4)A or A.

19 Claims, No Drawings

BICYCLIC DERIVATIVES AS PPAR MODULATORS

BACKGROUND OF THE INVENTION

This application is a United States national phase entry, pursuant to 35 U.S.C. 371, of PCT/US2004/039773, filed on Dec. 16, 2004, which claims the benefit of U.S. provisional patent application Ser. No. 60/532,139, filed Dec. 22, 2003, and hereby incorporated by reference in their entirety.

Information disclosed and/or claimed in this patent application has been generated pursuant to a joint research agreement among Eli Lilly and Company and Ligand Pharmaceuticals, Inc.

Peroxisome Proliferator Activated Receptors (PPARs) are members of the nuclear hormone receptor superfamily, a large and diverse group of proteins that mediate ligand-dependent transcriptional activation and repression. Three subtypes of PPARs have been isolated: PPARα, PPARγ and PPARδ.

The expression profile of each isoform differs significantly from the others, whereby PPARα is expressed primarily, but not exclusively in liver; PPARγ is expressed primarily in adipose tissue; and PPARδ is expressed ubiquitously. Studies of the individual PPAR isoforms and ligands have revealed their regulation of processes involved in insulin resistance and diabetes, as well as lipid disorders, such as hyperlipidemia and dyslipidemia. PPARγ agonists, such as pioglitazone, can be useful in the treatment of non-insulin dependent diabetes mellitus. Such PPARγ agonists are associated with insulin sensitization.

PPARα agonists, such as fenofibrate, can be useful in the treatment of hyperlipidemia. Although clinical evidence is not available to reveal the utility of PPARδ agonists in humans, several preclinical studies suggest that PPARδ agonists can be useful in the treatment of diabetes and lipid disorders.

The prevalence of the conditions that comprise Metabolic Syndrome (obesity, insulin resistance, hyperlipidemia, hypertension and atherosclerosis) continues to increase. New pharmaceutical agents are needed to address the unmet clinical needs of patients.

PPARδ agonists have been suggested as a potential treatment for use in regulating many of the parameters associated with Metabolic Syndrome and Atherosclerosis. For example, in obese, non-diabetic rhesus monkeys, a PPARδ agonist reduced circulating triglycerides and LDL, decreased basal insulin levels and increased HDL (Oliver, W. R. et al. Proc Natl Acad Sci 98:5306-5311; 2001). The insulin sensitization observed with the use of a PPARδ agonist is thought to be in part due to decreased myocellular lipids (Dressel, U. et al. Mol Endocrinol 17:2477-2493; 2003).

Further, atherosclerosis is considered to be a disease consequence of dyslipidemia and may be associated with inflammatory disease. C-reactive protein (CRP) production is part of the acute-phase response to most forms of inflammation, infection and tissue damage. It is measured diagnostically as a marker of low-grade inflammation. Plasma CRP levels of greater than 3 mg/L have been considered predictive of high risk for coronary artery disease (J. Clin. Invest 111: 1085-1812, 2003).

PPARδ agonists are believed to mediate anti-inflammatory effects. Indeed, treatment of LPS-stimulated macrophages with a PPARδ agonist has been observed to reduce the expression of iNOS, IL12, and IL-6 (Welch, J. S. et al. Proc Natl Acad Sci 100:6712-67172003).

It may be especially desirable when the active pharmaceutical agent selectively modulates a PPAR receptor subtype to provide an especially desirable pharmacological profile. In some instances, it can be desirable when the active pharmacological agent selectively modulates more than one PPAR receptor subtype to provide a desired pharmacological profile.

SUMMARY OF THE INVENTION

The present invention is directed to compounds represented by the following structural Formula I:

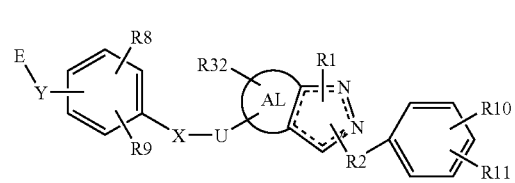

and stereoisomers, pharmaceutically acceptable salts, solvates and hydrates thereof, wherein:

(a) R1 is selected from the group consisting of hydrogen, $C_1$-$C_8$ alkyl, $C_1$-$C_8$ alkenyl, aryl-$C_{0-4}$-alkyl, aryl-$C_{1-4}$-heteroalkyl, heteroaryl-$C_{0-4}$-alkyl, C3-C6 cycloalkylaryl-$C_{0-2}$-alkyl, and, wherein $C_1$-$C_8$ alkyl, $C_1$-$C_8$ alkenyl, aryl-$C_{0-4}$-alkyl, aryl-$C_{1-4}$-heteroalkyl, heteroaryl-$C_{0-4}$-alkyl, C3-C6 cycloalkylaryl-$C_{0-2}$-alkyl are each optionally substituted with from one to three substituents independently selected from R1';

(b) R1', R26, R27, R28 and R31 are each independently selected from the group consisting of hydrogen, hydroxy, cyano, nitro, halo, oxo, $C_1$-$C_6$ alkyl, $C_1$-$C_6$ alkyl-COOR12, $C_1$-$C_6$ alkoxy, $C_1$-$C_6$haloalkyl, $C_1$-$C_6$ haloalkyloxy, $C_3$-$C_7$ cycloalkyl, aryloxy, aryl-$C_{0-4}$-alkyl, heteroaryl, heterocycloalkyl, C(O)R13, COOR14, OC(O)R15, OS(O)$_2$R16, N(R17)$_2$, NR18C(O)R19, NR20SO$_2$R21, SR22, S(O)R23, S(O)$_2$R24, and S(O)$_2$N(R25)$_2$; R12, R13, R14, R15, R16, R17, R18, R19, R20, R21, R22, R23, R24 and R25 are each independently selected from the group consisting of hydrogen, $C_1$-$C_6$ alkyl and aryl;

(c) R2 is selected from the group consisting of $C_0$-$C_8$ alkyl and $C_{1-4}$-heteroalkyl;

(d) X is selected from the group consisting of a single bond, O, S, S(O)$_2$ and N;

(e) U is an aliphatic linker wherein one carbon atom of the aliphatic linker is optionally replaced with O, NH or S, and wherein such aliphatic linker is optionally substituted with from one to four substituents each independently selected from R30;

(f) Y is selected from the group consisting of C, NH, and a single bond;

(g) E is C(R3)(R4)A or A and wherein
  (i) A is selected from the group consisting of carboxyl, tetrazole, $C_1$-$C_6$ alkylnitrile, carboxamide, sulfonamide and acylsulfonamide; wherein sulfonamide, acylsulfonamide and tetrazole are each optionally substituted with from one to two groups independently selected from $R^7$;

(ii) each $R^7$ is independently selected from the group consisting of hydrogen, $C_1$-$C_6$ haloalkyl, aryl $C_0$-$C_4$ alkyl and $C_1$-$C_6$ alkyl;

(iii) R3 is selected from the group consisting of hydrogen, $C_1$-$C_5$ alkyl, and $C_1$-$C_5$ alkoxy; and (iv) R4 is selected from the group consisting of H, $C_1$-$C_5$ alkyl, $C_1$-$C_5$ alkoxy, aryloxy, $C_3$-$C_6$ cycloalkyl, and aryl $C_0$-$C_4$ alkyl, and R3 and R4 are optionally combined to form a $C_3$-$C_4$ cycloalkyl, and wherein alkyl, alkoxy, aryloxy, cycloalkyl and aryl-alkyl are each optionally substituted with one to three substituents each independently selected from R26;

(h) R8 is selected from the group consisting of hydrogen, $C_1$-$C_4$ alkyl, $C_1$-$C_4$ alkylenyl, and halo;

(i) R9 is selected from the group consisting of hydrogen, $C_1$-$C_4$ alkyl, $C_1$-$C_4$ alkylenyl, halo, aryl-$C_0$-$C_4$ alkyl, heteroaryl, $C_1$-$C_6$ allyl, SR29, and OR29, and wherein aryl-$C_0$-$C_4$ alkyl, heteroaryl are each optionally substituted with from one to three independently selected from R27; R29 is selected from the group consisting of hydrogen, $C_1$-$C_4$ alkylenyl, and $C_1$-$C_4$ alkyl; R8 and R9 optionally combine to form a five membered fused bicyclic with the phenyl to which R8 and R9 attach, provided that when R8 and R9 form a fused ring, the group E-Y— is bonded at any available position on the five membered ring of such R8 and R9 fused bicyclic;

(j) R10, R11 are each independently selected from the group consisting of hydrogen, hydroxy, cyano, nitro, halo, oxo, $C_1$-$C_6$ alkyl, $C_1$-$C_6$ alkyl-COOR12'', $C_0$-$C_6$ alkoxy, $C_1$-$C_6$haloalkyl, $C_1$-$C_6$haloalkyloxy, $C_3$-$C_7$ cycloalkyl, aryl-$C_{0-4}$-alkyl, aryl-$C_{1-4}$-heteroalkyl, heteroaryl-$C_{0-4}$-alkyl, C3-C6 cycloalkylaryl-$C_{0-2}$-alkyl, aryloxy, C(O)R13', COOR14', OC(O)R15', OS(O)$_2$R16', N(R17')$_2$, NR18'C(O)R19', NR20'SO$_2$R21', SR22', S(O)R23', S(O)$_2$R24', and S(O)$_2$N(R25')$_2$; and wherein aryl-$C_{0-4}$-alkyl, aryl-$C_{1-4}$-heteroalkyl, heteroaryl-$C_{0-4}$-alkyl, and C3-C6 cycloalkylaryl-$C_{0-2}$-alkyl are each optionally substituted with from one to three substituents independently selected from R28;

(k) R12', R12'', R13', R14', R15', R16', R17', R18', R19', R20', R21', R22', R23', R24', and R25' are each independently selected from the group consisting of hydrogen, $C_1$-$C_6$ alkyl and aryl;

(l) R30 is selected from the group consisting of $C_1$-$C_6$ alkyl, aryl-$C_{0-4}$-alkyl, aryl-$C_{1-4}$-heteroalkyl, heteroaryl-$C_{0-4}$-alkyl, and C3-C6 cycloalkylaryl-$C_{0-2}$-alkyl, and wherein $C_1$-$C_6$ alkyl, aryl-$C_{0-4}$-alkyl, aryl-$C_{1-4}$-heteroalkyl, heteroaryl-$C_{0-4}$-alkyl, and C3-C6 cycloalkylaryl-$C_{0-2}$-alkyl are each optionally substituted with from one to three substituents each independently selected from R31;

(m) R32 is selected from the group consisting of a bond, hydrogen, halo, $C_1$-$C_6$ alkyl, $C_1$-$C_6$ haloalkyl, and $C_1$-$C_6$ alkyloxo;

(n) AL is selected from the group consisting of a fused $C_3$-$C_8$ carbocyclic, a fused pyridinyl, a fused pyrimidinyl, and a fused phenyl; and (o) - - - - is each optionally a bond to form a double bond at the indicated position.

Another embodiment of the present invention is compounds of the structural Formula II:

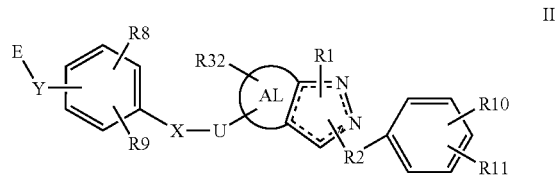

II and stereoisomers, pharmaceutically acceptable salts, solvates and hydrates thereof, wherein:

(a) R1 is selected from the group consisting of hydrogen, $C_1$-$C_8$ alkyl, $C_1$-$C_8$ alkenyl, aryl-$C_{0-4}$-alkyl, aryl-$C_{1-4}$-heteroalkyl, heteroaryl-$C_{0-4}$-alkyl, C3-C6 cycloalkylaryl-$C_{0-2}$-alkyl, and, wherein $C_1$-$C_8$ alkyl, $C_1$-$C_8$ alkenyl, aryl-$C_{0-4}$-alkyl, aryl-$C_{1-4}$-heteroalkyl, heteroaryl-$C_{0-4}$-alkyl, C3-C6 cycloalkylaryl-$C_{0-2}$-alkyl are each optionally substituted with from one to three substituents independently selected from R1';

(b) R1', R26, R27, R28 and R31 are each independently selected from the group consisting of hydrogen, hydroxy, cyano, nitro, halo, oxo, $C_1$-$C_6$ alkyl, $C_1$-$C_6$ alkyl-COOR12, $C_1$-$C_6$ alkoxy, $C_1$-$C_6$haloalkyl, $C_1$-$C_6$ haloalkyloxy, $C_3$-$C_7$ cycloalkyl, aryloxy, aryl-$C_{0-4}$-alkyl, heteroaryl, heterocycloalkyl, C(O)R13, COOR14, OC(O)R15, OS(O)$_2$R16, N(R17)$_2$, NR18C(O)R19, NR20SO$_2$R21, SR22, S(O)R23, S(O)$_2$R24, and S(O)$_2$N(R25)$_2$; R12, R13, R14, R15, R16, R17, R18, R19, R20, R21, R22, R23, R24 and R25 are each independently selected from the group consisting of hydrogen, $C_1$-$C_6$ alkyl and aryl;

(c) R2 is selected from the group consisting of $C_0$-$C_8$ alkyl and $C_{1-4}$-heteroalkyl;

(d) X is selected from the group consisting of a single bond, O, S, S(O)$_2$ and N;

(a) U is an aliphatic linker wherein one carbon atom of the aliphatic linker is optionally replaced with O, NH or S, and wherein such aliphatic linker is substituted with from one to four substituents each independently selected from R30;

(e) Y is selected from the group consisting of C, O, S, NH and a single bond;

(f) E is C(R3)(R4)A or A and wherein (i) A is selected from the group consisting of carboxyl, tetrazole, $C_1$-$C_6$ alkylnitrile, carboxamide, sulfonamide and acylsulfonamide; wherein sulfonamide, acylsulfonamide and tetrazole are each optionally substituted with from one to two groups independently selected from $R^7$;

(ii) each $R^7$ is independently selected from the group consisting of hydrogen, $C_1$-$C_6$ haloalkyl, aryl $C_0$-$C_4$ alkyl and $C_1$-$C_6$ alkyl;

(iii) R3 is selected from the group consisting of hydrogen, $C_1$-$C_5$ alkyl, and $C_1$-$C_5$ alkoxy; and (iv) R4 is selected from the group consisting of H, $C_1$-$C_5$ alkyl, $C_1$-$C_5$ alkoxy, aryloxy, $C_3$-$C_6$ cycloalkyl, and aryl $C_0$-$C_4$ alkyl, and R3 and R4 are optionally combined to form a $C_3$-$C_4$ cycloalkyl, and wherein alkyl, alkoxy, aryloxy, cycloalkyl and aryl-alkyl are each optionally substituted with one to three substituents each independently selected from R26;

(g) R8 is selected from the group consisting of hydrogen, $C_1$-$C_4$ alkyl, $C_1$-$C_4$ alkylenyl, and halo;

(h) R9 is selected from the group consisting of hydrogen, $C_1$-$C_4$ alkyl, $C_1$-$C_4$ alkylenyl, halo, aryl-$C_0$-$C_4$ alkyl, heteroaryl, $C_1$-$C_6$ allyl, SR29, and OR29, and wherein aryl-$C_0$-$C_4$ alkyl, heteroaryl are each optionally substituted with from one to three independently selected from R27; R29 is selected from the group consisting of hydrogen, $C_1$-$C_4$ alkylenyl, and $C_1$-$C_4$ alkyl; R8 and R9 optionally combine to form a five membered fused bicyclic with the phenyl to which R8 and R9 attach, provided that when R8 and R9 form a fused ring, the group E-Y— is bonded at any available position on the five membered ring of such R8 and R9 fused bicyclic;

(i) R10, R11 are each independently selected from the group consisting of hydrogen, hydroxy, cyano, nitro, halo, oxo, $C_1$-$C_6$ alkyl, $C_1$-$C_6$ alkyl-COOR12", $C_0$-$C_6$ alkoxy, $C_1$-$C_6$haloalkyl, $C_1$-$C_6$haloalkyloxy, $C_3$-$C_7$ cycloalkyl, aryl-$C_{0-4}$-alkyl, aryl-$C_{1-4}$-heteroalkyl, heteroaryl-$C_{0-4}$-alkyl, C3-C6 cycloalkylaryl-$C_{0-2}$-alkyl, aryloxy, C(O)R13', COOR14', OC(O)R15', OS(O)$_2$R16', N(R17')$_2$, NR18'C(O)R19', NR20'SO$_2$R21', SR22', S(O)R23', S(O)$_2$R24', and S(O)$_2$N(R25')$_2$; and wherein aryl-$C_{0-4}$-alkyl, aryl-$C_{1-4}$-heteroalkyl, heteroaryl-$C_{0-4}$-alkyl, and C3-C6 cycloalkylaryl-$C_{0-2}$-alkyl are each optionally substituted with from one to three substituents independently selected from R28;

(j) R12', R12", R13', R14', R15', R16', R17', R18', R19', R20', R21', R22', R23', R24', and R25' are each independently selected from the group consisting of hydrogen, $C_1$-$C_6$ alkyl and aryl;

(k) R30 is selected from the group consisting of $C_1$-$C_6$ alkyl, aryl-$C_{0-4}$-alkyl, aryl-$C_{1-4}$-heteroalkyl, heteroaryl-$C_{0-4}$-alkyl, and C3-C6 cycloalkylaryl-$C_{0-2}$-alkyl, and wherein $C_1$-$C_6$ alkyl, aryl-$C_{0-4}$-alkyl, aryl-$C_{1-4}$-heteroalkyl, heteroaryl-$C_{0-4}$-alkyl, and C3-C6 cycloalkylaryl-$C_{0-2}$-alkyl are each optionally substituted with from one to three substituents each independently selected from R31;

(l) R32 is selected from the group consisting of a bond, hydrogen, halo, $C_1$-$C_6$ alkyl, $C_1$-$C_6$haloalkyl, and $C_1$-$C_6$ alkyloxo;

(m) AL is selected from the group consisting of a fused $C_3$-$C_8$ carbocyclic, a fused pyridinyl, a fused pyrimidinyl, and a fused phenyl; and (n) - - - is each optionally a bond to form a double bond at the indicated position.

A further embodiment of the present invention is compounds of the structural Formula III:

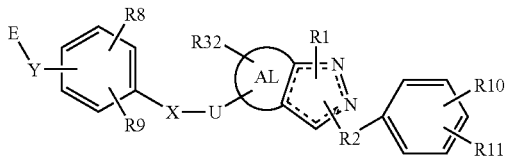

III and stereoisomers, pharmaceutically acceptable salts, solvates and hydrates thereof, wherein:

(a) R1 is selected from the group consisting of hydrogen, $C_1$-$C_8$ alkyl, $C_1$-$C_8$ alkenyl, aryl-$C_{0-4}$-alkyl, aryl-$C_{1-4}$-heteroalkyl, heteroaryl-$C_{0-4}$-alkyl, C3-C6 cycloalkylaryl-$C_{0-2}$-alkyl, and, wherein $C_1$-$C_8$ alkyl, $C_1$-$C_8$ alkenyl, aryl-$C_{0-4}$-alkyl, aryl-$C_{1-4}$-heteroalkyl, heteroaryl-$C_{0-4}$-alkyl, C3-C6 cycloalkylaryl-$C_{0-2}$-alkyl are each optionally substituted with from one to three substituents independently selected from R1';

(b) R1', R26, R27, R28 and R31 are each independently selected from the group consisting of hydrogen, hydroxy, cyano, nitro, halo, oxo, $C_1$-$C_6$ alkyl, $C_1$-$C_6$ alkyl-COOR12, $C_1$-$C_6$ alkoxy, $C_1$-$C_6$ haloalkyl, $C_1$-$C_6$ haloalkyloxy, $C_3$-$C_7$ cycloalkyl, aryloxy, aryl-$C_{0-4}$-alkyl, heteroaryl, heterocycloalkyl, C(O)R13, COOR14, OC(O)R15, OS(O)$_2$R16, N(R17)$_2$, NR18C(O)R19, NR2OSO$_2$R21, SR22, S(O)R23, S(O)$_2$R24, and S(O)$_2$N(R25)$_2$; R12, R13, R14, R15, R16, R17, R18, R19, R20, R21, R22, R23, R24 and R25 are each independently selected from the group consisting of hydrogen, $C_1$-$C_6$ alkyl and aryl;

(c) R2 is selected from the group consisting of $C_0$-$C_8$ alkyl and $C_{1-4}$-heteroalkyl;

(d) X is selected from the group consisting of a single bond; O, S, S(O)$_2$ and N;

(e) U is an aliphatic linker wherein one carbon atom of the aliphatic linker is optionally replaced with O, NH or S, and wherein such aliphatic linker is optionally substituted with from one to four substituents each independently selected from R30;

(f) Y is selected from the group consisting of C, O, S, NH and a single bond;

(g) E is C(R3)(R4)A or A and wherein
  (i) A is selected from the group consisting of carboxyl, tetrazole, $C_1$-$C_6$ alkylnitrile, carboxamide, sulfonamide and acylsulfonamide; wherein sulfonamide, acylsulfonamide and tetrazole are each optionally substituted with from one to two groups independently selected from $R^7$;
  (ii) each $R^7$ is independently selected from the group consisting of hydrogen, $C_1$-$C_6$ haloalkyl, aryl $C_0$-$C_4$ alkyl and $C_1$-$C_6$ alkyl;
  (iii) R3 is selected from the group consisting of hydrogen, $C_1$-$C_5$ alkyl, and $C_1$-$C_5$ alkoxy; and
  (iv) R4 is selected from the group consisting of H, $C_1$-$C_5$ alkyl, $C_1$-$C_5$ alkoxy, aryloxy, $C_3$-$C_6$ cycloalkyl, and aryl $C_0$-$C_4$ alkyl, and R3 and R4 are optionally combined to form a $C_3$-$C_4$ cycloalkyl, and wherein alkyl, alkoxy, aryloxy, cycloalkyl and aryl-alkyl are each optionally substituted with one to three substituents each independently selected from R26;
    with the proviso that when Y is O then R4 is selected from the group consisting of $C_1$-$C_5$ alkyl, $C_1$-$C_5$ alkoxy, aryloxy, $C_3$-$C_6$ cycloalkyl, and aryl $C_0$-$C_4$ alkyl, and R3 and R4 are optionally combined to form a $C_3$-$C_4$ cycloalkyl, and wherein alkyl, alkoxy, cycloalkyl and aryl-alkyl are each optionally substituted with one to three each independently selected from R26;

(h) R8 is selected from the group consisting of hydrogen, $C_1$-$C_4$ alkyl, $C_1$-$C_4$ alkylenyl, and halo;

(i) R9 is selected from the group consisting of hydrogen, $C_1$-$C_4$ alkyl, $C_1$-$C_4$ alkylenyl, halo, aryl-$C_0$-$C_4$ alkyl, heteroaryl, $C_1$-$C_6$ allyl, SR29, and OR29, and wherein aryl-$C_0$-$C_4$ alkyl, heteroaryl are each optionally substituted with from one to three independently selected from R27; R29 is selected from the group consisting of hydrogen, $C_1$-$C_4$ alkylenyl, and $C_1$-$C_4$ alkyl; R8 and R9 optionally combine to form a five membered fused bicyclic with the phenyl to which R8 and R9 attach, provided that when R8 and R9 form a fused ring, the group E-Y— is bonded at any available position on the five membered ring of such R8 and R9 fused bicyclic;

(j) R10, R11 are each independently selected from the group consisting of hydrogen, hydroxy, cyano, nitro, halo, oxo, $C_1$-$C_6$ alkyl, $C_1$-$C_6$ alkyl-COOR12", $C_0$-$C_6$ alkoxy, $C_1$-$C_6$ haloalkyl, $C_1$-$C_6$ haloalkyloxy, $C_3$-$C_7$ cycloalkyl, aryl-$C_{0-4}$-alkyl, aryl-$C_{1-4}$-heteroalkyl, heteroaryl-$C_{0-4}$-alkyl, C3-C6 cycloalkylaryl-$C_{0-2}$-alkyl, aryloxy, C(O)R13', COOR14', OC(O)R15', OS(O)$_2$ R16', N(R17')$_2$, NR18'C(O)R19', NR20'SO$_2$R21', SR22', S(O)R23', S(O)$_2$R24', and S(O)$_2$N(R25')$_2$; and wherein aryl-$C_{0-4}$-alkyl, aryl-$C_{1-4}$-heteroalkyl, heteroaryl-$C_{0-4}$-alkyl, and C3-C6 cycloalkylaryl-$C_{0-2}$-alkyl are each optionally substituted with from one to three substituents independently selected from R28;

(k) R12', R12'', R13', R14', R15', R16', R17', R18', R19', R20', R21', R22', R23', R24', and R25' are each independently selected from the group consisting of hydrogen, $C_1$-$C_6$ alkyl and aryl;

(l) R30 is selected from the group consisting of $C_1$-$C_6$ alkyl, aryl-$C_{0-4}$-alkyl, aryl-$C_{1-4}$-heteroalkyl, heteroaryl-$C_{0-4}$-alkyl, and C3-C6 cycloalkylaryl-$C_{0-2}$-alkyl, and wherein $C_1$-$C_6$ alkyl, aryl-$C_{0-4}$-alkyl, aryl-$C_{1-4}$-heteroalkyl, heteroaryl-$C_{0-4}$-alkyl, and C3-C6 cycloalkylaryl-$C_{0-2}$-alkyl are each optionally substituted with from one to three substituents each independently selected from R31;

(m) R32 is selected from the group consisting of a bond, hydrogen, halo, $C_1$-$C_6$ alkyl, $C_1$-$C_6$ haloalkyl, and $C_1$-$C_6$ alkyloxo;

(n) AL is selected from the group consisting of a fused $C_3$-$C_8$ carbocyclic, a fused pyridinyl, a fused pyrimidinyl, and a fused phenyl; and (o) - - - is each optionally a bond to form a double bond at the indicated position.

It can be preferred that the compound of this invention is of the structural Formula IV:

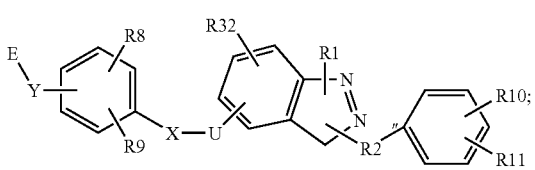

IV wherein the E, Y, R8, R9, X, U, R1, R32, R2, R10, and R11 are as defined herein above.

It can be preferred that the compound of this invention is of the structural Formula V:

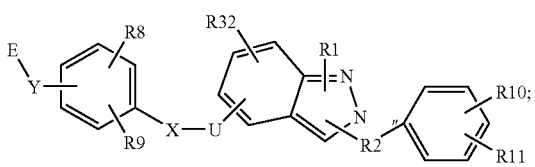

V wherein the E, Y, R8, R9, X, U, R1, R32, R2, R10, and R11 are as defined above.

It can be preferred that the compound of this invention is of the Structural Formula VI:

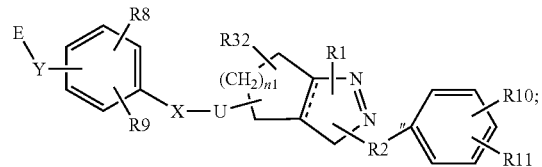

VI wherein E, Y, R8, R9, X, U, R1, R32, R'2, R10, and R11 are as defined herein above; n1 is 1 to 5. It is preferred that n1 is 1 to 2.

It can be preferred that the compound of this invention is of the Structural Formula VII:

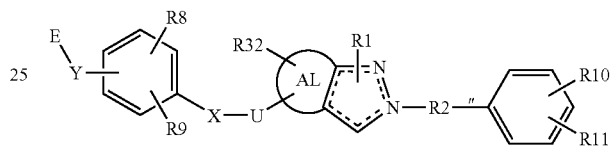

VII

In one embodiment, the present invention also relates to pharmaceutical compositions comprising at least one compound of the present invention, or a pharmaceutically acceptable salt, solvate, hydrate, or stereoisomer thereof, and a pharmaceutically acceptable carrier.

In another embodiment, the present invention relates to a method of selectively modulating a PPAR delta receptor by contacting the receptor with at least one compound represented by Structural Formula I,II, or a pharmaceutically acceptable salt, solvate, hydrate, or stereoisomer thereof.

In another embodiment, the present invention relates to a method of modulating one or more of the PPAR alpha, beta, gamma, and/or delta receptors.

In a further embodiment, the present invention relates to a method of making a compound represented by Structural Formula I, II, or III.

The compounds of the present invention are believed to be effective in treating and preventing Metabolic Syndrome, Type II diabetes, hyperglycemia, hyperlipidemia, obesity, coagaulopathy, hypertension, atherosclerosis, and other disorders related to Metabolic Syndrome and cardiovascular diseases. Further, compounds of this invention can be useful for lowering fibrinogen, increasing HDL levels, treating renal disease, controlling desirable weight, treating demyelinating diseases, treating certain viral infections, and treating liver disease. In addition, the compounds can be associated with fewer clinical side effects than compounds currently used to treat such conditions.

DETAILED DESCRIPTION OF THE INVENTION

The terms used to describe the instant invention have the following meanings.

As used herein, the term "aliphatic linker" or "aliphatic group" is a non-aromatic, consisting solely of carbon and hydrogen and may optionally contain one or more units of saturation, e.g., double and/or triple bonds (also refer herein as "alkenyl" and "alkynyl"). An aliphatic or aliphatic group may be straight chained, branched (also refer herein as "alkyl") or cyclic (also refer herein as "cycloalkyl). When straight chained or branched, an aliphatic group typically contains between about 1 and about 10 carbon atoms, more typically between about 1 and about 6 carbon atoms. When cyclic, an aliphatic typically contains between about 3 and about 10 carbon atoms, more typically between about 3 and about 7 carbon atoms. Aliphatics are preferably $C_1$-$C_{10}$ straight chained or branched alkyl groups (i.e. completely saturated aliphatic groups), more preferably $C_1$-$C_6$ straight chained or branched alkyl groups. Examples include, but are not limited to methyl, ethyl, propyl, n-propyl, iso-propyl, n-butyl, sec-butyl, and tert-butyl. Additional examples include, but are not limited to, cyclopropyl, cyclopentyl, cyclohexyl, cyclopentyl, cyclohexylyl and the like. It may be preferred that one carbon of the aliphatic linker is replaced with a N, O, or S. It may be preferred that the aliphatic linker is substituted with from one to four substituents each independently selected from R30. It may be preferred that aliphatic linker is substituted with from two to three substituents each independently selected from R30.

The term "alkyl," unless otherwise indicated, refers to those alkyl groups of a designated number of carbon atoms of either a straight or branched saturated configuration. As used herein, "$C_0$ alkyl" means that there is no carbon and therefore represents a bond. Examples of "alkyl" include, but are not limited to, methyl, ethyl, n-propyl, isopropyl, n-butyl, isobutyl, sec-butyl and tert-butyl, pentyl, hexyl, isopentyl and the like. Alkyl as defined above may be optionally substituted with a designated number of substituents as set forth in the embodiment recited above. As used herein, the term "alkyloxo" means an alkyl group of the designated number of carbon atoms with a "=O" substituent.

The term "alkenyl" or "alkylenyl" means hydrocarbon chain of a specified number of carbon atoms of either a straight or branched configuration and having at least one carbon-carbon double bond, which may occur at any point along the chain, such as ethenyl, propenyl, butenyl, pentenyl, vinyl, alkyl, 2-butenyl and the like. Alkenyl as defined above may be optionally substituted with designated number of substituents as set forth in the embodiment recited above.

The term "alkynl" means hydrocarbon chain of a specified number of carbon atoms of either a straight or branched configuration and having at least one carbon-carbon triple bond, which may occur at any point along the chain. Example of alkynyl is acetylene. Alkynyl as defined above may be optionally substituted with designated number of substituents as set forth in the embodiment recited above.

The term "heteroalkyl" refers to a means hydrocarbon chain of a specified number of carbon atoms wherein at least one carbon is replaced by a heteroatom selected from the group consisting of O, N and S.

The term "cycloalkyl" refers to a saturated or partially saturated carbocycle containing one or more rings of from 3 to 12 carbon atoms, typically 3 to 7 carbon atoms. Examples of cycloalkyl includes, but are not limited to cyclopropyl, cyclobutyl, cyclopentyl, cyclohexyl and cycloheptyl, and the like. "Cycloalkyaryl" means that an aryl is fused with a cycloalkyl, and "Cycloalkylaryl-alkyl" means that the cycloalkylaryl is linked to the parent molecule through the alkyl. Cycloalkyl as defined above may be optionally substituted with a designated number of substituents as set forth in the embodiment recited above.

The term "halo" refers to fluoro, chloro, bromo and iodo.

The term "haloalkyl" is a $C_1$-$C_6$ alkyl group, which is substituted with one or more halo atoms selected from F, Br, Cl and I. An example of a haloalkyl group is trifluoromethyl ($CF_3$).

The term "alkoxy" represents an alkyl group of indicated number of carbon atoms attached through an oxygen bridge, such as methoxy, ethoxy, propoxy, isopropoxy, butoxy, tert-butoxy, pentoxy, and the like. Alkoxy as defined above may be optionally substituted with a designated number of substituents as set forth in the embodiment recited above.

The term "haloalkyloxy" represents a $C_1$-$C_6$ haloalkyl group attached through an oxygen bridge, such as $OCF_3$. The "haloalkyloxy" as defined above may be optionally substituted with a designated number of substituents as set forth in the embodiment recited above.

The term "aryl" includes carbocyclic aromatic ring systems (e.g. phenyl), fused polycyclic aromatic ring systems (e.g. naphthyl and anthracenyl) and aromatic ring systems fused to carbocyclic non-aromatic ring systems (e.g., 1,2,3,4-tetrahydronaphthyl). "Aryl" as defined above may be optionally substituted with a designated number of substituents as set forth in the embodiment recited above.

As used herein when "R8 and R9 optionally combine to form a five membered fused bicyclic with the phenyl to which R8 and R9 attach" means when R8 and R9 combine to form a five membered ring, the resulting fused bicyclic is a structure, for example, but not limited to, a compound of the formula X:

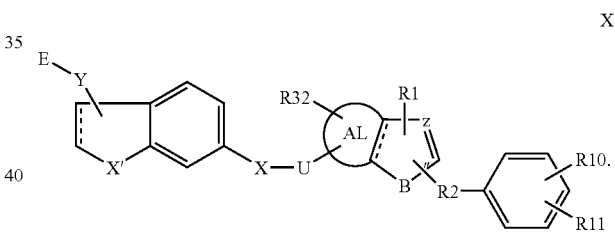

As shown by the above formula X, the variable X' is selected from the group consisting of S and O. The - - - represents an optional double bond. The fused bicyclic may contain a heteroatom at any available position on the ring and the E-Y— group shall attach at any available position on the 5 membered fused ring.

As used herein, when AL is "a fused pyrimidyl", then the pyrimidyl is fused to the five membered ring to which AL is attached. The resulting structure is, for example, but not limited to, a compound of the formula XI:

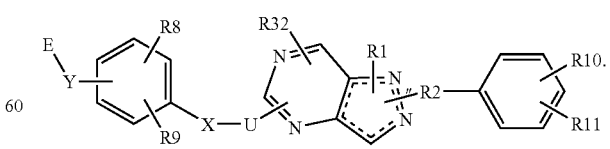

As used herein, when AL is "a fused pyridinyl", then the pyridinyl is fused to the five membered ring to which AL is attached. The resulting structure is, for example, but not limited to, a compound of the formula XII:

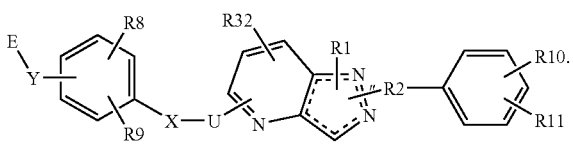

As used herein, the term "fused carbocyclic" means an optionally saturated $C_3$-$C_9$ ring system that is fused with the

group to form a 7 to 12 member bicyclic ring system. The fused ring system can optionally contain one or more double bonds. Such fused ring system is substituted with R1 and R32, as defined herein.

As used herein, the term "fused phenyl" means that the phenyl ring is fused with the

group to form a bicyclic group of the formula

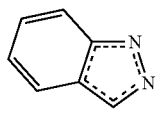

and wherein such group is substituted with R32 and R1, as defined herein.

The term "arylalkyl" refers to an aryl alkyl group which is linked to the parent molecule through the alkyl group, which may be further optionally substituted with a designated number of substituents as set forth in the embodiment recited above. When arylalkyl is arylC₀alkyl, then the aryl group is bonded directly to the parent molecule. Likewise, arylheteroalkyl means an aryl group linked to the parent molecule through the heteroalkyl group.

The term "acyl" refers to alkylcarbonyl species.

The term "heteroaryl" group, as used herein, is an aromatic ring system having at least one heteroatom such as nitrogen, sulfur or oxygen and includes monocyclic, bicyclic or tricyclic aromatic ring of 5- to 14-carbon atoms containing one or more heteroatoms selected from the group consisting of O, N, and S. The "heteroaryl" as defined above may be optionally substituted with a designated number of substituents as set forth in the embodiment recited above. Examples of heteroaryl are, but are not limited to, furanyl, indolyl, thienyl (also referred to herein as "thiophenyl") thiazolyl, imidazolyl, isoxazoyl, oxazoyl, pyrazoyl, pyrrolyl, pyrazinyl, pyridyl, pyrimidyl, pyrimidinyl and purinyl, cinnolinyl, benzofuranyl, benzothienyl, benzotriazolyl, benzoxazolyl, quinoline, isoxazolyl, isoquinoline and the like. The term "heteroarylalkyl" means that the heteroaryl group is linked to the parent molecule through the alkyl portion of the heteroarylalkyl.

The term "heterocycloalkyl" refers to a non-aromatic ring which contains one or more oxygen, nitrogen or sulfur and includes a monocyclic, bicyclic or tricyclic non-aromatic ring of 5 to 14 carbon atoms containing one or more heteroatoms selected from O, N or S. The "heterocycloalkyl" as defined above may be optionally substituted with a designated number of substituents as set forth in the embodiment recited above. Examples of heterocycloalkyl include, but are not limited to, morpholine, piperidine, piperazine, pyrrolidine, and thiomorpholine. As used herein, alkyl groups include straight chained and branched hydrocarbons, which are completely saturated.

As used herein, the phrase "selectively modulate" means a compound whose EC50 for the stated PPAR receptor is at least ten fold lower than its EC50 for the other PPAR receptor subtypes.

When a compound represented by Structural Formula I has more than one chiral substituent it may exist in diastereoisomeric forms. The diastereoisomeric pairs may be separated by methods known to those skilled in the art, for example chromatography or crystallization and the individual enantiomers within each pair may be separated using methods familiar to the skilled artisan. The present invention includes each diastereoisomer of compounds of Structural Formula I and mixtures thereof.

Certain compounds of Structural Formula I may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of Structural Formula I and mixtures thereof.

Certain compounds of Structural Formula I may exist in zwitterionic form and the present invention includes each zwitterionic form of compounds of Structural Formula I and mixtures thereof.

"Pharmaceutically-acceptable salt" refers to salts of the compounds of the Structural Formula I which are considered to be acceptable for clinical and/or veterinary use. Typical pharmaceutically-acceptable salts include those salts prepared by reaction of the compounds of the present invention with a mineral or organic acid or an organic or inorganic base. Such salts are known as acid additional salts and base addition salts, respectively. It will be recognized that the particular counterion forming a part of any salt of this invention is not of a critical nature, so long as the salt as a whole is pharmaceutically-acceptable and as long as the counterion does not contribute undesired qualities to the salt as a whole. These salts may be prepared by methods known to the skilled artisan.

The term, "active ingredient" means the compounds generically described by Structural Formula I as well as the stereoisomers, salts, solvates, and hydrates, The term "pharmaceutically acceptable" means that the carrier, diluent, excipients and salt are pharmaceutically compatible with the other ingredients of the composition. Pharmaceutical compositions of the present invention are prepared by procedures known in the art using well known and readily available ingredients.

"Preventing" refers to reducing the likelihood that the recipient will incur or develop any of the pathological conditions described herein. The term "preventing" is particularly applicable to a patient that is susceptible to the particular pathological condition.

"Treating" refers to mediating a disease or condition and preventing, or mitigating, its further progression or ameliorate the symptoms associated with the disease or condition.

"Pharmaceutically-effective amount" means that amount of active ingredient, that will elicit the biological or medical response of a tissue, system, or mammal. Such an amount can be administered prophylactically to a patient thought to be susceptible to development of a disease or condition. Such amount when administered prophylactically to a patient can also be effective to prevent or lessen the severity of the mediated condition. Such an amount is intended to include an amount which is sufficient to modulate a selected PPAR receptor or to prevent or mediate a disease or condition.

Generally, the effective amount of a Compound of Formula I will be between 0.02 through 5000 mg per day. Preferably the effective amount is between 1 through 1,500 mg per day. Preferably the dosage is from 1 through 1,000 mg per day.

The desired dose may be presented in a single dose or as divided doses administered at appropriate intervals. It may be preferred that the dosages are administered at intervals which are less than daily. For example, but not limited to, every other day, weekly, biweekly, or monthly, as appropriate.

A "mammal" is an individual animal that is a member of the taxonomic class Mammalia. The class Mammalia includes humans, monkeys, chimpanzees, gorillas, cattle, swine, horses, sheep, dogs, cats, mice, and rats.

Administration to a human is most preferred. The compounds and compositions of the present invention are useful for the treatment and/or prophylaxis of cardiovascular disease, for raising serum HDL cholesterol levels, for lowering serum triglyceride levels and for lower serum LDL cholesterol levels. Elevated triglyceride and LDL levels, and low HDL levels, are risk factors for the development of heart disease, stroke, and circulatory system disorders and diseases.

Further, the compound and compositions of the present invention may reduce the incidence of undesired cardiac events in patients. The physician of ordinary skill will know how to identify humans who will benefit from administration of the compounds and compositions of the present invention.

The compounds and compositions of the present invention are also useful for treating and/or preventing obesity.

Further, these compounds and compositions are useful for the treatment and/or prophylaxis of non-insulin dependent diabetes mellitus (NIDDM) with reduced or no body weight gains by the patients. Furthermore, the compounds and compositions of the present invention are useful to treat or prevent acute or transient disorders in insulin sensitivity, such as sometimes occur following surgery, trauma, myocardial infarction, and the like.

The present invention further provides a method for the treatment and/or prophylaxis of hyperglycemia in a human or non-human mammal which comprises administering an effective amount of active ingredient, as defined herein, to a hyperglycemic human or non-human mammal in need thereof.

The invention also relates to the use of a compound of Formula I as described above, for the manufacture of a medicament for treating a PPAR receptor mediated condition.

A therapeutically effective amount of a compound of Structural Formula I can be used for the preparation of a medicament useful for treating Metabolic Syndrome, diabetes, treating obesity, lowering tryglyceride levels, lowering serum LDL levels, raising the plasma level of high density lipoprotein, and for treating, preventing or reducing the risk of developing atherosclerosis, and for preventing or reducing the risk of having a first or subsequent atherosclerotic disease event in mammals, particularly in humans. In general, a therapeutically effective amount of a compound of the present invention typically reduces serum triglyceride levels of a patient by about 20% or more, and increases serum HDL levels in a patient. Preferably, HDL levels will be increased by about 30% or more. In addition, a therapeutically effective amount of a compound, used to prevent or treat NIDDM, typically reduces serum glucose levels, or more specifically HbA1c, of a patient by about 0.7% or more.

When used herein Metabolic Syndrome includes pre-diabetic insulin resistance syndrome and the resulting complications thereof, insulin resistance, non-insulin dependent diabetes, dyslipidemia, hyperglycemia obesity, coagulopathy, hypertension and other complications associated with diabetes. The methods and treatments mentioned herein include the above and encompass the treatment and/or prophylaxis of any one of or any combination of the following: pre-diabetic insulin resistance syndrome, the resulting complications thereof, insulin resistance, Type II or non-insulin dependent diabetes, dyslipidemia, hyperglycemia, obesity and the complications associated with diabetes including cardiovascular disease, especially atherosclerosis.

In addition, the methods and treatments mentioned herein include the above and encompass the treatment and/or prophylaxis of any one of or any combination of the following inflammatory and autoimmune diseases: adult respiratory distress syndrome, rheumatoid arthritis, demyelinating disease, Chrohne's disease, asthma, systemic lupus erythematosus, psoriasis, and bursitis.

The compositions are formulated and administered in the same general manner as detailed herein. The compounds of the instant invention may be used effectively alone or in combination with one or more additional active agents depending on the desired target therapy. Combination therapy includes administration of a single pharmaceutical dosage composition which contains a compound of Structural Formula I, a stereoisomer, salt, solvate and/or hydrate thereof ("Active Ingredient") and one or more additional active agents, as well as administration of a compound of Active Ingredient and each active agent in its own separate pharmaceutical dosage formulation. For example, an Active Ingredient and an insulin secretogogue such as biguanides, thiazolidinediones, sulfonylureas, insulin, or α-glucosidose inhibitors can be administered to the patient together in a single oral dosage composition such as a tablet or capsule, or each agent administered in separate oral dosage formulations. Where separate dosage formulations are used, an Active Ingredient and one or more additional active agents can be administered at essentially the same time, i.e., concurrently, or at separately staggered times, i.e., sequentially; combination therapy is understood to include all these regimens.

An example of combination treatment or prevention of atherosclerosis may be wherein an Active Ingredient is administered in combination with one or more of the following active agents: antihyperlipidemic agents; plasma HDL-raising agents; antihypercholesterolemic agents, fibrates, vitamins, aspirin, and the like. As noted above, the Active Ingredient can be administered in combination with more than one additional active agent.

Another example of combination therapy can be seen in treating diabetes and related disorders wherein the Active Ingredient can be effectively used in combination with, for example, sulfonylureas, biguanides, thiazolidinediones, α-glucosidase inhibitors, other insulin secretogogues, insulin as well as the active agents discussed above for treating atherosclerosis.

The Active Ingredients of the present invention, have valuable pharmacological properties and can be used in pharmaceutical compositions containing a therapeutically effective amount of Active Ingredient of the present invention, in combination with one or more pharmaceutically acceptable excipients. Excipients are inert substances such as, without limitation carriers, diluents, fillers, flavoring agents, sweeteners, lubricants, solubilizers, suspending agents, wetting agents, binders, disintegrating agents, encapsulating material and other conventional adjuvants. Proper formulation is dependent upon the route of administration chosen. Pharmaceutical compositions typically contain from about 1 to about 99 weight percent of the Active Ingredient of the present invention.

Preferably, the pharmaceutical formulation is in unit dosage form. A "unit dosage form" is a physically discrete unit containing a unit dose, suitable for administration in human subjects or other mammals. For example, a unit dosage form can be a capsule or tablet, or a number of capsules or tablets. A "unit dose" is a predetermined quantity of the Active Ingredient of the present invention, calculated to produce the desired therapeutic effect, in association with one or more pharmaceutically-acceptable excipients. The quantity of active ingredient in a unit dose may be varied or adjusted from about 0.1 to about 1500 milligrams or more according to the particular treatment involved. It may be preferred that the unit dosage is from about 1 mg to about 1000 mg.

The dosage regimen utilizing the compounds of the present invention is selected by one of ordinary skill in the medical or veterinary arts, in view of a variety of factors, including, without limitation, the species, age, weight, sex, and medical condition of the recipient, the severity of the condition to be treated, the route of administration, the level of metabolic and excretory function of the recipient, the dosage form employed, the particular compound and salt thereof employed, and the like.

Advantageously, compositions containing the compound of Structural Formula I or the salts thereof may be provided in dosage unit form, preferably each dosage unit containing from about 1 to about 500 mg be administered although it will, of course, readily be understood that the amount of the compound or compounds of Structural Formula I actually to be administered will be determined by a physician, in the light of all the relevant circumstances.

Preferably, the compounds of the present invention are administered in a single daily dose, or the total daily dose may be administered in divided doses, two, three, or more times per day. Where delivery is via transdermal forms, of course, administration is continuous.

Suitable routes of administration of pharmaceutical-compositions of the present invention include, for example, oral, eyedrop, rectal, transmucosal, topical, or intestinal administration; parenteral delivery (bolus or infusion), including intramuscular, subcutaneous, intramedullary injections, as well as intrathecal, direct intraven-tricular, intravenous, intraperitoneal, intranasal, or intraocular injections. The compounds of the invention can also be administered in a targeted drug delivery system, such as, for example, in a liposome coated with endothelial cell-specific antibody.

Solid form formulations include powders, tablets and capsules.

Sterile liquid formulations include suspensions, emulsions, syrups, and elixirs.

Pharmaceutical compositions of the present invention can be manufactured in a manner that is itself known, e.g., by means of conventional mixing, dissolving, granulating, dragee-making, levigating, emulsifying, encapsulating, entrapping, lyophilizing processes, and/or coupled with soluble polymers as targeted drug carriers.

The following pharmaceutical formulations 1 and 2 are illustrative only and are not intended to limit the scope of the invention in any way.

| Formulation 1 Hard gelatin capsules are prepared using the following ingredients: | |
|---|---|
| | Quantity (mg/capsule) |
| Active Ingredient | 250 |
| Starch, dried | 200 |
| Magnesium stearate | 10 |
| Total | 460 mg |

| Formulation 2 A tablet is prepared using the ingredients below: | |
|---|---|
| | Quantity (mg/tablet) |
| Active Ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

In yet another embodiment of the compounds of the present invention, the compound is radiolabelled, such as with carbon-14, or tritiated. Said radiolabelled or tritiated compounds are useful as reference standards for in vitro assays to identify new selective PPAR receptor agonists.

The compounds of the present invention can be useful for modulating insulin secretion and as research tools. Certain compounds and conditions within the scope of this invention are preferred. The following conditions, invention embodiments, and compound characteristics listed in tabular form may be independently combined to produce a variety of preferred compounds and process conditions. The following list of embodiments of this invention is not intended to limit the scope of this invention in any way.

Some preferred characteristics of compounds of formula I are:

(a) R3 is methyl;
(b) R4 is hydrogen;
(c) R3 is $C_1$-$C_2$ alkyl;
(d) R4 is $C_1$-$C_2$ alkyl;
(e) R3 and R4 are each hydrogen;
(f) R3 and R4 are each methyl;
(g) A is carboxyl;
(h) X is —O—;
(i) X is —S—;
(j) X is a bond;
(k) U is CH;
(l) U is $CH_2CH$;
(m) R9 is methyl;
(n) R9 is hydrogen;

(o) R9 is $C_1$-$C_3$ alkyl;
(p) R8 is methyl;
(q) R8 and R9 are each hydrogen;
(r) R8 and R9 combine to form a five membered fused ring;
(s) R8 and R9 combine to form a five membered fused ring to form a compound of the formula:

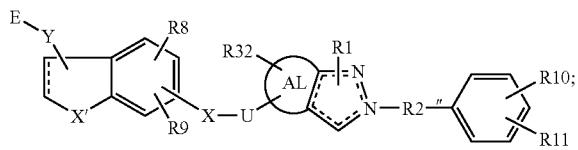

(t) X' is O;
(u) X' is S;
(v) R10 is $CF_3$;
(w) R10 is haloalkyl;
(x) R10 is haloalkyloxy;
(y) R11 is hydrogen
(z) R10 and R11 are each hydrogen;
(aa) R11 is haloalkyl;
(bb) AL is unsaturated;
(cc) AL is saturated;
(dd) AL is aromatic;
(ee) AL is a fused phenyl;
(ff) AL is fused pyriminyl;
(gg) AL is fused pyridinyl;
(hh) AL is a fused $C_5$-$C_7$ cycloalkyl;
(ii) - - - in the five membered ring each form a double bond at the designated position in Formula I;
(jj) R1 is $C_1$-$C_4$ alkyl;
(kk) R32 is hydrogen;
(ll) R2 is a bond;
(mm) R2 is $C_1$-$C_2$ alkyl;
(nn) Y is O;
(oo) Y is S;
(pp) Y is C;
(qq) E is C(R3)(R4)A;
(rr) A is COOH;
(ss) Aliphatic linker is saturated;
(tt) Aliphatic linker is substituted with $C_1$-$C_3$ alkyl;
(uu) Aliphatic linker is $C_1$-$C_3$ alkyl;
(vv) Aliphatic linker is $C_1$-$C_2$ alkyl;
(ww) Aliphatic linker is $C_1$-$C_3$ alkyl and one carbon is replaced with an —O—;
(xx) A compound of this invention of the Formula

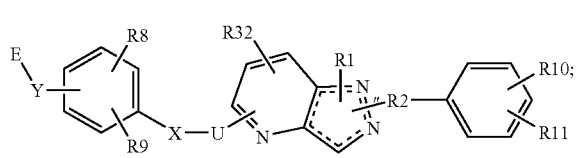

(yy) A compound of this invention of the Structural Formula:

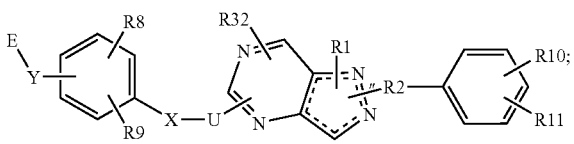

(zz) A compound of this invention of the Formula:

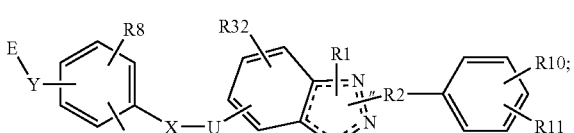

(aaa) A compound of this invention of the Formula:

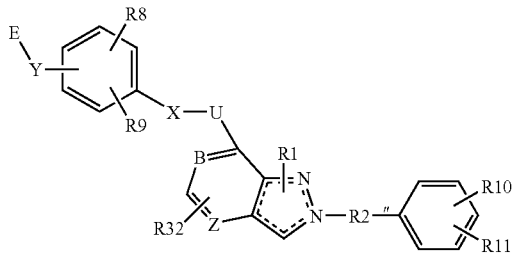

wherein B is N or C; Z is N or Z, provided that when Z is C then B is C;

(bbb) A compound of this invention of the Formula:

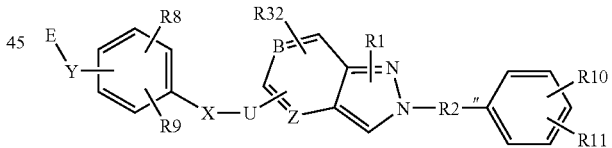

wherein B is N or C, Z is N or C, provided that when Z is C then B is C;

(ccc) A compound of this invention of the Formula:

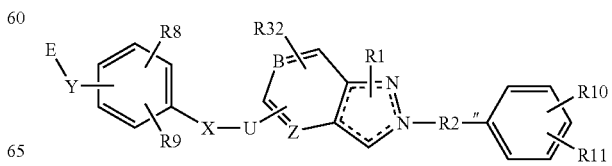

wherein B is N or C, Z is N or C, provided that when Z is C then B is C;

(ddd) A compound of this invention of the Formula:

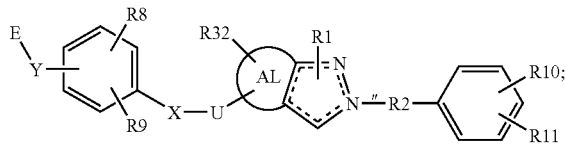

(eee) A compound of this invention of the Formula:

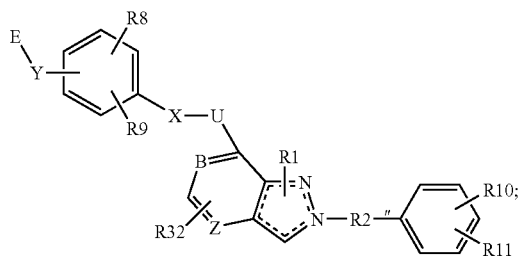

(fff) Aryl is a phenyl group;
(ggg) A compound of Formula I that selectively modulates a delta receptor;
(hhh) An Active Ingredient, as described herein, that is a PPAR coagaonist that modulates a gamma receptor and a delta receptor;
(iii) An Active Ingredient, as described herein, for use in the treatment of cardiovascular disease;
(jjj) An Active Ingredient, as described herein, for use in the treatment of Metabolic Syndrome;
(kkk) An Active Ingredient for use in the control of obesity;
(lll) An Active Ingredient for use in treating diabetes;
(mmm) An Active Ingredient that is a PPAR receptor agonist;
(nnn) A compound of Formula I selected from the group consisting of 2-Methyl-4-[2-(4-trifluoromethylphenyl)-2H-indazol-7-ylmethylsulfanyl]phenoxyacetic Acid;
3-{2-Methyl-4-[2-(4-trifluoromethylphenyl)-2H-indazol-7-ylmethylsulfanyl]phenyl}propionic Acid;
2-Ethyl-4-[2-(4-trifluoromethylphenyl)-2H-indazol-7-ylmethylsulfanyl]phenoxyacetic Acid;
3-[2-(4-Trifluoromethylphenyl)-2H-indazol-7-ylmethylsulfanyl]phenylacetic Acid;
6-[2-(4-Trifluoromethylphenyl)-2H-indazol-7-ylmethylsulfanyl]benzo[b]thiophen-3-ylacetic Acid;
3-{2-Methyl-4-[2-(4-trifluoromethylphenyl)-2H-indazol-7-ylmethoxy]phenyl}propionic Acid;
3-{2-Ethyl-4-[2-(4-trifluoromethylphenyl)-2H-indazol-7-ylmethoxy]phenyl}propionic Acid;
(+/−)-2-Methyl-4-{1-[2-(4-trifluoromethylphenyl)-2H-indazol-7-yl]ethylsulfanyl}phenoxyacetic Acid;
(+/−)-2-Methyl-4-{1-[2-(4-trifluoromethylphenyl)-2H-indazol-7-yl]ethylsulfanyl}phenoxyacetic Acid;
(+/−)-3-(2-Methyl-4-{1-[2-(4-trifluoromethylphenyl)-2H-indazol-7-yl]ethylsulfanyl}phenyl)propionic Acid;
(+/−)-2-Ethyl-4-{1-[2-(4-trifluoromethylphenyl)-2H-indazol-7-yl]ethylsulfanyl}phenoxyacetic Acid;
(+/−)-6-{1-[2-(4-Trifluoromethylphenyl)-2H-indazol-7yl]ethylsulfanyl}benzo[b]thiophen-3-ylacetic Acid;
(+/−)-3-(2-Methyl-4-{1-[2-(4-trifluoromethylphenyl)-2H-indazol-7yl]ethoxy}phenyl)propionic Acid;
(+/−)-3-(2-Ethyl-4-{1-[2-(4-trifluoromethylphenyl)-2H-indazol-7-yl]ethoxyphenyl)propionic Acid;
2-Methyl-4-{1-methyl-1-[2-(4-trifluoromethylphenyl)-2H-indazol-7-yl]ethylsulfanyl}phenoxyacetic Acid;
2-Methyl-4-{1-methyl-1-[2-(4-trifluoromethylphenyl)-2H-indazol-7-yl]ethylsulfanyl}phenoxyacetic Acid;
3-(2-Methyl-4-{1-methyl-1-[2-(4-trifluoromethylphenyl)-2H-indazol-7-yl]ethylsulfanyl}phenyl)propionic Acid;
2-Ethyl-4-{1-methyl-1-[2-(4-trifluoromethylphenyl)-2H-indazol-7-yl]ethylsulfanyl}phenoxyacetic Acid;
6-{1-Methyl-1-[2-(4-trifluoromethylphenyl)-2H-indazol-7-yl]ethylsulfanyl}benzo[b]thiophen-3-ylacetic Acid;
2-Methyl-4-[2-(4-trifluoromethylphenyl)-2H-indazol-6-ylmethylsulfanyl]phenoxyacetic Acid;
3-{2-Methyl-4-[2-(4-trifluoromethylphenyl)-2H-indazol-6-ylmethylsulfanyl]phenyl}propionic Acid;
2-Ethyl-4-[2-(4-trifluoromethylphenyl)-2H-indazol-6-ylmethylsulfanyl]phenoxyacetic Acid;
3-{2-Ethyl-4-[2-(4-trifluoromethylphenyl)-2H-indazol-6-ylmethoxy]phenyl}propionic Acid;
6-[2-(4-Trifluoromethylphenyl)-2H-indazol-6-ylmethylsulfanyl]benzo[b]thiophen-3-ylacetic Acid;
3-{2-Methyl-4-[2-(4-trifluoromethylphenyl)-2H-indazol-6-ylmethoxy]phenyl}propionic Acid;
{6-[2-(4-Trifluoromethylphenyl)-2H-indazol-6-ylmethoxy]benzo[b]thiophen-3-yl}acetic Acid;
2-Methyl-4-[2-(4-trifluoromethylphenyl)-2H-indazol-4-ylmethylsulfanyl]phenoxyacetic Acid;
2-Ethyl-4-[2-(4-trifluoromethylphenyl)-2H-indazol-4-ylmethylsulfanyl]phenoxyacetic Acid;
3-{2-Methyl-4-[2-(4-trifluoromethylphenyl)-2H-indazol-4-ylmethylsulfanyl]phenyl}propionic Acid;
6-[2-(4-Trifluoromethylphenyl)-2H-indazol-4-ylmethylsulfanyl]benzo[b]thiophen-3-ylacetic Acid;
2-Methyl-4-[1-(4-trifluoromethylphenyl)-1H-indazol-4-ylmethylsulfanyl]phenoxyacetic Acid;
2-Ethyl-4-[1-(4-trifluoromethylphenyl)-1H-indazol-4-ylmethylsulfanyl]phenoxyacetic Acid;
3-{2-Methyl-4-[1-(4-trifluoromethylphenyl)-1H-indazol-4-ylmethylsulfanyl]phenyl}propionic Acid;
3-{2-Methyl-4-[1-(4-trifluoromethylphenyl)-1H-indazol-7-ylmethylsulfanyl]phenyl}propionic Acid;
2-Methyl-4-[1-(4-trifluoromethylphenyl)-1H-indazol-7-ylmethylsulfanyl]phenoxyacetic Acid;
2-Methyl-2-{2-methyl-4-[2-(4-trifluoromethylphenyl)-2H-indazol-7-ylmethylsulfanyl]phenoxy}propionic Acid;
2-Methyl-2-{4-[2-(4-trifluoromethylphenyl)-2H-indazol-7-ylmethylsulfanyl]phenoxy}propionic Acid;
2-Methyl-2-{2-methyl-4-[2-(4-trifluoromethylphenyl)-2H-indazol-7-ylmethoxy]phenoxy}propionic Acid;
2-Methyl-2-{4-[2-(4-trifluoromethylphenyl)-2H-indazol-7-ylmethoxy]phenylsulfanyl}propionic Acid;
2-Methyl-2-{4-[2-(4-trifluoromethylphenyl)-2H-indazol-7-ylmethoxy]phenoxy}propionic Acid;
(+/−)-2-Methyl-2-(2-methyl-4-{1-[2-(4-trifluoromethylphenyl)-2H-indazol-7-yl]ethoxy}phenoxy)propionic Acid;
(+/−)-2-Methyl-2-(2-methyl-4-{1-[2-(4-trifluoromethylphenyl)-2H-indazol-7-yl]ethylsulfanyl}phenoxy)propionic Acid;
(+/−)-2-Methyl-2-(4-{1-[2-(4-trifluoromethylphenyl)-2H-indazol-7-yl]ethylsulfanyl}phenoxy)propionic Acid;
(+/−)-2-Methyl-2-(4-{1-[2-(4-trifluoromethylphenyl)-2H-indazol-7-yl]ethoxy}phenylsulfanyl)propionic Acid;
(+/−)-2-Methyl-2-(4-{1-[2-(4-trifluoromethylphenyl)-2H-indazol-7-yl]ethoxy}phenoxy)propionic Acid;

(2-Ethyl-4-{2-[2-(4-trifluoromethylphenyl)-2H-indazol-7-yl]ethylsulfanyl}phenoxy)acetic Acid;
(2-Methyl-4-{2-[2-(4-trifluoromethylphenyl)-2H-indazol-7-yl]ethylsulfanyl}phenoxy)acetic Acid;
2-Methyl-2-(4-{2-[2-(4-trifluoromethylphenyl)-2H-indazol-7-yl]ethoxy}phenoxy)propionic Acid;
2-Methyl-2-(2-methyl-4-{2-[2-(4-trifluoromethylphenyl)-2H-indazol-7-yl]ethoxy}phenoxy)propionic Acid;
2-Methyl-2-(2-methyl-4-{2-[2-(4-trifluoromethylphenyl)-2H-indazol-7-yl]ethylsulfanyl}phenoxy)propionic Acid;
2-Methyl-2-(4-{2-[2-(4-trifluoromethylphenyl)-2H-indazol-7-yl]ethylsulfanyl}phenoxy)propionic Acid;
2-Methyl-2-{2-methyl-4-[2-(4-trifluoromethylphenyl)-2H-indazol-6-ylmethoxy]phenoxy}propionic Acid;
2-Methyl-2-{4-[2-(4-trifluoromethylphenyl)-2H-indazol-6-ylmethoxy]phenoxy}propionic Acid;
2-Methyl-2-{2-methyl-4-[2-(4-trifluoromethylphenyl)-2H-indazol-6-ylmethylsulfanyl]phenoxy}propionic Acid;
2-Methyl-2-{4-[2-(4-trifluoromethylphenyl)-2H-indazol-6-ylmethylsulfanyl]phenoxy}propionic Acid;
2-Methyl-2-{4-[2-(4-trifluoromethylphenyl)-2H-indazol-6-ylmethoxy]phenylsulfanyl}propionic Acid;
2-Methyl-2-{4-[2-(4-trifluoromethylphenyl)-2H-indazol-6-ylmethoxymethyl]phenoxy}propionic Acid;
(+/−)-2-Methyl-2-(2-methyl-4-{1-[2-(4-trifluoromethylphenyl)-2H-indazol-6-yl]ethoxy}phenoxy)propionic Acid;
(+/−)-2-Methyl-2-(4-{1-[2-(4-trifluoromethylphenyl)-2H-indazol-6-yl]ethoxy}phenoxy)propionic Acid;
(+/−)-2-Methyl-2-(4-{1-[2-(4-trifluoromethylphenyl)-2H-indazol-6-yl]ethylsulfanyl}phenoxy)propionic Acid;
(+/−)-2-Methyl-2-(2-methyl-4-{1-[2-(4-trifluoromethylphenyl)-2H-indazol-6-yl]ethylsulfanyl}phenoxy)propionic Acid;
2-Methyl-2-{2-methyl-4-[2-(4-trifluoromethylphenyl)-2H-indazol-5-ylmethoxy]phenoxy}propionic Acid;
2-Methyl-2-{4-[2-(4-trifluoromethylphenyl)-2H-indazol-5-ylmethoxy]phenylsulfanyl}propionic Acid;
2-Methyl-2-{4-[2-(4-trifluoromethylphenyl)-2H-indazol-5-ylmethylsulfanyl]phenoxy}propionic Acid;
2-Methyl-2-{2-methyl-4-[2-(4-trifluoromethylphenyl)-2H-indazol-5-ylmethylsulfanyl]phenoxy}propionic Acid;
2-Methyl-2-{4-[2-(4-trifluoromethylphenyl)-2H-indazol-5-ylmethoxy]phenoxy}propionic Acid;
(+/−)-2-Methyl-2-(2-methyl-4-{1-[2-(4-trifluoromethylphenyl)-2H-indazol-5-yl]ethoxy}phenoxy)propionic Acid;
(+/−)-2-Methyl-2-(4-{1-[2-(4-trifluoromethylphenyl)-2H-indazol-5-yl]ethoxy}phenylsulfanyl)propionic Acid;
(+/−)-2-Methyl-2-(4-{1-[2-(4-trifluoromethylphenyl)-2H-indazol-5-yl]ethylsulfanyl}phenoxy)propionic Acid;
(+/−)-2-Methyl-2-(2-methyl-4-{1-[2-(4-trifluoromethylphenyl)-2H-indazol-5-yl]ethylsulfanyl}phenoxy)propionic Acid;
(+/−)-2-Methyl-2-(4-{1-[2-(4-trifluoromethylphenyl)-2H-indazol-5-yl]ethoxy}phenoxy)propionic Acid;
2-Methyl-2-{2-methyl-4-[2-(4-trifluoromethylphenyl)-2H-indazol-4-ylmethylsulfanyl]phenoxy}propionic Acid;
(+/−)-2-Methyl-2-(2-methyl-4-{1-[2-(4-trifluoromethylphenyl)-2H-indazol-4-yl]ethylsulfanyl}phenoxy)propionic Acid;
(+/−)-2-Methyl-2-(4-{1-[2-(4-trifluoromethylphenyl)-2H-indazol-4-yl]ethylsulfanyl}phenoxy)propionic Acid;
(+/−)-2-Methyl-2-(2-methyl-4-{1-[2-(4-trifluoromethylphenyl)-2H-indazol-4-yl]ethoxy}phenoxy)propionic Acid;
(+/−)-2-Methyl-2-(4-{1-[2-(4-trifluoromethylphenyl)-2H-indazol-4-yl]ethoxy}phenoxy)propionic Acid;
(+/−)-2-Methyl-2-(4-{1-[2-(4-trifluoromethyl-phenyl)-2H-indazol-4-yl]ethoxy}phenylsulfanyl)propionic Acid;
2-Methyl-2-{2-methyl-4-[1-(4-trifluoromethylphenyl)-1H-indazol-4-ylmethoxy]phenoxy}propionic Acid;
2-Methyl-2-{2-methyl-4-[1-(4-trifluoromethylphenyl)-1H-indazol-4-ylmethylsulfanyl]phenoxy}propionic Acid;
2-Methyl-2-{4-[1-(4-trifluoromethylphenyl)-1H-indazol-4-ylmethylsulfanyl]phenoxy}propionic Acid;
2-Methyl-2-{4-[1-(4-trifluoromethylphenyl)-1H-indazol-4-ylmethoxy]phenylsulfanyl}propionic Acid;
2-Methyl-2-{4-[1-(4-trifluoromethylphenyl)-1H-indazol-4-ylmethoxy]phenoxy}propionic Acid;
(+/−)-2-Methyl-2-(2-methyl-4-{1-[1-(4-trifluoromethylphenyl)-1H-indazol-4-yl]ethoxy}phenoxy)propionic Acid;
(+/−)-2-Methyl-2-(2-methyl-4-{1-[1-(4-trifluoromethylphenyl)-1H-indazol-4-yl]ethylsulfanyl}phenoxy)propionic Acid;
(+/−)-2-Methyl-2-(4-{1-[1-(4-trifluoromethylphenyl)-1H-indazol-4-yl]ethoxy}phenylsulfanyl)propionic Acid;
(+/−)-2-Methyl-2-(4-{1-[1-(4-trfluoromethylphenyl)-1H-indazol-4-yl]ethoxy}phenoxy)propionic Acid;
(+/−)-2-Methyl-2-(4-{1-[1-(4-trifluoromethylphenyl)-1H-indazol-4-yl]ethylsulfanyl}phenoxy)propionic Acid;
(+/−)-2-Methyl-2-(2-methyl-4-{4,4,4-trifluoro-1-[1-(4-trifluoromethylphenyl)-1H-indazol-4-yl]butoxy}phenoxy)propionic Acid;
(+/−)-2-Methyl-2-(2-methyl-4-{4,4,4-trifluoro-1-[1-(4-trifluoromethylphenyl)-1H-indazol-4-yl]butylsulfanyl}phenoxy)propionic Acid;
(+/−)-2-Methyl-2-(4-{4,4,4-trifluoro-1-[1-(4-trifluoromethylphenyl)-1H-indazol-4-yl]butoxy}phenylsulfanyl)propionic Acid;
(+/−)-2-Methyl-2-(4-{4,4,4-trifluoro-1-[1-(4-trifluoromethylphenyl)-1H-indazol-4-yl]butoxy}phenoxy)propionic Acid;
(+/−)-2-Methyl-2-(2-methyl-4-{phenyl-[1-(4-trifluoromethylphenyl)-1H-indazol-4-yl]methoxy}phenoxy)propionic Acid;
(+/−)-2-Methyl-2-(2-methyl-4-{phenyl-[1-(4-trifluoromethylphenyl)-1H-indazol-4-yl]methylsulfanyl}phenoxy)propionic Acid;
(+/−)-2-Methyl-2-(4-{phenyl-[1-(4-trifluoromethylphenyl)-1H-indazol-4-yl]methoxy}phenylsulfanyl)propionic Acid;
(+/−)-2-Methyl-2-(4-{phenyl-[1-(4-trifluoromethylphenyl)-1H-indazol-4-yl]methylsulfanyl}phenoxy)propionic Acid;
(+/−)-2-Methyl-2-(4-{phenyl-[1-(4-trifluoromethylphenyl)-1H-indazol-4-yl]methoxy}phenoxy)propionic Acid;
2-Methyl-2-{2-methyl-4-[1-(4-trifluoromethylphenyl)-1H-indazol-7-ylmethoxy]phenoxy}propionic Acid;
2-Methyl-2-{4-[1-(4-trifluoromethylphenyl)-1H-indazol-7-ylmethoxy]phenylsulfanyl}propionic Acid;
2-Methyl-2-{2-methyl-4-[1-(4-trifluoromethylphenyl)-1H-indazol-7-ylmethylsulfanyl]phenoxy}propionic Acid;
2-Methyl-2-{4-[1-(4-trifluoromethylphenyl)-1H-indazol-7-ylmethylsulfanyl]phenoxy}propionic Acid; and
2-Methyl-2-{4-[1-(4-trifluoromethylphenyl)-1H-indazol-7-ylmethoxy]phenoxy}propionic Acid.

Synthesis

Compounds of the present invention have been formed as specifically described in the examples. Further, many compounds are prepared as more generally using a Mitsunobu protocol (O. Mitsunobu, 1981 Synthesis, p1) and other methods known to the skilled artisan. Alternative synthesis methods may also be effective and known to the skilled artisan.

For example (Scheme I), a starting material A is alkylated with a 1H- or 2H-indazole alkylating agent B in the presence of a base (e.g. K2CO3, Cs2CO3 etc.). Hydrolysis in the presence of aqueous NaOH or LiOH gives the acid product, Formula I. where E is an intermediate ester.

Scheme I.

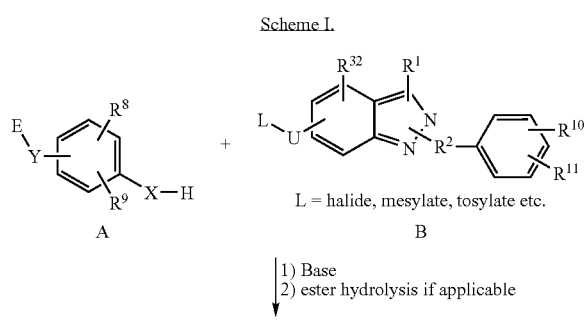

Alternatively (Scheme II.), a starting material A is coupled with an alcohol C under Mitsunobu reaction condition (DEAD/PPh3, ADDP/PBu3 etc.). Hydrolysis in the presence of aqueous NaOH or LiOH gives the acid product, Formula I. where E is an intermediate ester:

Scheme II.

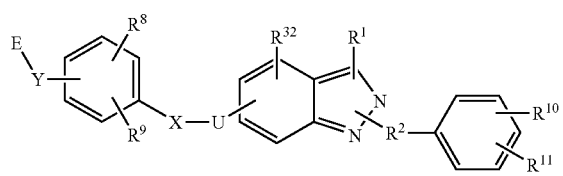

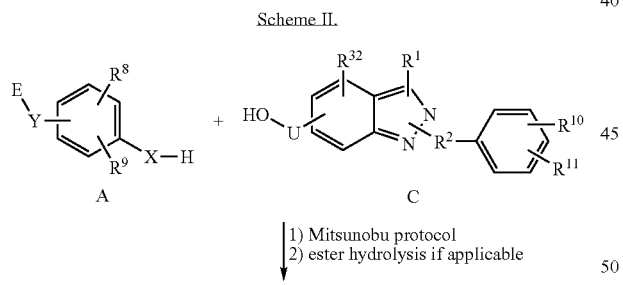

Thioether analogs of Formula I. could also be prepared by a ZnI$_2$ mediated thioether formation reaction as shown below:

Scheme III.

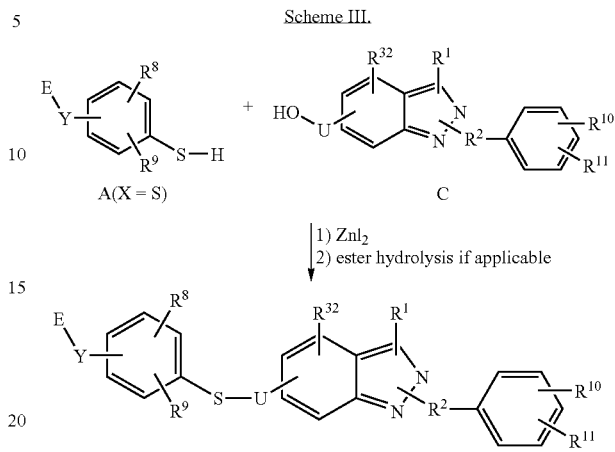

The phenol, thiophenol, and aniline starting materials A are either commercially available or known in the literature or exemplified herein.

1H-Indazole intermediates B and C are made by one of the following methods:

Scheme IV.

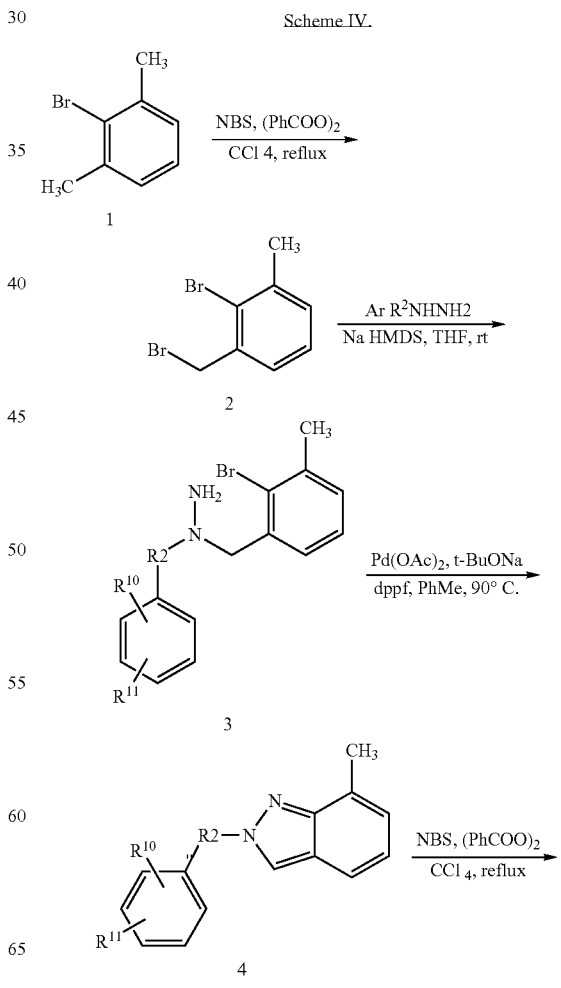

-continued

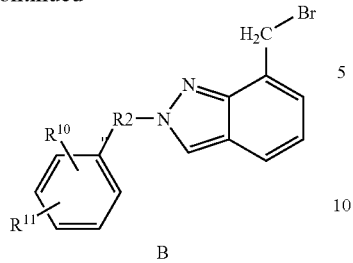

B

A commercially available or known ortho-alkyl-phenyl-bromide 1 is halogenated with NBS or NCS in a non-polar solvent, e.g., carbon tetrachloride to give an ortho-haloalkylphenyl bromide 2. The alkylhalide of Compound 2 is displaced by a hydrazine (ArR2NHNH2) in the presence of NaHMDS and THF to give the substituted hydrazine 3. Hydrazine 3 is cyclized with palladium catalysis at elevated temperature in toluene to give the 2H-indazole 4. 2H-Indazole 4 is halogenated with NBS or NCS to give the alkylhalide C.

Scheme Va.

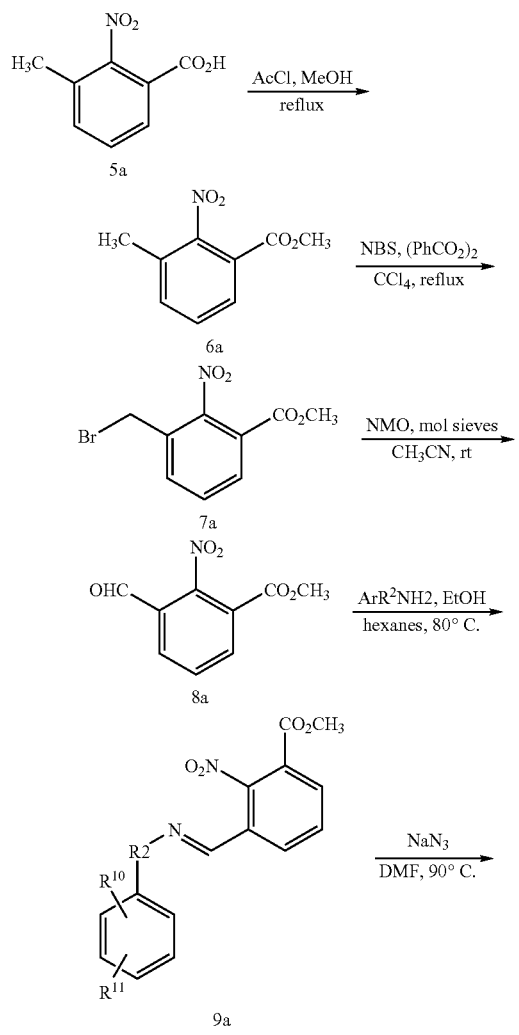

-continued

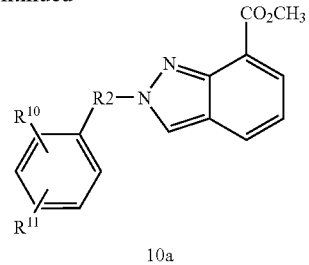

10a

An ortho-alkylnitro-benzoic acid 5a is converted to an ester 6a that is halogenated with NCS or NBS in carbon tetrachloride to an alkyl halide 7a. Oxidation of the alkyl halide to an aldehyde 8a is achieved with NMO in a polar aprotic solvent, e.g., acetonitrile. Imine formation of aldehyde 8a with an amine (ArR2NH2) at elevated temperature gives 9a. The imine 9a is treated with sodium, potassium, or lithium azide in DMF at elevated temperature to give the 2H-indazole carboxylic acid ester intermediate 10a.

Scheme Vb.

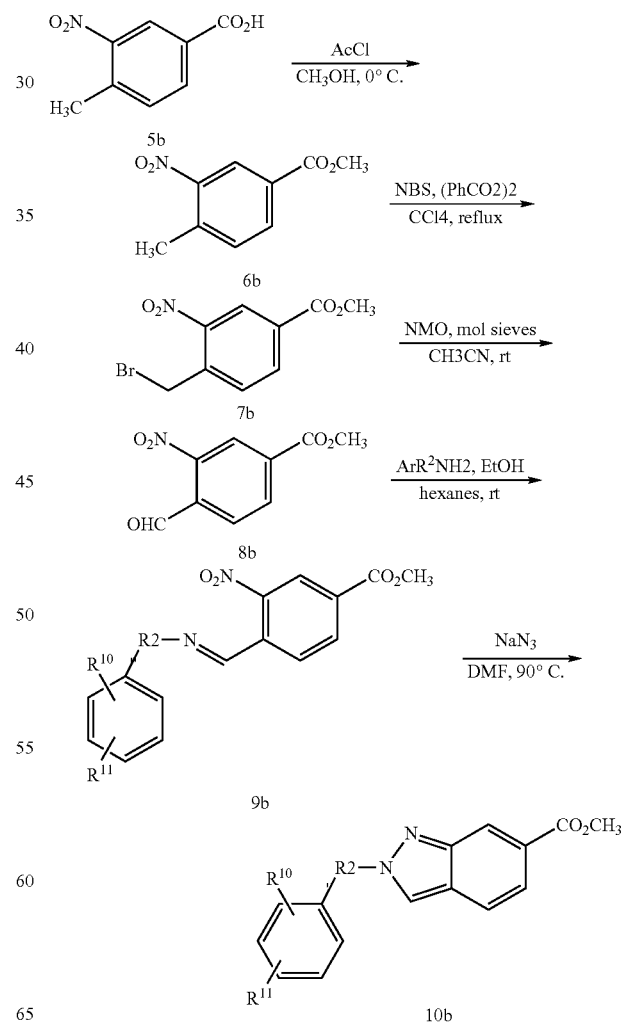

A similar sequence to Scheme Va is illustrated (Scheme Vb) for an isomeric ortho-alkylnitro-benzoic acid 5b.

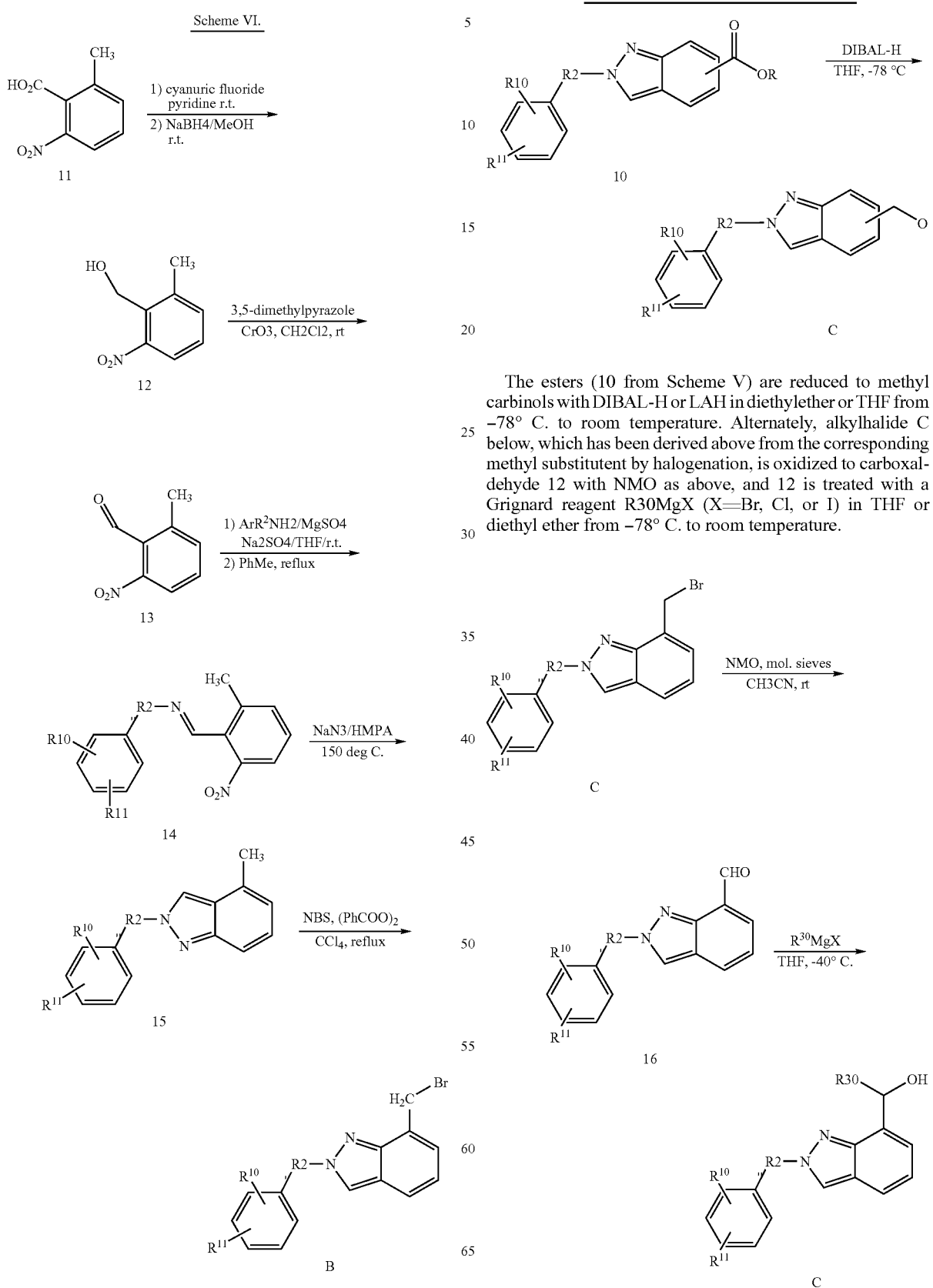

The esters (10 from Scheme V) are reduced to methyl carbinols with DIBAL-H or LAH in diethylether or THF from −78° C. to room temperature. Alternately, alkylhalide C below, which has been derived above from the corresponding methyl substitutent by halogenation, is oxidized to carboxaldehyde 12 with NMO as above, and 12 is treated with a Grignard reagent R30MgX (X=Br, Cl, or I) in THF or diethyl ether from −78° C. to room temperature.

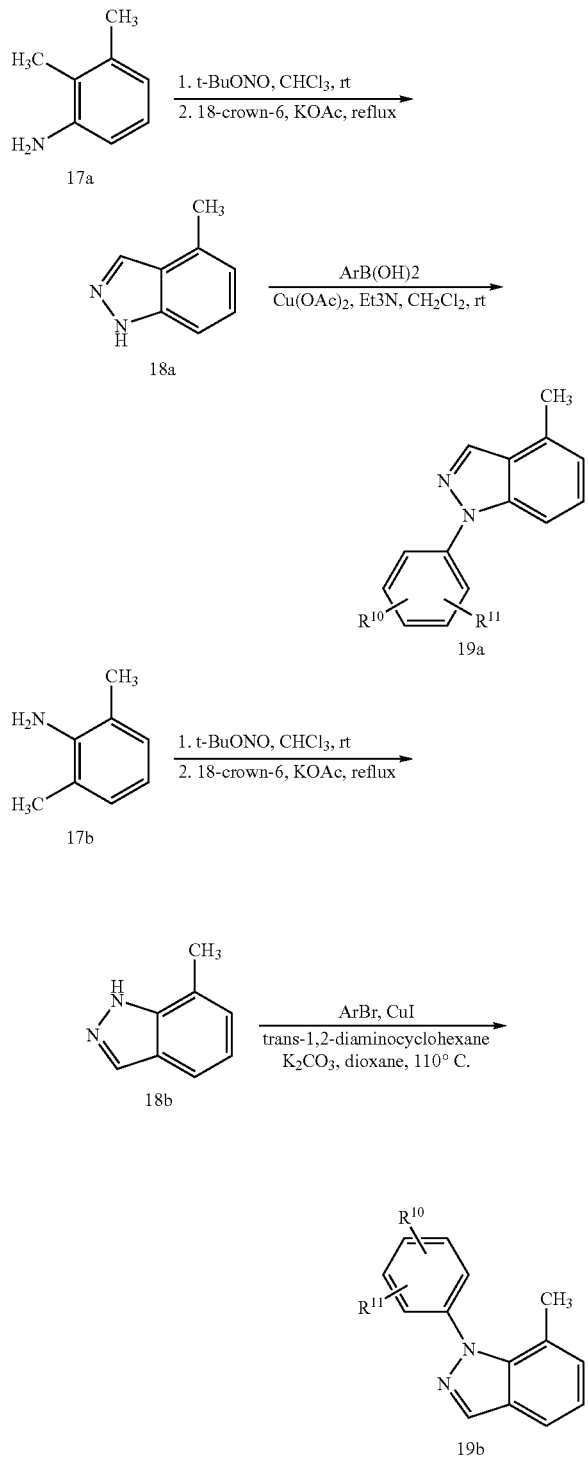

Scheme VIII.
Synthesis of 4,5,6, or 7-Methyl-1H-Indazole intermediates for 1H-Indazole B and C syntheses.

An ortho-methylaniline (17a or 17b) is nitrosated with a low molecular weight alkylnitrite, e.g., isobutylnitrite and cyclized with a base, e.g., potassium acetate to give a 1H-indazole 18. The 1H-indazole is coupled with either an arylboronic acid and cupric acetate or an aryl halide and cuprous halide to give the methyl-1H-indazoles 19, which can be converted to B with NBS or NCS as described above.

As is well known to practitioners skilled in the art of organic compound manipulations, both tetrazoles and carboxamides are easily prepared from carboxylic acid examples of Formula I.

EXEMPLIFICATION

The Examples provided herein are illustrative of the invention claimed herein and are not intended to limit the scope of the claimed invention in any way.

Instrumental Analysis

General

All non-aqueous reactions were performed under a dry atmosphere of nitrogen unless otherwise specified. Commercial grade reagents and anhydrous solvents were used as received from vendors and no attempts were made to purify or dry these components further. Removal of solvents under reduced pressure was accomplished with a Buchi rotary evaporator at approximately 28 mm Hg pressure using a Teflon-lined KNF vacuum pump. Flash column chromatography was carried out using Kieselgel silica gel 60. Proton NMR spectra were obtained on a Bruker AC 300 MHz Nuclear Magnetic Resonance Spectrometer and are reported in ppm δ values, using tetramethylsilane as an internal reference. Melting points were obtained using an Electrothermal melting point apparatus and are uncorrected. API Mass spectroscopic analyses were performed on a Finnegan LCQ Duo Ion Trap or a PESciex API 150EX mass spectrometer, using electro spray ionization (ESI) or atmospheric pressure chemical ionization (APCI). HPLC analyses were conducted using a Waters Symmetry C18, 5um, WAT046980, 3.9×150 mm column. The elution system consisted of 90:10 (0.1% TFA in H$_2$O)/(0.1% TFA in CH$_3$CN) gradient elution to 10:90 (0.1% TFA in H$_2$O)/(0.1% TFA in CH$_3$CN) over 20 min, followed by 10:90 (0.1% TFA in H$_2$O)/(0.1% TFA in CH$_3$CN) isocratic elution for 10 min, followed by 90:10 (0.1% TFA in H$_2$O)/(0.1% TFA in CH$_3$CN) isocratic elution for 10 min. The flow rate was 1 mL/min. UV Detection was performed at 254 nm.

Preparation 1

2-(4-Hydroxy-2-methyl-phenoxy)-2-methyl-propionic acid

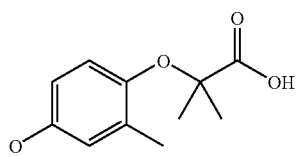

Step A 2-(4-Benzyloxy-2-formylphenoxy)-2-methyl propionic acid ethyl ester

5-Benzyloxy-2-hydroxy-benzaldehyde (Kappe, T.; Witoszynskyj, T. Arch. Pharm., 1975, 308 (5), 339-346) (2.28 g, 10.0 mmol), ethyl bromoisobutyrate (2.2 mL, 15 mmol), and cesium carbonate (3.26 g, 10.0 mmol) in dry DMF (25 mL) are heated at 80° C. for 18 h. The reaction mixture is cooled and partitioned between water (30 mL) and ether (75 mL).

The organic layer is washed with brine (15 mL). The aqueous layers are back-extracted with ethyl acetate (30 mL), and the organic layer is washed with brine (20 mL). The combined organic layers are dried ($Na_2SO_4$) and concentrated to a brown oil. The crude product is purified by flash chromatography using hexanes:ethyl acetate (2.5:1) to give a pale yellow solid (3.04 g, 89%): mp 65° C.; $^1$H NMR (400 MHz, $CDCl_3$) δ 1.24 (t, 3H, J=7.1 Hz), 1.62 (s, 6H), 4.23 (q, 2H, J=7.1 Hz), 6.81 (d, 1H, J=8.8 Hz), 7.10 (dd, 1H, J=4.6, 9.0 Hz), 7.30-7.43 (m, 6H); MS (ES) m/e 343.1 [M+1].

Step B 2-(4-Hydroxy-2-methyl-phenoxy)-2-methyl-propionic acid ethyl ester 2-(4-Benzyloxy-2-formyl-phenoxy)-2-methyl-propionic acid ethyl ester (9.00 g, 26.3 mmol) in ethanol (250 mL) is treated with 5% Pd/C (1.25 g) and hydrogen (60 psi, rt, overnight). Additional 5% Pd/C (1.25 g) is added, and the reaction is continued for 6 h at 40° C. The mixture is filtered and concentrated to a tan oil (6.25 g). This oil contained 9 mol % of 2-(4-Hydroxy-2-hydroxymethyl-phenoxy)-2-methyl-propionic acid ethyl ester.

$^1$H NMR (400 MHz, $CDCl_3$) δ 1.26 (t, 3H, J=7.3 Hz), 1.51 (s, 6H), 2.14 (s, 3H), 4.24 (q, 2H, J=7.3 Hz), 5.68 (brs, 1H), 6.47 (dd, 1H, J=3.4, 8.8 Hz), 6.59 (d, 1H, J=8.3 Hz), 6.60 (brs, 1H).

The following compound is prepared in a similar manner:

Preparation 2

2-(4-Hydroxy-2-methyl-phenoxy)-acetic acid ethyl ester

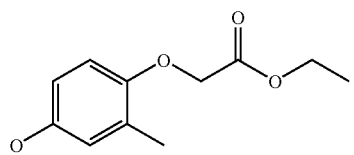

$^1$H NMR (400 MHz, CDCl3) δ 1.28 (t, 3H, J=7.1 Hz), 2.24 (s, 3H), 4.25 (q, 2H, J=7.1 Hz), 4.55 (s, 2H), 6.56 (dd, 1H, J=2.7, 8.5 Hz), 6.61 (d, 1H, J=8.3 Hz), 6.65 (d, 2H, J=2.9 Hz).

Preparation 3

(4-Hydroxy-2-propyl-phenoxy)-acetic acid ethyl ester

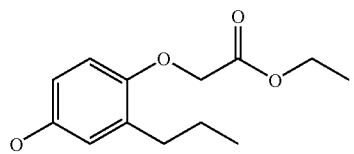

Step A

4-Benzyloxy-2-propylphenol

2-Allyl-4-benzyloxyphenol (WO 9728137 A1 19970807, Adams, A. D. et al.) (5.00 g, 20.8 mmol) in ethyl acetate (40 mL) is treated with 5% Pd/C (0.25 g) and hydrogen (1 atm) at ambient temperature for 18 h. The mixture is filtered and concentrated. The crude product is purified on a Biotage medium pressure chromatography system using a 40L normal phase cartridge and eluted with 10% ethyl acetate in hexanes to give a tan solid (2.8 g, 56%). Rf=0.33 (25% EtOAc/Hexanes); $^1$H NMR (400 MHz, $CDCl_3$) δ 7.44-7.31 (m, 5H), 6.78 (s, 1H), 6.69 (d, J=1.5 Hz, 2H), 5.00 (s, 2H), 4.31 (s, 1H), 2.55 (t, J=7.6 Hz, 2H), 1.64 (q, J=7.5 Hz, 2H), 0.97 (t, J=7.3 Hz, 3H).

Step B (4-Benzyloxy-2-propylphenoxy)acetic acid ethyl ester

A solution of 4-benzyloxy-2-propylphenol (0.50 g, 1.94 mmol) in dry DMF (7 mL) is cooled in an ice bath and treated with NaH (0.15 g, 3.8 mmol, 60% oil dispersion). The ice bath is removed, ethyl bromoacetate (0.43 mL, 3.9 mmol) is added, and the mixture is placed in an oil bath (T=85° C.). After 18 h, the reaction mixture is cooled and concentrated in vacuo. The residue is diluted with EtOAc, washed with brine (2×), dried ($Na_2SO_4$), and concentrated. The crude product is purified by radial chromatography using 10% ethyl acetate in hexanes to give a tan solid (0.62 g, 97%). $^1$H NMR (400 MHz, $CDCl_3$) δ 7.44-7.31 (m, 5H), 6.82 (d, J=2.9 Hz, 1H), 6.72 (dd, J=8.8, 2.9 Hz, 1H), 6.66 (d, J=8.8 Hz, 1H), 5.00 (s, 2H), 4.57 (s, 2H), 4.25 (q, J=7.0 Hz, 2H), 2.63 (t, J=7.6 Hz, 2H), 1.64 (q, J=7.5 Hz, 2H), 1.29 (t, J=7.1 Hz, 3H), 0.95 (t, J=7.3 Hz, 3H); MS (FIA) m/e 329 (M+1).

Step C (4-Hydroxy-2-propylphenoxy)acetic acid ethyl ester

A solution of (4-benzyloxy-2-propylphenoxy)acetic acid ethyl ester (0.60 g, 1.83 mmol) in THF (15 mL) is treated with 5% Pd/C (75 mg) and hydrogen (60 psi) at ambient temperature for 24 h. The mixture is filtered and concentrated. The crude product is purified by radial chromatography using 15% ethyl acetate in hexanes to give a tan solid (0.25 g, 57%). $^1$H NMR (400 MHz, $CDCl_3$) δ 6.66 (d, J=2.9 Hz, 1H), 6.62 (d, J=8.8 Hz, 1H), 6.57 (dd, J=8.8, 2.9 Hz, 1H), 4.56 (s, 1H), 4.40 (s, 1H), 4.25 (q, J=7.2 Hz, 2H), 2.61 (t, J=7.6 Hz, 2H), 1.63 (q, J=7.5 Hz, 2H), 1.29 (t, J=7.1 Hz, 3H), 0.95 (t, J=7.3 Hz, 3H); MS (FIA) m/e 239 (M+1).

Preparation 4

(3-Bromo-4-hydroxy-phenoxy)-acetic acid ethyl ester

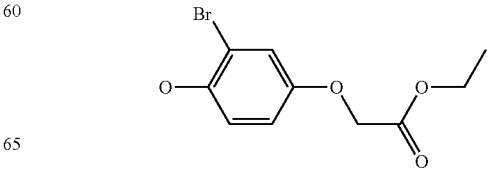

To a solution of (4-hydroxy-phenoxy)-acetic acid ethyl ester (0.59 g, 3 mmol) in acetic acid (1.5 mL) is added bromine (0.48 g, 9 mmol) in acetic acid (0.5 mL) at room temperature. After 5 min, solvent is evaporated and purified by column chromatography on silica gel giving the title compound (0.6 g).

Preparation 5

(4-Mercapto-phenoxy)-acetic acid ethyl ester

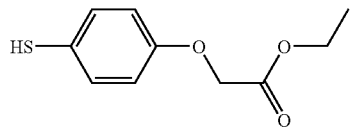

Step A (4-Chlorosulfonl-phenoxy)-acetic acid ethyl ester

Phenoxy-acetic acid ethyl ester (9.1 mL) is added to chlorosulfonic acid (15 mL) at 0° C. dropwise. The reaction is stirred at 0° C. for 30 min, it is allowed to warm to room temperature. After 2 hrs, the reaction mixture is poured into ice, solid product is collected by filtration and dried under vacuum.

Step B (4-Mercapto-phenoxy)-acetic acid ethyl ester

To a mixture of (4-chlorosulfonyl-phenoxy)-acetic acid ethyl ester (0.98 g, 3.5 mmol) and tin powder (2.1 g) in ethanol (4.4 mL) is added HCl in dioxane (1.0 M, 4.4 mL) under nitrogen. The mixture is heated to reflux for 2 hrs, it is poured into ice and methylene chloride and filtered. The layers are separated and extracted with methylene chloride, dried and concentrated. The crude product is used for next step without purification.

The following compounds are made in a similar manner:

Preparation 6

(4-Mercapto-2-propyl-phenoxy)-acetic acid ethyl ester

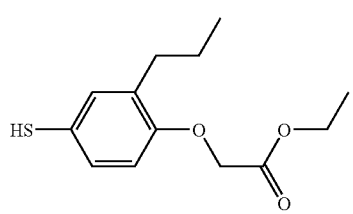

Preparation 7

(4-Mercapto-2-methyl-phenoxy)-acetic acid ethyl ester

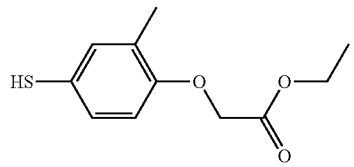

This compound can also be made by the following procedure:

To a stirred suspension of Zn powder (10 μm, 78.16 g, 1.2 mol) and dichlorodimethyl silane (154.30 g, 145.02 mL, 1.2 mol) in 500 mL of dichloroethane is added a solution of (4-chlorosulfonyl-2-methyl-phenoxy)-acetic acid ethyl ester (100 g, 0.34 mol) and 1,3-dimethylimidazolidin-2-one (116.98 g, 112.05 mL, 1.02 mol) in 1 L of DCE. Addition is at a rate so as to maintain the internal temperature at ~52° C., cooling with chilled water as necessary. After addition is complete, the mixture is heated at 75° C. for 1 hour. It is then cooled to room temperature, filtered and concentrated iv. Add MTBE, washed twice with saturated LiCl solution, concentrate iv again. Take up the residue in $CH_3CN$, wash with hexane (4×) and concentrate iv to yield a biphasic mixture. Let stand in a separatory funnel and separate layers, keeping the bottom layer for product. Filtration through a plug of silica gel (1 Kg, 25% EtOAc/hexane) and subsequent concentration yields 61 g (79%) of a clear, colorless oil.

NMR (DMSO-$d_6$) δ 7.1 (s, 1H), 7.05 (dd, 1H), 6.75 (d, 1H), 5.03 (s, 1H), 4.75 (s, 2H), 4.15 (q, 2H), 2.15 (s, 3H), 1.2 (t, 3H).

Preparation 8

3-(4-Hydroxy-2-methyl-phenyl)-propionic acid methyl ester

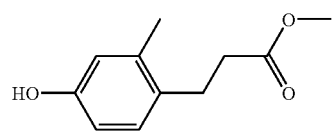

Step A

4-Bromo-3-methyl-phenyl benzyl ester

To a solution of 4-Bromo-3-methyl-phenol (20.6 g, 0.0.11 mol) in DMF (100 mL) is added Cs2CO3 (54 g, 0.165 mol), followed by benzyl bromide (14.4 mL). After stirred at 60° C. for 40 h, the reaction mixture is diluted with ethyl acetate, filtered through celite.

The filtrate is washed with water and brine, dried over sodium sulfate, concentration yields the title product (27 g).

Step B

3-(4-Benzyloxy-2-methyl-phenyl)-propionic acid methyl ester

To a solution of 4-bromo-3-methyl-phenyl benzyl ester (7.6 g, 27.4 mmol) in propronitrile (200 mL) is added methyl acrylate (10 mL) and diisopropylethyl amine (9.75 mL), the solution is degassed and filled with nitrogen for three times. To this mixture are added tri-o-tolyl-phosphane (3.36 g) and palladium acetate (1.25 g) under nitrogen, then heated at 110° C. overnight, cooled to room temperature, filtered through celite. The solvent is evaporated, the residue is taken into ethyl acetate and washed with water and brine, dried over sodium sulfate. Concentration and column chromatography on silica gel eluted with hexanes and ethyl acetate yields the title compound (6.33 g).

Step C

3-(4-Hydroxy-2-methyl-phenyl)-propionic acid methyl ester

A mixture of 3-(4-Benzyloxy-2-methyl-phenyl)-propionic acid methyl ester (13.7 g, 48.5 mmol) and Pd/C (5%, 13.7 g) in MeOH (423 mL) is stirred under 60 psi of hydrogen for 24 hrs. Catalyst is filtered off, filtrate is concentrated giving the title compound (8.8 g, 93.5%).

Preparation 9

3-(4-Mercapto-2-methyl-phenyl)-propionic acid methyl ester

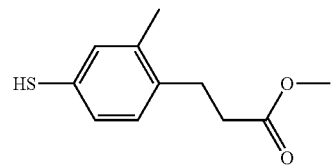

Step A

3-(4-Dimethylthiocarbamoyloxy-2-methyl-phenyl)-propionic acid methyl ester 3-(4-Hydroxy-2-methyl-phenyl)-propionic acid methyl ester (5.0 g, 25.75 mmol) is dissolved into dry dioxane (100 mL) and combined with 4-dimethylamino pyridine (0.500 g, 2.6 mmol), triethylamine (7.0 mL, 51.5 mmol), and dimethylaminothiocarbomoyl chloride (4.5 g, 32.17 mmol). The reaction is heated to reflux under nitrogen. The reaction is monitored by TLC until all of the phenol is consumed, 20 h. After cooling to room temperature, the reaction is diluted with ethyl acetate (200 mL). Water (75 mL) is added and the two layers are separated. The organic layer is washed with brine (75 mL) then dried over anhydrous sodium sulfate. The solvent is removed and the residue is dried under vacuum.

Step B

3-(4-Dimethylcarbamoylsulfanyl-2-methyl-phenyl)-propionic acid methyl ester 3-(4-Dimethylthiocarbamoyloxy-2-methyl-phenyl)-propionic acid methyl ester, taken crude from the previous step, is diluted with 75 mL of tetradecane and heated to reflux under nitrogen. The reaction is monitored by TLC until all the conversion is complete, 20 h. The reaction is allowed to cool to room temperature, then the tetradecane is decanted away from the resulting oil. The residue is rinsed several times with hexanes. This oil is then purified using flash column chromatography, yielding 5.01 g, or 69% (2 steps) of the product.

Step C

3-(4-Mercapto-2-methyl-phenyl)-propionic acid methyl ester 3-(4-Dimethylcarbamoylsulfanyl-2-methyl-phenyl)-propionic acid methyl ester (5.01 g, 17.8 mmol) is diluted with methanol (30 mL) and to this is added sodium methoxide (1.7 mL of 4M in methanol, 7.23 mmol). The reaction is heated to reflux under nitrogen and monitored by TLC. After complete conversion, 20 h., the reaction is allowed to cool to room temperature. The reaction is neutralized with 1N HCl (7.23 mL) and diluted with ethyl acetate (150 mL). The two phases are separated and the organic layer is washed with water (75 mL), then brine (75 mL). The organic layer is then dried over anhydrous sodium sulfate, then concentrated to yield 4.43 g crude product that is used without further purification.

The following compounds were made in a similar manner starting from corresponding phenol analog

Preparation 10

(3-Chloro-4-mercapto-phenyl)-acetic acid methyl ester

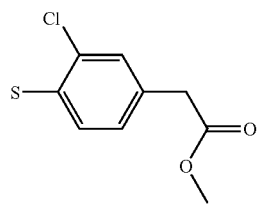

Preparation 11

3-(4-Mercapto-2-methyl-phenyl)-2,2-dimethyl-propionic acid methyl ester

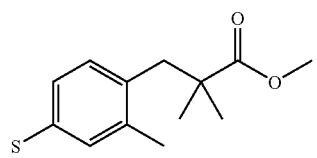

Preparation 12

(4-Hydroxy-2-methyl-phenyl)-acetic acid methyl ester

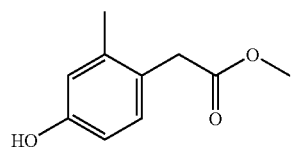

Step A

4-Methoxy-2-methylbenzoic acid (2.5 g, 15.04 mmol) is stirred in thionyl chloride (50 mL) at reflux 2 hr. The mixture is concentrated and diluted with toluene (10 mL) and concentrated. The resulting solid is dried under vacuum 18 hr. The resulting acid chloride is stirred in 20 mL ether at 0 deg C. A solution of diazomethane (39.6 mmol) in ether (150 mL) is added to the acid chloride solution and stirred 18 hr. The resulting diazoketone solution is concentrated. The residue is stirred in methanol (100 mL) and a solution of silver benzoate in triethylamine (1.0 g in 10 mL) is added and the reaction is heated to 60 deg C. and stirred 1 hr. The mixture is concentrated, diluted with 1.0 N aqueous hydrochloric acid (20 mL), extracted to three portions of ethyl acetate (50 mL each). The extracts are combined, washed with aqueous saturated sodium hydrogen carbonate, water, and brine (50 mL each), dried over anhydrous magnesium sulfate, filtered and concentrated. The residue is purified via silica gel chromatography eluting with 9:1 hexanes:ethyl acetate to afford 1.5 g (51%) of the homologated ester as a white solid.

Step B (4-Methoxy-2-methyl-phenyl)-acetic acid methyl ester (1.5 g, 7.72 mmol) is stirred in dichloromethane (50 mL) at 0 deg. C. Aluminum chloride (4.13 g, 31 mmol) is added followed by ethane thiol (2.9 mL, 38.6 mmol). The resulting mixture is stirred at room temperature for 2 hr. Water (50 mL) is added and the product is extracted into ethyl acetate (3× 50 ml), the extracts are combined, dried over anhydrous magnesium sulfate, filtered, and concentrated to afford the title compound as a colorless oil, 1.4 g, 100%. MS M$^+$+1 181. The structure is confirmed by $^1$H NMR spectroscopy.

Preparation 13

(3-Hydroxy-phenyl)-acetic acid methyl ester

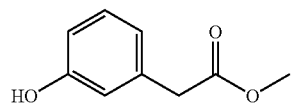

Step A (3-Hydroxy-phenyl)-acetic acid methyl ester (3-Hydroxy-phenyl)-acetic acid (5.0 g, 32.86 mmol) is stirred in methanol (100 mL) and concentrated (98%) sulfuric acid (3.0 mL,) is added. The mixture is heated to reflux 18 hr. The reaction is cooled and concentrated. The residue is diluted with water (100 mL) and extracted with ethyl acetate (3× 50 mL). The combined extracts are dried over anhydrous magnesium sulfate, filtered, and concentrated to yield the title compound as an orange oil, 5.46 g, 100%. MS M$^+$+1 167. The structure is confirmed by $^1$H NMR spectroscopy.

The following compounds are made in a similar manner:

Preparation 14

(3-Hydroxy-4-methoxy-phenyl)-acetic acid methyl ester

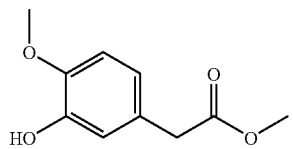

An orange oil. MS M$^+$+1 197. The structure is confirmed by $^1$H NMR spectroscopy.

Preparation 15

3-(3-Hydroxy-phenyl)-propionic acid methyl ester

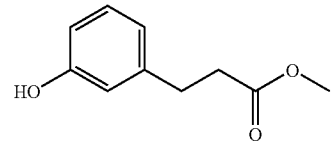

An orange oil. MS M$^+$+1 181. The structure is confirmed by $^1$H NMR spectroscopy.

Preparation 16

(3-Mercapto-phenyl)-acetic acid methyl ester

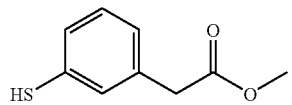

Step A (3-Dimethylthiocarbamoyloxy-phenyl)-acetic acid methyl ester

A mixture of (3-Hydroxy-phenyl)-acetic acid methyl ester (5.5 g, 33.1 mmol), N,N-dimethyl thiocarbamoyl chloride (5.11 g, 41.38 mmol), triethylamine (9.2 mL, 66.2 mmol), N,N-dimethylamino pyridine (0.4 g, 3.31 mmol) and dioxane (50 mL) is stirred at reflux 18 hr. The mixture is concentrated, partioned between 1M aqueous hydrochloric acid (200 mL) and ethyl acetate (3× 75 mL). The combined organic extracts are dried over anhydrous magnesium sulfate, filtered, concentrated, and purified via silica chromatography eluting the product with dichloromethane to afford the title compound as a brown oil, 6.8 g, 81%. MS M$^+$+1 254. The structure is confirmed by $^1$H NMR spectroscopy.

Step B (3-Dimethylcarbamoylsulfanyl-phenyl)-acetic acid methyl ester (3-Dimethylthiocarbamoyloxy-phenyl)-acetic acid methyl ester (6.8 g, 26.84 mmol) is stirred in tetradecane (30 mL) at 255 deg C. for 8 hr. The mixture is cooled, the residue is purified by silica chromatography eluting the product with hexanes to 1:1 hexanes:ethyl acetate to afford the title compound as an orange oil, 4.9 g, 58%. MS M$^+$+1 254. The structure is confirmed by $^1$H NMR spectroscopy.

Step C (3-Mercapto-phenyl)-acetic acid methyl ester

A mixture of (3-dimethylcarbamoylsulfanyl-phenyl)-acetic acid methyl ester (2.0 g, 7.9 mmol), potassium hydroxide (1.4 g, 24 mmol) methanol (50 mL), and water (5 mL) is stirred at reflux 3 hr. The mixture is concentrated, and product partitioned between 1M aqueous hydrochloric acid (50 mL) and ethyl acetate (3× 75 mL). The combined extracts are dried over anhydrous magnesium sulfate, filtered and concentrated. The residue is taken up in methanol (50 mL), 2 mL concentrated sulfuric acid is added, and the mixture refluxed 3 hr. The mixture is concentrated, and the residue purified by silica chromatography eluting with 7:3 hexanes:ethyl acetate to afford the title compound as a pale yellow oil, 1.0 g, 69%. MS M$^+$+1 183. The structure is confirmed by $^1$H NMR spectroscopy.

Preparation 17

3-(4-Iodomethyl-2-methyl-phenyl)-propionic acid methyl ester

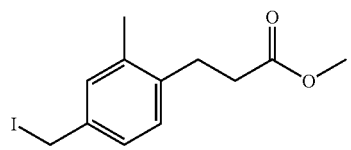

Step A 3-(4-Hydroxymethyl-2-methyl-phenyl)-acrylic acid methyl ester

A mixture of methyl-4-bromo-3-methylbenzoate (5.7 g, 24.88 mmol), lithium aluminum hydride (29 mL, 29 mmol, 1 M solution in tetrahydrofuran) and tetrahydrofuran (100 mL) is stirred in ice/water for 1 hr. The reaction is quenched with aqueous hydrochloric acid (50 mL, 1 M). The product is extracted into ethyl acetate (3× 100 mL). The combined extracts are dried over anhydrous magnesium sulfate, filtered and concentrated. The crude product is taken up in propionitrile (100 mL). Methylacrylate (10 mL, 121.5 mmol), palladium acetate (1.12 g, 5 mmol), tri-o-tolylphosphine (3.0 g, 10 mmol), and N,N-diisopropyl ethylamine (8.7 mL, 50 mmol) are sequentially added and the resulting reaction mixture is heated to 110 deg C. 3 hr. The mixture is concentrated, and the residue diluted with aqueous hydrochloric acid (100 mL, 1M).The product is extracted with dichloromethane (2× 100 mL) and ethyl acetate (100 mL). The combined extracts are dried over anhydrous magnesium sulfate, filtered, concentrated, and purified via silica chromatography eluting with 7:3 hexanes:ethyl acetate to 1:1 hexanes:ethyl acetate to afford the pure product as a yellow oil, 4.7 g, 91%. MS M$^+$+1 207. The structure is confirmed by $^1$H NMR spectroscopy.

Step B 3-(4-Hydroxymethyl-2-methyl-phenyl)-propionic acid methyl ester

A mixture of 3-(4-Hydroxymethyl-2-methyl-phenyl)-acrylic acid methyl ester (4.7 g, 22.8 mmol), Raney nickel (0.668 g) and tetrahydrofuran (618 mL) is shaken under 60 psig. Hydrogen 24 hr. The catalyst is filtered off, and the mixture is concentrated to afford the product as a pale yellow oil, 4.3 g, 91%. The structure is confirmed by $^1$H NMR spectroscopy.

Step C 3-(4-Iodomethyl-2-methyl-phenyl)-propionic acid methyl ester

A mixture of 3-(4-Hydroxymethyl-2-methyl-phenyl)-propionic acid methyl ester (0.62 g, 2.98 mmol), triphenyl phosphine (0.86 g, 3.27 mmol) and dichloromethane (10 mL) is stirred at room temperature. A solution of iodine (0.83 g, 3.27 mmol) in benzene (5 mL) is added and the black mixture is stirred at room temperature 2 hr. The brown mixture is diluted with 10% aqueous sodium hydrogen sulfite (5 mL) and the resulting clear mixture is washed with ethyl acetate (3× 50 mL). The combined extracts are dried over anhydrous magnesium sulfate, filtered and concentrated. The residue is purified via silica chromatography eluting with 9:1 hexanes:ethyl acetate to afford the title compound as a crystalline ivory solid, 0.68 g, 72%. MS M$^+$+1 319. The structure is confirmed by $^1$H NMR spectroscopy.

Preparation 18

(4-Bromo-2-methyl-phenoxy)-acetic acid methyl ester

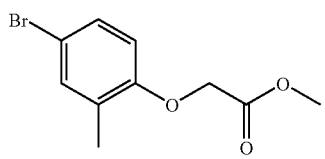

Step A (4-Bromo-2-methyl-phenoxy)-acetic acid methyl ester

A mixture of 4-bromo-2-methylphenol (1.0 g, 5.35 mmol), sodium hydride (0.26 g, 6.42 mmol, 60% mineral oil), N,N- dimethylformamide (10 mL), and methyl-2-bromoacetate (0.56 mL, 5.88 mmol) is stirred at room temperature 18 hr. The mixture is diluted with water (50 mL) and the product extracted to ethyl acetate (3× 50 mL). The combined extracts are dried over anhydrous magnesium sulfate, filtered, concentrated and purified via silica chromatography eluting with 8:2 hexanes:ethyl acetate to afford title compound as a colorless oil, 1.03 g, 74%. MS M+ 259. The structure is confined by ¹H NMR spectroscopy.

Preparation 19

3-(4-Amino-2-methyl-phenyl)-propionic acid methyl ester

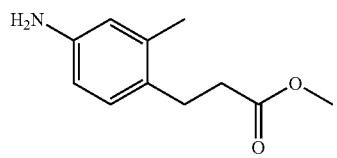

Step A 3-(2-Methyl-4-nitro-phenyl)-acrylic acid methyl ester

To a solution of 2-bromo-5-nitrotoluene (3.11 g, 14.39 mmol) in propionitrile (105 mL) is added DIPEA (5.1 mL, 29.28 mmol). The mixture is degassed three times. Methyl acrylate (5.2 mL, 57.74 mmol) is added and the mixture is degassed. Tri-o-tolylphosphine (1.77 g, 5.82 mmol) and Pd(OAc)₂ (0.64 g, 2.85 mmol) are added and the mixture is degassed a final two times followed by heating at 110° C. for 4 h. Upon cooling, the mixture is passed through Celite and the filtrate is concentrated. The residue is partitioned between Et₂O and 1N HCl. The organics are washed with saturated NaHCO₃ and brine, and dried with Na₂SO₄. The crude material is purified by flash chromatography to yield the title compound (2.90 g, 91%).

Step B 3-(4-Amino-2-methyl-phenyl)-propionic acid methyl ester

A mixture of 3-(2-Methyl-4-nitro-phenyl)-acrylic acid methyl ester (1.47 g, 6.64 mmol) and 5% Pd/C (0.29 g) in MeOH (100 mL) is exposed to a hydrogen atmosphere (60 psi) for 12 h. The mixture is filtered through Celite and purified by flash chromatography to yield the title compound (0.99 g, 77%).

Preparation 20

3-(2-Methyl-4-methylaminomethyl-phenyl)-propionic acid methyl ester TFA salt

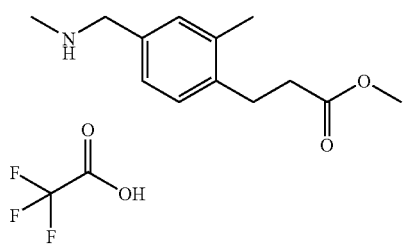

Step A 3-(4-Formyl-2-methyl-phenyl)-propionic acid methyl ester

A mixture of 3-(4-Hydroxymethyl-2-methyl-phenyl)-propionic acid methyl ester (0.49 g, 2.35 mmol) and MnO₂ (0.80 g, 9.20 mmol) in chloroform (5 mL) is stirred at RT for 4 days. The mixture is filtered through Celite; the Celite is washed with copious amounts of EtOAc. The filtrate is concentrated and purified by flash chromatography to yield the title compound (0.29 g, 60%).

Step B 3-(2-Methyl-4-methylaminomethyl-phenyl)-propionic acid methyl ester trifluoroacetic acid To a mixture of 3-(4-Formyl-2-methyl-phenyl)-propionic acid methyl ester (0.27 g, 1.31 mmol) and methylamine (2M in THF, 0.60 mL, 1.20 mmol) in anhydrous CH₂Cl₂ (10 mL) is added 4Å molecular sieves followed by acetic acid (0.090 mL, 1.57 mmol). The mixture is stirred at RT for 1.5 h. Sodium triacetoxyborohydride (0.39 g, 1.85 mmol) is added, and the mixture is stirred overnight. The reaction is quenched with saturated NaHCO₃. The organics are washed with saturated NaHCO₃ and brine, and dried with MgSO₄. Upon concentration, the mixture is purified by reverse phase chromatography to yield the title compound (0.12 g, 45%).

3-(4-Aminomethyl-2-methyl-phenyl)-propionic acid methyl ester

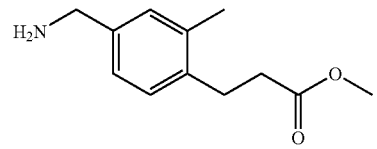

Step A 3-(4-Chloromethyl-2-methyl-phenyl)-propionic acid methyl ester

To a 0° C. solution of 3-(4-Hydroxymethyl-2-methyl-phenyl)-propionic acid methyl ester (1.02 g, 4.90 mmol) in anhydrous CH₂Cl₂ (15 mL) is added triethylamine (0.75 mL, 5.38 mmol) followed by thionyl chloride (0.40 mL, 5.48 mmol). The mixture is allowed to warm to RT overnight. Water is added, and the mixture is extracted with CH₂Cl₂. The organics are dried with MgSO₄ and concentrated. The crude material is purified by flash chromatography to yield the title compound (1.01 g, 91%).

Step B 3-(4-Azidomethyl-2-methyl-phenyl)-propionic acid methyl ester

To a solution of 3-(4-Chloromethyl-2-methyl-phenyl)-propionic acid methyl ester (0.52 g, 2.31 mmol) in DMF (7 mL) is added sodium azide (0.25 g, 3.84 mmol). The mixture is stirred overnight. Water is added, and the mixture is extracted with EtOAc. The organics are dried with Na₂SO₄ and concentrated to yield the title compound (0.49 g, 91%). The material is used without further purification.

Step C 3-(4-Aminomethyl-2-methyl-phenyl)-propionic acid methyl ester

A mixture of 3-(4-Azidomethyl-2-methyl-phenyl)-propionic acid methyl ester (0.20 g, 0.86 mmol) and 5% Pd/C (32 mg) in EtOH (50 mL) is exposed to a hydrogen atmosphere (60 psi) at RT overnight. Upon filtering the mixture through Celite, the filtrate is concentrated to yield the title compound (0.14 g, 78%). The material is used without further purification.

Preparation 22

4-(2-Methoxycarbonyl-ethyl)-3-methyl-benzoic acid

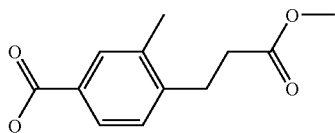

Step A

4-Bromo-3-methyl-benzoic acid benzyl ester

To a solution of 4-Bromo-3-methyl-benzoic acid benzyl (25.3 g, 0.118 mol) in DMF (200 mL) is added Cs2CO3 (76.6 g, 0.235 mol), followed by benzyl bromide (15.4 mL). After stirred at room temperature for 2 h, the reaction mixture is diluted with ethyl acetate, filtered through celite. The filtrate is washed with water and brine, dried over sodium sulfate, concentration yields the title product.

Step B 4-(2-Methoxycarbonyl-vinyl)-3-methyl-benzoic acid benzyl ester

To a solution of 4-bromo-3-methyl-benzoic acid benzyl ester (36 g, 118 mmol) in propronitrile (1000 mL) is added methyl acrylate (43.3 mL) and diisopropylethyl amine (42 mL), the solution is degassed and filled with nitrogen for three times. To this mixture are added tri-o-tolyl-phosphane (14.5 g) and palladium acetate (5.34 g) under nitrogen, then heated at 110° C. overnight, cooled to room temperature, filtered through celite. The solvent is evaporated, the residue is taken into ethyl acetate and washed with water and brine, dried over sodium sulfate. Concentration and column chromatography on silica gel eluted with hexanes and ethyl acetate yields the title compound (31 g, 84.7%).

Step C 4-(2-Methoxycarbonyl-ethyl)-3-methyl-benzoic acid

A mixture of 4-(2-methoxycarbonyl-vinyl)-3-methyl-benzoic acid benzyl ester (11.6 g, 37.4 mmol) and Pd/C (5%, 1.5 g) in THF (300 mL) and methanol (100 mL) is stirred under 60 psi of hydrogen overnight. Catalyst is filtered off, filtrate is concentrated giving the title compound (8.3 g, 100%).

2-(3-Hydroxy-phenyl)-2-methyl-propionic acid ethyl ester

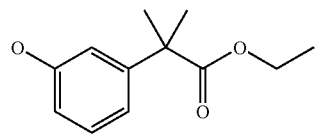

Step A 2-(3-Methoxy-phenyl)-propionic acid ethyl ester

To a solution of LDA (2M, 16.5 mL) in THF (10 mL) at −70° C. was added a solution of (3-methoxy-phenyl)-acetic acid methyl ester (5.4 g, 30 mmol) in THF (10 mL). After 40 minutes at −70° C., iodomethane (2.5 mL, 40 mmol) was added. The mixture was stirred at room temperature overnight. It was diluted with EtOAc, washed with 1N HCl. The organic layer was dried over Na2SO4 and concentrated to give the titled compound as an oil: 5.9 g (quant.)

Step B 2-(3-Methoxy-phenyl)-2-methyl-propionic acid ethyl ester

To a solution of LDA (2M, 11.4 mL) in THF (10 mL) at −70° C. was added a solution of 2-(3-methoxy-phenyl)-propionic acid ethyl ester (4 g, 20.6 mmol) in THF (10 mL). After 1 hour at −70° C., iodomethane (1.7 mL, 26.8 mmol) was added and the mixture was stirred at room temperature overnight. It was diluted with EtOAc and washed with 1N HCl. The organic was concentrated to give the titled compound as an oil: 4 g (93%).

Step C 2-(3-Hydroxy-phenyl)-2-methyl-propionic acid ethyl ester

To a solution of 2-(3-Methoxy-phenyl)-2-methyl-propionic acid ethyl ester (4 g, 19.2 mmol) in dichloromethane (20 mL) at 0° C. was added BBr3 (1M in dichloromethane, 50 mL). After 2 hours at ambient temperature, it was quenched with MeOH. Solvent was evaporated and the residue was partitioned between EtOAc and 1N HCl. The organic was concentrated and purified by column chromatography (0 to 30% EtOAc in hexanes) to give the titled compound as a solid: 2.6 g (70%). ESMS-: 193 (M−1); 1H NMR is consistent with desired product.

Preparation 24

3-(4-Hydroxy-2-methyl-phenyl)-2,2-dimethyl-propionic acid methyl ester

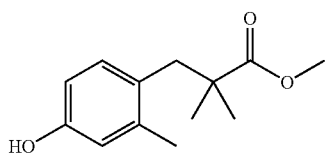

Step A

2-Methyl-4-anisaldehyde

A mixture of 2,3-dimethylanisole (50 g, 0.37 mol), $Cu^{2+}$ sulfate pentahydrate (90 g, 0.36 mol), and potassium peroxydisulfate (301 g, 1.11 mol) in acetonitrile/water (1:1, 2.6 L) was stirred vigorously and heated to reflux for 30 minutes. Thin layer chromatography (Hexane:EtOAc, 8:2) showed no starting material and one new spot. The reaction was cooled to room temperature and extracted with $CH_2Cl_2$ (4 L) and washed with water (2 L). The layers were separated and the aqueous layer was again extracted with $CH_2Cl_2$. The organic layers were combined and concentrated, 55 g obtained (~100%), product was taken on as is. $^1$H-NMR (DMSO-$d_6$): 10.05 (s, 1H), 7.78 (m, 1H), 6.95 (m, 1H), 6.88 (s, 1H), 3.84 (s, 3H), 2.6 (s, 3H).

Step B

4-Methoxy-2-methylbenzyl alcohol $NaBH_4$ (14.82 g, 0.39 mol) was added to a solution of 2-Methyl-4-anisaldehyde (55 g, 0.37 mol) in EtOH (800 mL). TLC shows multiple spots but a disappearance of starting material. The reaction was quenched with water (3 L), acidified with 5N HCl, and extracted with $Et_2O$. The organics were separated and concentrated. The crude product was purified by Biotage 75L (Hexane:EtOAc, 9:1) to afford 17.35 g (30%). $^1$H-NMR (CDCl$_3$): 7.22 (m, 1H), 6.7 (m, 2H), 4.64 (s, 2H), 3.8 (s, 3H), 2.4 (s, 3H).

Step C

Acetic acid 4-methoxy-2-methyl-benzyl ester

A solution of 4-Methoxy-2-methylbenzyl alcohol (17.35 g, 0.114 mol) in $CH_2Cl_2$ (900 mL) was cooled 0°C. TEA (23.3 mL, 0.167 mol) and acetyl chloride (9.3 mL, 0.131 mol) were added. The reaction was allowed to stir for 1 h and was then quenched with 1N HCl, washed with aq. $NaHCO_3$, brine, dried ($Na_2SO_4$), and concentrated to an oil (22.14 g, ~100%). $^1$H-NMR (CDCl$_3$): 7.24 (m, 1H), 6.73 (m, 2H), 5.08 (s, 2H), 3.8 (s, 3H), 2.33 (s, 3H), 2.08 (s, 3H).

Step D

3-(4-Methoxy-2-methyl-phenyl)-2,2-dimethyl-propionic acid methyl ester

Acetic acid 4-methoxy-2-methyl-benzyl ester (22.14 g, 0.114 mol) was dissolved in $CH_2Cl_2$ and treated with 1-methoxy-1trimethylsiloxy-2-methyl-1-propene (53.3 g, 0.306 mol) and $Mg(ClO_4)_2$ (2.58 g, 0.012 mol). The reaction was stirred overnight at room temperature. Upon completion the reaction was washed with water, brine, and dried with $Na_2SO_4$. The crude product was purified (Biotage 75M (Hexane:EtOAc, 9:1–8:2)) to obtain 18.7 g (70%). $^1$H-NMR (CDCl$_3$): 6.97 (d, 1H1), 6.7 (m, 2H), 3.8 (s, 3H), 3.64 (s, 3H), 2.85 (s, 2H), 2.3 (s, 3H), 1.2 (s, 6H).

Step E

3-(4-Hydroxy-phenyl)-2,2-dimethyl-propionic acid methyl ester $BBr_3$ (1M in $CH_2Cl_2$, 79 ml) was cooled to 0° C. and 3-(4-Methoxy-2-methyl-phenyl)-2,2-dimethyl-propionic acid methyl ester (9.35 g, 0.0395 mol) was added dropwise over 10 minutes. After stirring for 1 h at 0° C. the reaction was quenched with 1:1 MeOH:$CH_2Cl_2$. The organics were concentrated and the resulting oil was run through a plug of silica gel with Hexane:EtOAc (8:2). Fractions 1,2 were concentrated and 7.5 g (85%) of the desired compound were isolated. $^1$H-NMR (CDCl$_3$): 6.87 (d, 1H), 6.6 (m, 2H), 4.9 (bs, 1H), 3.64 (s, 3H), 2.82 (s, 2H), 2.22 (s, 3H), 1.2 (s, 6H).

Preparation 25

2-(4-Hydroxy-phenoxy)-2-methyl-propionic acid ethyl ester

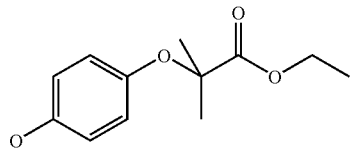

Preparation 26

2-(4-Hydroxy-phenylsulfanyl)-2-methyl-propionic acid ethyl ester

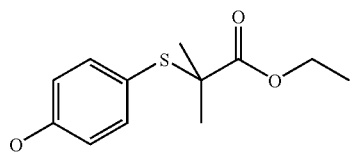

Preparation 27

4-hydroxy-2-ethyl-dihydro-ethyl cinnamate

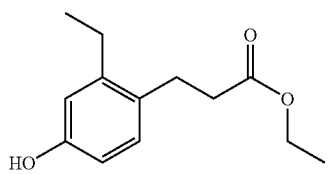

Step A

3-iodobenzyloxybenzene

Sodium hydride (mineral dispersion 60%) (1.36 g, 34.10 mmol) is added slowly to a solution of 3-iodophenol (5.0 g, 22.73 mmol) and TABI (0.84 g, 2.27 mmol) in THF (113 mL), and the mixture is stirred overnight. The crude is treated with water and extracted with EtOAc. The organic layers are combined, dried over sodium sulfate, filtered and concentrated under reduced pressure. Purification by flash chromatography, eluting with hexane:EtOAc 10:1 provides the title compound (7.00 g, 99%). Rf=0.77 (hexane:EtOAc 5:1). $^1$H NMR (200 MHz, CDCl$_3$): 5.03 (s, 2H), 6.93 (m, 1H), 7.02 (d, 1H, J=8.3 Hz), 7.27-7.34 (m, 7H)

Step B

3-ethylbenzyloxybenzene

Copper (I) chloride (0.016 g, 0.17 mmol), ethyl iodide (0.40 mL, 5.03 mmol) and diethyl zinc (1.0 M, THF) (4.61 mL, 4.61 mmol) are added successively to a solution of manganese bromide (0.054 g, 0.25 mmol) in 1,3-dimethyl-3,4,5,6-tetrahydro-2(1H)pyrimidinone (4.20 mL), and the mixture is stirred at for 4 h. A solution of 3-iodobenzyloxybenzene (1.3 g, 4.19 mmol) and dichloro(diphenylphosphinoferrocene)-Pd(II) (DCM complex) (0.14 g, 0.17 mmol) in THF (21 mL) is added, and the mixture is stirred under reflux for 2.5 h. The mixture is cooled to r.t. and HCl 1N is added. The mixture is extracted with EtOAc. The organic layers are combined, dried over sodium sulfate, filtered and concentrated under reduced pressure. Purification by flash chromatography, eluting with hexane:EtOAc 20:1 provides the title compound (0.81 g, 91%). Rf=0.82 (hexane:EtOAc 5:1). $^1$H NMR (200 MHz, CDCl$_3$): 1.30 (t, 3H, J=7.8 Hz), 2.70 (q, 2H, J=7.5 Hz), 5.11 (s, 2H), 6.86-6.91 (m, 3H), 7.23-7.53 (m, 6H).

Step C

4-bromo-3-ethylbenzyloxybenzene

N-bromosuccinimide (0.75 g, 4.20 mmol) is added to a solution of 3-ethylbenzyloxybenzene (0.81 g, 3.82 mmol) in ACN (19 mL) and the mixture is stirred for an hour. The solvent is evaporated in vacuo and the resultant is purified by flash chromatography, eluting with hexane:EtOAc 20:1 to give the title compound (1.09 g, 98%). Rf=0.74 (hexane:EtOAc 5:1). $^1$H NMR (200 MHz, CDCl$_3$): 1.22 (t, 3H, J=7.5 Hz), 2.72 (q, 2H, J=7.5 Hz), 5.04 (s, 2H), 6.69 (dd, 1H, J=3.0, 8.6 Hz), 6.88 (d, 2H, J=3.0 Hz), 7.32-7.45 (m, 6H).

Step D

4-benzyloxy-2-ethyl-ethyl trans-cinnamate

A mixture of 4-bromo-3-ethylbenzyloxybenzene (0.95 g, 3.27 mmol), palladium acetate (0.073 g, 0.33 mmol), tri-o-tolylphosphine (0.20 g, 0.65 mmol), DIPEA (1.14 mL, 6.53 mmol) and ethyl acrylate (1.42 mL, 13.06 mmol) in propionitrile (49 mL) is stirred at 90° C. under nitrogen overnight. The solution is filtered through Celite and washed with EtOAc. The mixture is concentrated under reduced pressure. Purification by flash chromatography, eluting with hexane:EtOAc 10:1 provides the title compound (0.43 g, 43%). Rf=0.22 (hexane:EtOAc 20:1). $^1$H NMR (300 MHz, CDCl$_3$): 1.25 (t, 3H, J=7.7 Hz), 1.37 (t, 3H, J=7.1 Hz), 2.80 (q, 2H, J=7.7 Hz), 4.30 (q, 2H, J=7.3 Hz), 5.09 (s, 2H), 6.32 (d, 1H, J=15.7 Hz), 6.83-6.87 (m, 2H), 7.35-7.47 (m, 5H), 7.56 (d, 1H, J=8.5 Hz), 8.01 (d, 1H, J=15.9 Hz).

Step E

A solution of 4-benzyloxy-2-ethyl-ethyl trans-cinnamate (0.43 g, 1.39 mmol) and pd/C (10%) (0.074 g, 0.07 mmol) in methanol (14 mL) is stirred under 1 atm of hydrogen. After 4 h, the mixture is filtered through Celite and washed with methanol and concentrated under reduced pressure. Purification by flash chromatography, eluting with hexane:EtOAc 5:1 provides the title compound (0.29 g, 63%).

Rf: 0.17 (hexane:EtOAc 5:1). $^1$H NMR (300 MHz, CDCl$_3$): 1.19 (t, 3H, J=7.5 Hz), 1.26 (t, 3H, J=7.3 Hz), 2.54-2.63 (m, 4H), 2.87-2.92 (m, 2H), 4.16 (q, 2H, J=7.1 Hz), 5.94 (s, 1H), 6.62 (dd, 1H, J=2.6, 8.3 Hz), 6.70 (d, 1H, J=2.6 Hz), 6.99 (d, 1H, J=8.3 Hz).

Preparation 28

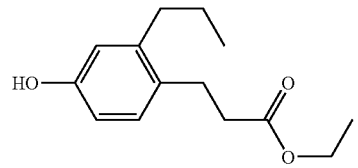

Step A

3-propylbenzyloxybenzene

Copper (I) chloride (0.016 g, 0.17 mmol), propyl iodide (0.49 mL, 5.03 mmol) and diethyl zinc (1.0 M, THF) (4.61 mL, 4.61 mmol) is added successively to a solution of manganese bromide (0.054 g, 0.25 mmol) in 1,3-dimethyl-3,4,5,6-tetrahydro-2(1H)pyrimidinone (4.20 mL), and the mixture is stirred at r.t. for 4 h. A solution of 3-iodobenzyloxybenzene (Step A) (1.3 g, 4.19 mmol) and dichloro-(diphenylphosphinoferrocene)palladium (II) (DCM complex) (0.14 g, 0.17 mmol) in THF (21 mL) is added, and the mixture is stirred under reflux for 2.5 h. The mixture is cooled to r.t. and 1N HCl is added. The mixture is extracted with EtOAc, and the organic layers are combined, dried over sodium sulfate, filtered and concentrated under reduced pressure. Purification by flash chromatography, eluting with hexane:EtOAc 20:1 provides the title compound together with 25% of 3-ethylbenzyloxybenzene (0.85 g, 81% overall). Rf=0.82 (hexane:EtOAc 5:1). $^1$H NMR (200 MHz, CDCl$_3$): 1.13-1.20 (m, 3H), 1.81-1.92 (m, 2H), 2.74-2.85 (m, 2H), 5.22 (s, 2H), 7.00-7.03 (m, 3H), 7.37-7.61 (m, 6H).

Step B

4-bromo-3-propylbenzyloxybenzene

N-bromosuccinimide (0.66 g, 3.74 mmol) is added to a solution of 3-propylbenzyloxybenzene (0.85 g, 3.40 mmol) in ACN (17 mL), and the mixture is stirred for an hour. The solvent is evaporated in vacuo and purified by flash chromatography by eluting with hexane:EtOAc 20:1 to give the title compound together with 25% of 4-bromo-3-ethylbenzyl-oxybenzene (1.03 g, 99% overall). Rf=0.74 (hexane:EtOAc 5:1).

¹H NMR (200 MHz, CDCl₃): 1.00 (t, 3H, J=7.2 Hz), 1.65 (sext, 2H, J=7.2 Hz), 2.71 (q, 2H, J=7.5 Hz), 5.05 (s, 2H), 6.71 (dd, 1H, J=3.0, 8.6 Hz), 6.91 (d, 2H, J=3.0 Hz), 7.32-7.47 (m, 6H).

Step C 4-benzyloxy-propylbenzaldehyde n-BuLi (1.6 M in hexane) (7.03 mL, 11.25 mmol) is added to a solution of 4-bromo-3-propylbenzyloxybenzene (2.29 g, 7.50 mmol) in THF (30 mL) under nitrogen at −78° C., and the mixture is stirred for 30 minutes. N-Formylpiperidine (1.25 mL, 11.25 mmol) is added and stirred for 4 h. The mixture is allowed to gradually warm up to −40° C., and then water is added and extracted with EtOAc. The organic layers are combined, dried and filtered, and then the solvent is evaporated in vacuo. Purification by flash chromatography by eluting with hexane:EtOAc 10:1 provides the title compound together with 25% of 4-bromo-3-ethylbenzyloxybenzene (1.00 g, 52% overall). Rf=0.63 (hexane:EtOAc 5:1). ¹H NMR (300 MHz, CDCl₃): 1.26 (t, 3H, J=7.7 Hz), 1.65 (sext, 2H, J=7.2 Hz), 2.99 (q, 2H, J=7.7 Hz), 5.13 (s, 2H), 6.84-6.94 (m, 2H), 7.33-7.46 (m, 5H), 7.79 (d, 1H, J=8.2 Hz), 10.12 (s, 1H).

Step D 4-benzyloxy-2-propyl-ethyl trans-cinnamate

Method 1: A mixture of 4-bromo-3-ethylbenzyl-oxybenzene (0.56 g, 1.85 mmol), palladium acetate (0.042 g, 0.18 mmol), tri-o-tolylphosphine (0.11 g, 0.37 mmol), DIPEA (0.64 mL, 3.70 mmol) and ethyl acrylate (0.80 mL, 7.42 mmol) in propionitrile (28 mL) is stirred at 90° C. a under nitrogen overnight. The mixture is filtered through Celite, washed with EtOAc and concentrated under reduced pressure. Purification by flash chromatography by eluting with hexane:EtOAc 10:1 provides the title compound with a 25% of 4-benzyloxy-2-ethyl-ethyl trans-cinnamate (0.22 g, 37% overall).

Method 2: Triethylphosphono acetate (0.15 mL, 0.74 mmol) is added to a solution of 4-benzyloxy-propylbenzaldehyde (Step C) (0.16 g, 0.62 mmol) and potassium carbonate (0.26 g, 1.86 mmol) in ethanol (2.10 mL), and the mixture is stirred under reflux for 2.5 h. The mixture is cooled to r.t. and water is added. The mixture is extracted with EtOAc, and the organic layers are combined, dried and filtered. The solvent is evaporated in vacuo. Purification by flash chromatography by eluting with hexane:EtOAc 5:1 provides the title compound together with 25% of 4-benzyloxy-2-ethyl-ethyl trans-cinnamate (0.17 g, 86% overall). Rf=0.22 (hexane:EtOAc 20:1). ¹H NMR (300 MHz, CDCl₃): 0.99 (t, 3H, J=7.3 Hz), 1.25 (t, 3H, J=7.5 Hz), 1.58-1.69 (m, 2H), 2.75 (q, 2H, J=7.1 Hz), 4.29 (q, 2H, J=7.3 Hz), 5.10 (s, 2H), 6.31 (d, 1H, J=15.7 Hz), 6.85 (d, 2H, J=7.3 Hz), 7.35-7.47 (m, 5H), 7.56 (d, 1H, J=7.9 Hz), 8.00 (d, 1H, J=15.7 Hz)

Step E 4-hydroxy-2-propyl-dihydro-ethyl cinnamate

A solution of 4-benzyloxy-2-propyl-ethyl trans-cinnamate (0.44 g, 1.35 mmol) and pd/C (10%) (0.14 g, 0.14 mmol) in methanol (13 mL) is stirred under 1 atm of hydrogen. After 4 h, the mixture is filtered through Celite, washed with methanol, and concentrated under reduced pressure. Purification by flash chromatography by eluting with hexane:EtOAc 5:1 provides the title compound (0.17 g, 54%) with a 25% of 4-hydroxy-2-ethyl-dihydro-ethyl cinnamate. The mixture is separated by HPLC (reverse phase purification) under acidic conditions (ACN:TFA=99.95:0.05). Rf=0.17 (hexane:EtOAc 5:1). ¹H NMR (300 MHz, CDCl₃): 0.97 (t, 3H, J=7.5 Hz), 1.26 (t, 3H, J=7.1 Hz), 1.59 (sext, 2H, J=7.5 Hz), 2.55 (q, 4H, J=8.9 Hz), 2.89 (t, 2H, J=7.5 Hz), 4.16 (q, 2H, J=7.13 Hz), 5.72 (s, 1H), 6.71 (dd, 1H, J=3.0, 8.1 Hz), 6.67 (d, 1H, J=2.6 Hz), 6.99 (d, 1H, J=8.3 Hz Preparation 29

4-(4-hydroxy-2-methylphenyl)-butyric acid ethyl ester

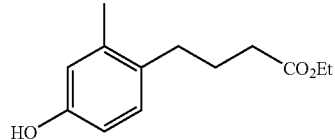

Step A 4-benzyloxy-2-methyl bromobenzene

To a solution of 15 g (80.2 mmol) of 4-bromo-3-methyl-phenol and 1.5 g (10% in weight) of tetrebutylammonium iodide in THF (100 ml) is added 60% NaH (2.88 gr, 120 mmol) at 0° C. After the mixture is stirred at 0° C. for 30 min, benzyl bromide (14.3 ml 120 mmol) is added drop wise. The reaction is stirred at r.t. overnight under argon atmosphere. Then the reaction is poured into ice-water and extracted with EtOAc (3×100 ml). The organic extracts are dried over MgSO₄ and concentrated. The title compound (16.5 g, 66%) is isolated by precipitation in hexane.

Step B 4-(4-benzyloxy-2-methyl-phenyl)-4-oxo-butyric acid

A solution of 4-benzyloxy-2-methyl bromobenzene (4 g, 14.4 mmol) in THF (25 ml) is added drop wise over a mixture of Mg (414 mg, 17.3 mmol), 1,2-dibromoethane (a few drops) and I₂ (a crystal) at 70° C. under argon atmosphere. After the addition is completed, the mixture is stirred at 70° C. for 3 hours. Grignard reagent is added over a solution of succinic anhydride (1.73 gr, 17.3 mmol) and Fe(acac)₃ (254 mg, 0.7 mmol) in 25 ml of THF over argon atmosphere and is stirred overnight at r.t. The reaction is quenched with sat NH₄Cl and extracted with EtOAc (3× 50 ml). The organic phase is basified with 2N NaOH, and the aqueous phase is washed with EtOAc (3× 50 ml). The aqueous phase is acidified with 2N HCl and then extracted with EtOAc (3× 50 ml), dried over MgSO$_4$ and concentrated to give 3.4 g (40%) of the title compound. The crude is used for the next step without further purification.

Step C 4-(4-benzyloxy-2-methylphenyl)-4-oxo-butyric acid ethyl ester

A solution of 4-(4-benzyloxy-2-methyl-phenyl)-4-oxo-butyric acid (1.6 g, 5.6 mmol) and H$_2$SO$_4$ (1 ml) in EtOH (50 ml) is stirred at 80° C. overnight. The solvent is evaporated, and water (100 ml) and sat. NaHCO$_3$ is added up to pH=9. The aqueous phase is extracted with EtOAc (3× 50 ml) and the organics are dried over MgSO$_4$ and concentrated to give about 1.3 g (71%) of the title compound, which is used for the next step without further purification.

Step D 4-(4-hydroxy-2-methylphenyl)-butyric acid ethyl ester

A mixture of 4-(4-benzyloxy-2-methylphenyl)-4-oxo-butyric acid ethyl ester (1.2 g, 3.4 mmol), Pd/C (120 mg) 10% in 10 ml of AcOH is hydrogenated at 60 psi overnight. The mixture is filtered over celite, washed with EtOH and evaporated. Water (50 ml) and saturated NaHCO$_3$ are added until neutral pH is achieved. The aqueous phase is extracted with AcOEt (3× 50 ml), and the organic phase is dried over MgSO$_4$ and concentrated. The crude is purificated using silica gel chromatography (hexane/EtOAc 6:1) to afford 700 mg (92%) of the title compound.

Preparation 30

4-hydroxy-2-fluoro-dihydro-ethyl cinnamate

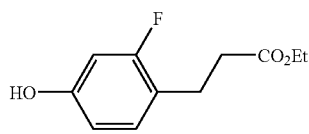

Step A 3-fluorobenzyloxyphenol

Benzyl bromide (2.9 mL, 24.08 mmol) is added to a suspension of 3-fluorophenol (3.0 g, 26.76 mmol) and K$_2$CO$_3$ (4.0 g, 28.94 mmol) in DMF (30 mL), and the mixture is stirred at r.t. for 5 h. It is acidified with diluted HCl (1M) and partitioned between EtOAc and H$_2$O. The organic layer is dried, filtered and concentrated, and the product is purified by flash chromatography on SiO$_2$ (3% EtOAc/hexanes) to afford 4.7 g of the title compound (87%, colorless oil).

Step B 4-bromo-3-fluorobenzyloxyphenol

NBS (2.11 g, 11.88 mmol) is added to a solution of 3-fluorobenzyl-oxyphenol (2.4 g, 11.88 mmol) in CH$_3$CN (50 mL, HPLC grade). The mixture is stirred at r.t. overnight (c.a. 14 h) and extracted with EtOAc and H$_2$O. The organic layer is dried, filtered and concentrated, and the resulting crude residue is flash chromatographed on SiO$_2$ (5% EtOAc/hexanes) to afford 3.3 g of title compound (99%, white solid).

Step C 3-fluoro-4-ethylacrylate-benzyloxyphenol

Ethyl acrylate (6.73 mL, 74.73 mmol) is added to a solution of 4-bromo-3-fluorobenzyloxyphenol (3.5 g, 12.455 mmol), Pd(OAc)$_2$ (280 mg, 1.245 mmol), P(o-tol)$_3$ (758 mg, 2.49 mmol) and DIPEA (6.5 mL, 37.37 mmol) in EtCN (80 mL, HPLC grade). The mixture is warmed to 95° C. and stirred at that temperature for 1 h. It is allowed to reach r.t., filtered trough Celite and partitioned between EtOAc and H$_2$O. The organic layer is dried, filtered and concentrated, and the resulting crude is flash chromatographed on SiO$_2$ (2-3% EtOAc/hexanes) to afford 2.05 g of the Heck product (55%, white solid).

Step D 4-hydroxy-2-fluoro-dihydro-ethyl cinnamate

Palladium (120 mg, 10% on activated carbon, 0.112 mmol) is added to a solution of the fluorobenzyloxy compound of Step C (1.2 g, 4.0 mmol), and the mixture is stirred under H$_2$ atmosphere (H$_2$ balloon) overnight (c.a. 14 h). The mixture is filtered trough Celite, and the solvent is removed in a rotatory evaporator. The crude residue is flash chromatographed on SiO$_2$ (10-20% EtOAc/hexanes) to afford 510 mg of the title compound (60%, colorless oil).

Preparation 31

4-hydroxy-2-chloro-dihydro-ethyl cinnamate

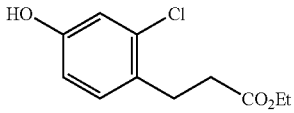

Step A 4-bromo-3-chlorobenzyloxyphenol

Benzyl bromide (0.83 mL, 6.95 mmol) is added to a suspension of 3-chloro-4-bromophenol (1.0 g, 4.82 mmol) and K$_2$CO$_3$ (960 mg, 6.95 mmol) in DMF (25 mL), and the mixture is stirred at r.t. for 3 h. It is acidified with diluted HCl (1M) and partitioned between Et$_2$O and H$_2$O. The organic layer is dried, filtered and concentrated, and the product is purified by flash chromatography on SiO$_2$ (1-2% EtOAc/hexanes) to afford 1.39 g of the title compound (97%, white solid).

Step B

3-chloro-4-ethylacrylate-benzyloxyphenol

Ethyl acrylate (5.0 mL, 55.5 mmol) is added to a solution of 4-bromo-3-chlorobenzyloxyphenol (2.7 g, 9.08 mmol), palladium acetate (215 mg, 0.96 mmol), P(o-tol)$_3$ (550 mg, 1.8 mmol) and Et$_3$N (3 mL, 21.5 mmol) in EtCN (100 mL, HPLC grade). The mixture is warmed to 95° C. and stirred at that temperature overnight (c.a. 16 h). It is allowed to reach r.t., filtered trough Celite and partitioned between EtOAc and H$_2$O. The organic layer is dried, filtered and concentrated, and the resulting crude is flash chromatographed on SiO$_2$ (5% EtOAc/hexanes) to afford 1.79 g of the Heck product (62%, white solid).

Step C

4-hydroxy-2-chloro-dihydro-ethyl cinnamate

Palladium (121 mg, 10% on activated carbon, 0.113 mmol) is added to a solution of the chlorobenzyloxyphenol (1.2 g, 3.79 mmol), and the mixture is stirred under H$_2$ atmosphere (H$_2$ balloon) overnight (c.a. 14 h). The mixture is filtered trough Celite, and the solvent is removed in a rotatory evaporator. The crude residue is flash chromatographed on SiO$_2$ (5-10% EtOAc/hexanes), and repurified by HPLC (normal phase) to afford 515 mg of the title compound (93%, colorless oil).

Preparation 32

Preparation of 4-hydroxy-2-ethyl-phenylsulfanyl-acetic acid ethyl ester

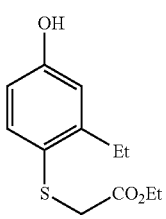

Step A

3-ethylbenzyloxyphenol

Benzyl bromide (4.92 mL, 41.36 mmol) is added to a suspension of 3-ethylphenol (5.055 g, 41.36 mmol) and K$_2$CO$_3$ (8.5 g, 61.5 mmol) in CH$_3$CN (50 mL, HPLC grade), and the mixture is stirred at r.t. for 5 h. The mixture is acidified with diluted HCl (1M) and partitioned between EtOAc and H$_2$O. The organic layer is dried, filtered and concentrated, and the product is purified by flash chromatography on SiO$_2$ (3% EtOAc/hexanes) to afford 8.3 g of 3-ethylbenzyloxyphenol (94%, colorless oil).

Step B

4-bromo-3-ethylbenzyloxyphenol

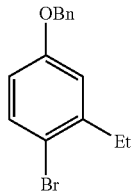

NBS (1.68 g, 9.438 mmol) is added to a solution of 3-ethylbenzyl-oxyphenol (2 g, 9.433 mmol) in CH$_3$CN (30 mL, HPLC grade). The mixture is stirred at r.t. overnight (c.a. 14 h) and extracted with EtOAc and H$_2$O. The organic layer is dried, filtered and concentrated, and the resulting crude residue is flash chromatographed on SiO$_2$ (2% EtOAc/hexanes) to afford 2.3 g of the bromide (84%, colorless oil).

Step C

4-benzyloxy-2-ethyl-phenylsulfanyl-acetic acid ethyl ester

Tert-BuLi (5.25 mL, 1.7 M solution, 8.94 mmol) is added to a −78° C. cooled solution of 4-bromo-3-ethylbenzyloxyphenol (1.3 g, 4.467 mmol) in THF (20 mL). The mixture is stirred at low temperature for 30 min and allowed to reach r.t. Sulfur (150 mg, 4.68 mmol) is added in one portion, and the reaction is stirred at r.t. for 5 min. Ethylbromoacetate (2.5 mL, 22.33 mmol) is added, and the mixture is stirred at r.t. overnight (c.a. 14 h). It is quenched with NH$_4$Cl (sat) and extracted with EtOAc/H$_2$O. The organic layer is dried, filtered and concentrated, and the crude residue is flash chromatographed on SiO$_2$ (2~4% EtOAc/hexanes) to afford 490 mg of the title compound (33%, colorless oil).

Step D
4-hydroxy-2-ethyl-phenylsulfanyl-acetic acid ethyl ester

TiCl$_4$ (1.3 mL, 1 M solution in CH$_2$Cl$_2$, 1.3 mmol) is added to a −78° C. cooled solution of the benzyloxyphenol (400 mg, 1.21 mmol) in CH$_2$Cl$_2$ (12 mL), and the mixture is allowed to reach 0° C., and then r.t. and stirred for 4 h. The reaction is quenched with H$_2$O and diluted with CH$_2$Cl$_2$. The organic layer is washed with brine, dried, filtered and concentrated. The crude residue is flash chromatographed on SiO$_2$ (5-10-15% EtOAc/hexanes) to afford 160 mg of the title compound (55%, colorless oil).

Preparation 33

4-hydroxy-2,6dimethyl-dihydro-ethyl cinnamate

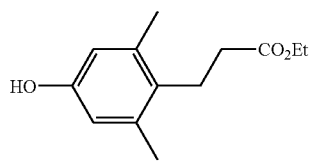

Step A

3,5-dimethyl-4-bromobenzyloxyphenol

Benzyl bromide (1.53 mL, 12.86 mmol) is added to a suspension of 3,5-dimethyl-4-bromophenol (2.6 g, 12.93 mmol) and $K_2CO_3$ (2.2 g, 14.47 mmol) in $CH_3CN$ (30 mL, HPLC grade). The mixture is stirred at r.t. for 16 h. It is acidified with diluted HCl (1M) and partitioned between EtOAc and $H_2O$. The organic layer is dried, filtered and concentrated, and the product is purified by flash chromatography On $SiO_2$ (5% EtOAc/hexanes) to afford 3.66 g of the benzyloxyphenol (97%, white solid).

Step B

3,5-dimethyl-4-ethylacrylate-benzyloxyphenol

Ethyl acrylate (6 mL, 66.6 mmol) is added to a solution of 3,5-dimethyl-4-bromobenzyloxyphenol (3.6 g, 12.37 mmol), $Pd(OAc)_2$ (280 mg, 1.247 mmol), $P(o-tol)_3$ (750 mg, 2.464 mmol) and DIPEA (6 mL, 34.4 mmol) in EtCN (50 mL, HPLC grade). The mixture is warmed to 95° C. and stirred at that temperature for 36 h. It is allowed to reach r.t., filtered trough Celite and partitioned between EtOAc and $H_2O$. The organic layer is dried, filtered and concentrated, and the resulting crude is flash chromatographed on $SiO_2$ (2% EtOAc/hexanes) to afford 2.59 g of the Heck product (68%, white solid).

Step C

4-hydroxy-2,6 dimethyl-dihydro-ethyl cinnamate

Palladium (1 g, 10% on activated carbon, 0.94 mmol) is added to a solution of the benzyloxyphenol obtained in Step B (2.5 g, 8.012 mmol), and the mixture is stirred under $H_2$ atmosphere ($H_2$ balloon) overnight. The mixture is filtered trough Celite, and the solvent is removed. The crude residue is flash chromatographed on $SiO_2$ (10% EtOAc/hexanes) to afford 1.4 g of the title compound (79%, white solid).

Preparation 34

2-(4-Hydroxy-2-methyl-phenyl)-cyclopropanecarboxylic acid ethyl ester

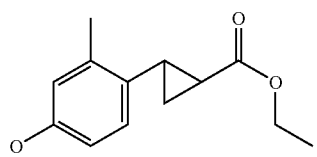

A solution of 2-(4-benzyloxy-2-methyl-phenyl)-cyclopropanecarboxylic acid ethyl ester (2.0 g, 6.75 mmol) in EtOAc (100 mL) is treated with 10% Palladium on carbon (0.5 g) and stirred under hydrogen (1 atm). The reaction stirred for 3 hours. The reaction is filtered through celite, and the filtrate is concentrated to afford 1.3 g (94%) of title compound. $^1H$ NMR (400 MHz, $CDCl_3$); MS ($ES^+$) m/z mass calcd for $C_{20}H_{22}O_3$ 310, found 311 (M+1, 100%).

Preparation 35

(6-Hydroxy-benzo[b]thiophen-3-yl)-acetic acid ethyl ester

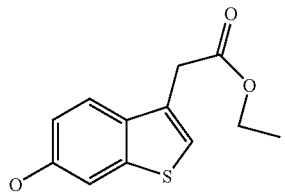

Step A

4-(3-Methoxy-phenylsulfanyl)-3-oxo-butyric acid ethyl ester

Ethyl 4-chloroacetoacetate (32.6 g, 0.188 mol), 3-methoxythiophenol (25.1 g, 0.179 mol) and DMF (700 mL) are combined and degassed by bubbling nitrogen through the stirred mixture for about 10 min, then potassium carbonate (50 g, 0.36 mol) is added to the stirred mixture in one batch. This mixture is stirred under nitrogen at room temperature for 2 h, the mixture is filtered to remove potassium carbonate, then diluted with ethyl acetate. The resulting solution is washed with water, then 5% aq. NaCl. The combined organics are washed with brine, dried over $Na_2SO_4$. Concentration yields the title compound as yellow liquid. This material is used without purification.

Step B

(6-Methoxy-benzo[b]thiophen-3-yl)-acetic acid ethyl ester 4-(3-Methoxy-phenylsulfanyl)-3-oxo-butyric acid ethyl ester (10.0 g) is added to pre-cooled methanesulfonic acid (60 mL) at 0~5° C., then the reaction mixture is allowed to warm to room temperature. After 1 h, the mixture is diluted with ice water and extracted with ethyl acetate. The combined organics are washed with brine, dried over $Na_2SO_4$, concentrated. Chromatography on silica gel eluted with hexanes and ethyl acetate yields (6-methoxy-benzo[b]thiophen-3-yl)-acetic acid ethyl ester (4.8 g) and (4-methoxy-benzo[b]thiophen-3-yl)-acetic acid ethyl ester (0.8 g)

Step C (6-hydroxy-benzo[b]thiophen-3-yl)-acetic acid ethyl ester

To a solution of (6-Methoxy-benzo[b]thiophen-3-yl)-acetic acid ethyl ester (2.4 g, 9.6 mmol) in methylene chloride (60 mL) is added BBr3 (1.0 M, heptane, 29.4 mL, 29.4 mmol) at −20~−30° C. The reaction mixture is allowed to warm to room temperature over 2 hrs, and TLC indicated clean conversion. The reaction is quenched by ice water, extracted with methylene chloride, dried over sodium sulfate, concentrated. Column chromatography on silica gel eluted with hexanes/ethyl acetate yields the title compound (2.2 g).

Preparation 36

(4-Hydroxy-benzo[b]thiophen-3-yl)-acetic acid ethyl ester

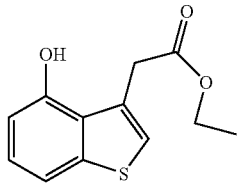

To a solution of (4-Methoxy-benzo[b]thiophen-3-yl)-acetic acid ethyl ester (0.7 g, 2.8 mmol) in methylene chloride (18 mL) is added BBr3 (1.0 M, heptane, 8.6 mL, 8.6 mmol) at −20~−30° C. The reaction mixture is allowed to warm to room temperature over 2 hrs, and TLC indicated clean conversion. The reaction is quenched by ice water, extracted with methylene chloride, dried over sodium sulfate, concentrated. Column chromatography on silica gel eluted with hexanes/ethyl acetate yields the title compound (0.4 g).

Preparation 37

(6-Hydroxy-benzofuran-3-yl)-acetic acid methyl ester

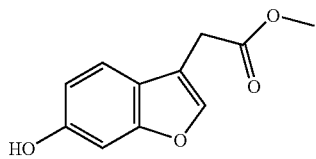

A mixture of 6-hydroxy-(2H)-benzofuran-3-one (5.0 g, 33.3 mmol), methyl (triphenylphosphoranylidene)acetate (25.0 g, 73 mmol), and xylenes (100 mL) is refluxed 6 hr. The reaction is concentrated and diluted with enough 1M aqueous hydrochloric acid to adjust pH to 2-3. The product is extracted into ethyl acetate (3× 100 mL). The combined extracts are dried over anhydrous magnesium sulfate, filtered and concentrated. The residue is purified via silica chromatography eluting with 7:3 hexanes:ethyl acetate to afford the product as a orange oil, 1.3 g, 20%. MS M++1 207. The structure is confirmed by $^1$H NMR spectroscopy.

The following compound is made in a similar manner:

Preparation 38

2-(6-Hydroxy-benzofuran-3-yl)-propionic acid methyl ester

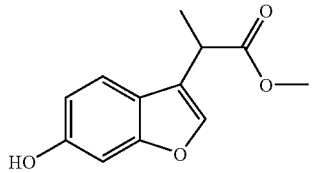

An orange oil. MS M++1 221. The structure is confirmed by $^1$H NMR spectroscopy.

Preparation 39

(6-Mercapto-benzo[b]thiophen-3-yl)-acetic acid ethyl ester

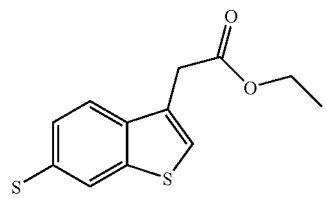

This compound was made from the corresponding phenol analog.

Example 1

2-Methyl-4-[2-(4-trifluoromethylphenyl)-2H-indazol-7-ylmethylsulfanyl]phenoxyacetic Acid

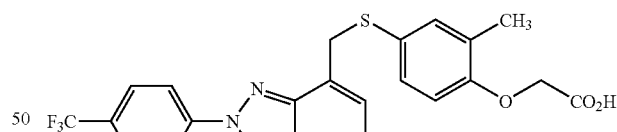

Step A

2-Bromo-1-bromomethyl-3-methylbenzene

Heat a mixture of commercially available 2-bromo-m-xylene (18.50 g, 0.100 mol), phenylperbenzoic acid anhydride (1.21 g, 0.005 mmol) and N-bromosuccinimide (17.10 g, 0.095 mol) in carbon tetrachloride (300 mL) at reflux under nitrogen for 10 h. Dilute the cooled mixture with hexanes (200 mL) and vacuum filter through short plug of silica gel, eluting with hexanes (3× 50 mL). Remove the solvent under reduced pressure and purify the residue by flash column chromatography on silica gel, eluting with hexanes, to provide 2-bromo-1-bromomethyl-3-methylbenzene (1A) as white solid (12.25 g, 46%):

$^1$H NMR (CDCl$_3$) δ 2.43 (s, 3H), 4.64 (s, 2H), 7.10-7.20 (m, 2H), 7.26 (dd, 1H).

Step B

N-(2-Bromo-3-methylbenzyl)-N-(4-trifluoromethylphenyl)hydrazine

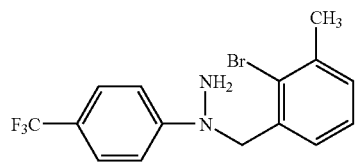

Procedure A. Add a solution of NaHDMS (31.60 mL, 31.60 mmol, 1 M solution in THF) dropwise to a solution of commercially available 4-(trifluoromethyl)phenylhydrazine (5.06 g, 28.73 mmol) in anhydrous THF at 0° C. under nitrogen. Stir for 10 min, warm the mixture to room temperature and stir for an additional 1 h. Cool the mixture to 0° C. and add a solution of 2-bromo-1-bromomethyl-3-methyl-benzene (7.58 g, 28.72 mmol) in THF (15 mL) to the mixture dropwise. Warm the mixture to room temperature and stir for 13 h, cool the mixture to 0° C. and dilute with water (250 mL). Extract the mixture with methylene chloride (1× 250 mL, 2× 150 mL), dry the combined organic extracts over Na$_2$SO$_4$ and remove the solvent under reduced pressure. Purify the residue by flash column chromatography on silica gel, eluting with diethyl ether/hexanes (1:9), to provide N-(2-bromo-3-methylbenzyl)-N-(4-trifluoromethylphenyl)hydrazine as a brown oil (1.75 g, 17%): $^1$H NMR (CDCl$_3$) δ 2.46 (s, 3H), 3.81 (s, 2H), 4.78 (s, 2H), 6.95 (m, 1H), 7.02 (d, 2H), 7.10-7.25 (m, 2H), 7.45 (d, 2H).

Procedure B. Add a solution of commercially available 4-(trifluoromethyl)phenylhydrazine (20.40 g, 0.116 mol) in DMF (100 mL) dropwise over 30 min to a suspension of sodium hydride (3.34 g, 0.139 mol) in anhydrous DMF (150 mL) at −40° C. under nitrogen. Stir the mixture for 30 min and add a solution of 2-bromo-1-bromomethyl-3-methylbenzene (26.30 g, 100 mmol) in THF (50 mL). Stir the mixture at −40° C. for an additional 30 min, warm to −10° C. and stir for an additional 1 h. Dilute the mixture carefully with water (20 mL), warm the mixture to room temperature and dilute with additional water (800 mL). Extract the mixture with diethyl ether (4× 300 mL), wash the combined organic extracts with brine (300 mL) and dry over Na$_2$SO$_4$. Remove the solvent under reduced pressure and purify the residue by flash column chromatography on silica gel, eluting with diethyl ether/hexanes (1:9), to provide N-(2-bromo-3-methylbenzyl)-N-(4-trifluoromethylphenyl)hydrazine as a brown oil (25.59 g, 71%).

Step C

7-Methyl-2-(4-trifluoromethylphenyl)-2H-indazole

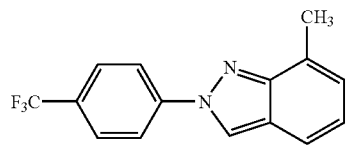

Heat a degassed mixture of N-(2-bromo-3-methylbenzyl)-N-(4-trifluoromethylphenyl)hydrazine (1.72 g, 4.79 mmol), palladium(II) acetate (0.055 g, 0.245 mmol), 1,1'-bis(diphenylphosphino)ferrocene (dppf, 0.196 g, 354 mmol) and sodium tert-butoxide (0.690 g, 7.18 mmol) in anhydrous toluene (15 mL) at 90° C. under nitrogen for 18 h. Cool the mixture to 0° C., treat with water (30 mL) and extract with methylene chloride (1× 50 mL, 2× 30 mL). Dry the combined organic extracts over Na$_2$SO$_4$ and remove the solvent under reduced pressure. Purify the residue by flash column chromatography on silica gel, eluting with diethyl ether/hexanes (1:19), to provide 7-methyl-2-(4-trifluoromethylphenyl)-2H-indazole as a pale yellow solid (395 mg, 30%): $^1$H NMR (CDCl$_3$) δ 2.67 (s, 3H), 7.00-7.15 (m, 2H), 7.53 (d, 1H), 7.78 (d, 2H), 8.07 (d, 2H), 8.43 (s, 1H); APCI MS m/z 277 [C$_{15}$H$_{11}$F$_3$N$_2$+H]$^+$.

Step D

7-Bromomethyl-2-(4-trifluoromethylphenyl)-2H-indazole

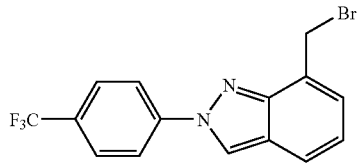

Heat a mixture of 7-methyl-2-(4-trifluoromethylphenyl)-2H-indazole (376 mg, 1.36 mmol), N-bromosuccinimide (255 mg, 1.43 mmol) and phenylperbenzoic acid anhydride (15 mg, 0.062 mmol) in carbon tetrachloride (50 mL) at reflux under nitrogen for 3.5 h. Treat the cooled mixture with silica gel (2 g) and remove the solvent was removed under reduced pressure. Purify the supported residue by flash column chromatography on silica gel, eluting with diethyl ether/hexanes (1:9), to provide 7-bromomethyl-2-(4-trifluoromethylphenyl)-2H-indazole as a white solid (298 mg, 62%):

$^1$H NMR (CDCl$_3$) δ 4.99 (s, 2H), 7.10 (dd, 1H), 7.39 (d, 1H), 7.69 (d, 1H), 7.80 (d, 2H), 8.11 (d, 2H), 8.51 (s, 1H); APCI MS m/z 355 [C$_{15}$H$_{10}$F$_3$BrN$_2$+H]$^+$.

Step E

Ethyl 2-Methyl-4-[2-(4-trifluoromethylphenyl)-2H-indazol-7-yl-methylsulfanyl]phenoxyacetate

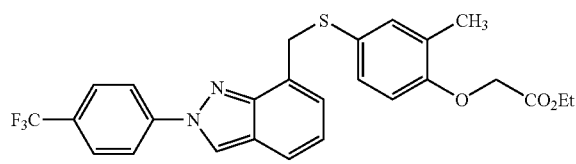

Add cesium carbonate (160 mg, 0.491 mmol) to a degassed mixture of 7-bromomethyl-2-(4-trifluoromethylphenyl)-2H-indazole (85 mg, 0.239 mmol) and ethyl (4-mercapto-2-methylphenoxy)acetate (108 mg, 0.477 mmol) in acetonitrile (10 mL) at room temperature under nitrogen and stir the mixture for 12 h. Filter the mixture through a plug of silica gel, eluting with ethyl acetate (3× 20 mL) and remove the solvents under reduced pressure. Purify the residue by flash column chromatography on silica gel, eluting with ethyl acetate/hexanes (1:9), to provide ethyl 2-methyl-4-[2-(4-trifluoromethylphenyl)-2H-indazol-7-yl-methylsulfanyl]phenoxyacetate as a white solid (85 mg, 71%): $^1$H NMR (CDCl$_3$) δ 1.29 (t, 3H), 2.23 (s, 3H), 4.25 (q, 2H), 4.48 (s, 2H), 4.59 (s, 2H), 6.58 (d, 1H), 6.95-7.08 (m, 2H), 7.17 (dd, 1H), 7.24 (m, 1H), 7.58 (dd, 1H), 7.79 (d, 2H), 8.03 (d, 2H), 8.46 (s, 1H).

Step F

2-Methyl-4-[2-(4-trifluoromethylphenyl)-2H-indazol-7-ylmethylsulfanyl]phenoxyacetic Acid

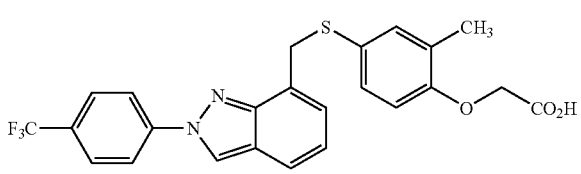

Add a solution of sodium hydroxide (1.0 mL, 1.00 mmol, 1 M) to a solution of ethyl 2-methyl-4-[2-(4-trifluoromethylphenyl)-2H-indazol-7-yl-methylsulfanyl]phenoxyacetate (80 mg, 0.160 mmol) in methanol (5.0 mL) and methylene chloride (2.0 mL) at room temperature under nitrogen and stir the mixture for 1 h. Cool the mixture to 0° C. and add 1 N HCl (1.3 mL) dropwise. Dilute the mixture with water (10 mL) and extract with methylene chloride (60 mL). Dry the organic extract over Na$_2$SO$_4$ and remove the solvent under reduced pressure to provide 2-methyl-4-[2-(4-trifluoromethylphenyl)-2H-indazol-7-ylmethylsulfanyl]phenoxyacetic acid as a white solid (69 mg, 91%): mp 79-81° C.; $^1$H NMR (CDCl$_3$) δ 2.22 (s, 3H), 4.48 (s, 2H), 4.63 (s, 2H), 6.60 (d, 1H), 6.96-7.10 (m, 2H), 7.17 (dd, 1H), 7.25 (m, 1H), 7.58 (d, 1H), 7.78 (d, 2H), 8.06 (d, 2H), 8.46 (s, 1H); APCI MS m/z 471 [C$_{24}$H$_{19}$F$_3$N$_2$O$_3$S−H]$^-$. HPLC analysis (retention time=12.54 min) showed one peak, with a total purity of 98.5% (area percent).

Prepare examples 2-7 by a similar method used to prepare example 1.

Example 2

3-{2-Methyl-4-[2-(4-trifluoromethylphenyl)-2H-indazol-7-ylmethylsulfanyl]phenyl}propionic Acid

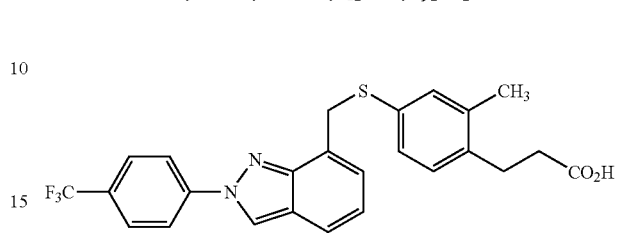

mp 88-90° C.; $^1$H NMR (CDCl$_3$) δ 2.26 (s, 3H), 2.60 (t, 2H), 2.90 (t, 2H), 4.57 (s, 2H), 7.00-7.07 (m, 2H), 7.14-7.24 (m, 3H), 7.59 (d, 1H), 7.79 (d, 2H), 8.08 (d, 2H), 8.46 (s, 1H); APCI MS m/z 469 [C$_{25}$H$_{21}$F$_3$N$_2$O$_2$S−H]$^-$. HPLC analysis (retention time=12.87 min) showed one peak, with a total purity of 96.8% (area percent).

Example 3

2-Ethyl-4-[2-(4-trifluoromethylphenyl)-2H-indazol-7-ylmethylsulfanyl]phenoxyacetic Acid

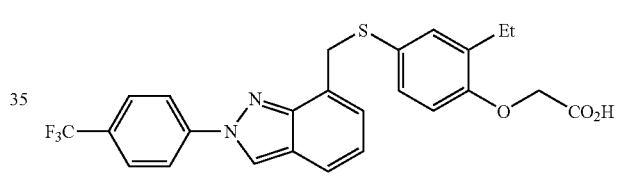

mp 159-161° C.; $^1$H NMR (CDCl$_3$) δ 1.14 (t, 3H0, 2.62 (q, 2H), 4.48 (s, 2H), 4.63 (s, 2H), 6.62 (d, 1H), 6.92-7.12 (m, 2H), 7.14-7.30 (m, 2H), 7.58 (d, 1H), 7.78 (d, 2H), 8.06 (d, 2H), 8.45 (s, 1H); APCI MS m/z 485 [C$_{25}$H$_{21}$F$_3$N$_2$O$_3$S−H]$^-$. HPLC analysis (retention time=13.21 min) showed one peak, with a total purity of 97.5% (area percent).

Example 4

3-[2-(4-Trifluoromethylphenyl)-2H-indazol-7-ylmethylsulfanyl]phenylacetic Acid

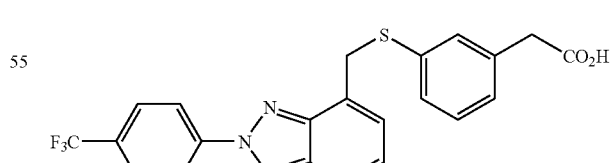

mp 147-149° C.; $^1$H NMR (CDCl$_3$) δ 3.57 (s, 2H), 4.59 (s, 2H), 7.00 (dd, 1H0, 7.10 (d, 1H), 7.13-7.27 (m, 2H), 7.32 (s, 1H), 7.34 (m, 1H), 7.56 (d, 1H), 7.77 (d, 2H), 8.05 (d, 2H), 8.43 (s, 1H); APCI MS m/z 441 [C$_{23}$H$_{17}$F$_3$N$_2$O$_2$S−H]$^-$. HPLC analysis (retention time=11.95 min) showed one peak, with a total purity of 98.9% (area percent).

Example 5

6-[2-(4-Trifluoromethylphenyl)-2H-indazol-7-ylmethylsulfanyl]benzo[b]thiophen-3-ylacetic Acid

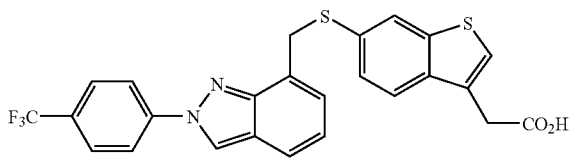

mp 141-143° C.; $^1$H NMR (CDCl$_3$) δ 3.84 (s, 2H), 4.62 (s, 2H), 7.00 (dd, 1H), 7.18 (d, 1H), 7.31 (s, 1H), 7.42 (dd, 1H), 7.53-7.61 (m, 2H), 7.75 (d, 2H), 7.93 (d, 1H), 8.00 (d, 2H), 8.42 (s, 1H); APCI MS m/z 497 [C$_{25}$H$_{17}$F$_3$N$_2$O$_2$S$_2$–H]$^-$. HPLC analysis (retention time=12.9 min) showed one peak, with a total purity of 96.3% (area percent).

Example 6

3-{2-Methyl-4-[2-(4-trifluoromethylphenyl)-2H-indazol-7-ylmethoxy]phenyl}propionic Acid

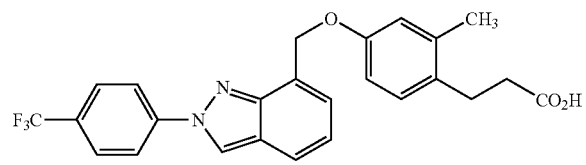

mp 133-135° C.; $^1$H NMR (DMSO-d$_6$) δ 2.25 (s, 3H), 2.45 (m, 2H), 2.75 (t, 2H), 5.46 (s, 2H), 6.83 (dd, 1H), 6.91 (d, 1H), 7.07 (d, 1H), 7.15 (dd, 1H), 7.41 (d, 1H), 7.76 (d, 1H), 7.98 (d, 2H), 8.36 (d, 2H), 9.30 (s, 1H), 12.11 (s, 1H); APCI MS m/z 453 [C$_{25}$H$_{21}$F$_3$N$_2$O$_3$–H]$^-$. HPLC analysis (retention time=12.19 min) showed one peak, with a total purity of 97.4% (area percent).

Example 7

3-{2-Ethyl-4-[2-(4-trifluoromethylphenyl)-2H-indazol-7-ylmethoxy]phenol}propionic Acid

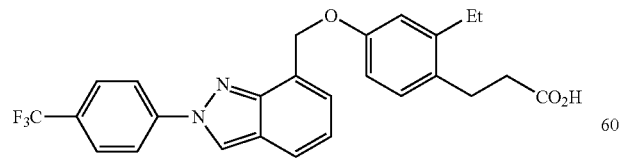

mp 157-159° C.; $^1$H NMR (DMSO-d$_6$) δ 1.13 (t, 3H), 2.40-2.65 (m, 4H), 2.77 (t, 2H), 5.46 (s, 2H), 6.82 (dd, 1H), 6.89 (d, 1H), 7.08 (d, 1H), 7.15 (dd, 1H), 7.42 (d, 1H), 7.77 (d, 1H), 7.98 (d, 2H), 8.36 (d, 2H), 9.30 (s, 1H); APCI MS m/z 467 [C$_{26}$H$_{23}$F$_3$N$_2$O$_3$–H]$^-$. HPLC analysis (retention time=12.7 min) showed one peak, with a total purity of >99% (area percent).

Example 8

(+/−)-2-Methyl-4-{1-[2-(4-trifluoromethylphenyl)-2H-indazol-7-yl]ethylsulfanyl}phenoxyacetic Acid

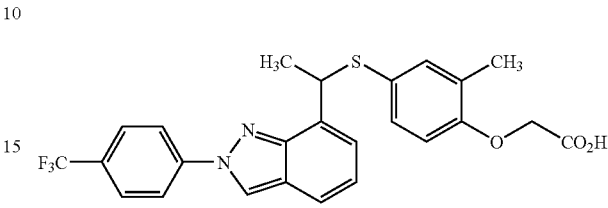

Step A 2-(4-Trifluoromethylphenyl)-2H-indazole-7-carbaldehyde

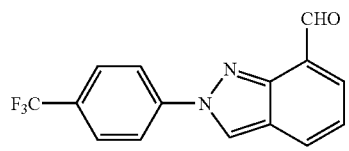

Add 4 Å molecular sieves (1.00 g) to a solution of N-methylmorpholine oxide (NMO, 53 mg, 0.45 mmol) in acetonitrile (2 mL) at room temperature under nitrogen and stir the mixture for 30 min. Add a solution of 7-bromomethyl-2-(4-trifluoromethylphenyl)-2H-indazole (106 mg, 0.300 mmol) in acetonitrile (1 mL) and stir the reaction mixture for 1 h. Filter the mixture through a plug of Celite, washing the residue with ethyl acetate (3× 30 mL). Wash the combined organic extracts with 1 N HCl (20 mL) and brine (2× 20 mL), dry over MgSO$_4$ and remove the solvents under reduced pressure to provide 2-(4-trifluoromethylphenyl)-2H-indazole-7-carbaldehyde as a yellow solid (65 mg, 75%): $^1$H NMR (CDCl$_3$) δ 7.32 (dd, 1H), 7.83 (d, 2H), 7.97 (d, 1H), 8.04 (d, 1H), 8.15 (d, 2H), 8.63 (s, 1H), 10.65 (s, 1H); APCI MS m/z 291 [C$_{15}$H$_9$F$_3$N$_2$O+H]$^+$.

Step B (+/−)-1-[2-(4-Trifluoromethylphenyl)-2H-indazol-7-yl]ethanol

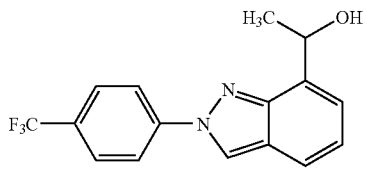

Add a solution of methylmagnesium bromide (2.80 mL, 40 mmol, 3.0 M in diethyl ether) dropwise over 5 min to a solution of 2-(4-trifluoromethylphenyl)2H-indazole-7-carbaldehyde (1A, 1.56 g, 5.37 mmol) in anhydrous THF (30 mL) at −40° C. under nitrogen and stir for 30 min. Dilute the mixture with saturated NH$_4$Cl solution (25 ml), warm the mixture to room temperature and dilute with ethyl acetate (350 mL). Wash the organic phase with water (50 mL) and brine (100 mL), dry over Na$_2$SO$_4$ and remove the solvents under reduced pressure. Purify the residue by flash column chromatography on silica gel, eluting with ethyl acetate/hexanes (1:4), to provide 1-[2-(4-trifluoromethylphenyl)-2H-indazol-7-yl]ethanol (1B) as a yellow solid (1.23 g, 75%): $^1$H NMR (CDCl$_3$) δ 1.76 (d, 3H), 3.67 (d, 1H), 5.39 (m, 1H), 7.11 (dd, 1H), 7.25 (d, 1H), 7.62 (d, 1H), 7.80 (d, 2H), 8.06 (d, 2H), 8.49 (s, 1H).

Step C (+/−)-Ethyl 2-Methyl-4-{1-[2-(4-trifluoromethylphenyl)-2H-indazol-7-yl]ethoxy}phenoxyacetate

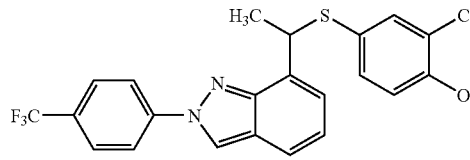

Add tri-n-butylphosphine (0.20 mL, 1.45 mmol) dropwise by syringe to a solution of 1-[2-(4-trifluoromethylphenyl)-2H-indazole-7-yl]ethanol (169 mg, 0.552 mmol), ethyl 4-mercapto-2-methylphenoxyacetate (187 mg, 0.826 mmol) and 1,1'-(azodicarbonyl)dipiperidine (ADDP, 279 mg, 1.11 mmol) in anhydrous toluene (10 mL) at −25° C. under argon and stir the mixture for 1 h. Warm the mixture to room temperature, stir the mixture for an additional 5 h and dilute the mixture with methylene chloride (50 mL). Treat the mixture with silica gel (2 g), remove the solvents under reduced pressure and purify the residue by flash column chromatography on silica gel, eluting with ethyl acetate/hexanes (1:9), to provide ethyl 2-methyl-4-{1-[2-(4-trifluoromethylphenyl)-2H-indazol-7-yl]ethoxy}phenoxyacetate as a pale yellow viscous oil (190 mg, 67%): $^1$H NMR (DMSO-d$_6$) δ 1.19 (t, 3H), 1.72 (d, 3H), 2.11 (s, 3H), 4.14 (q, 2H), 4.74 (s, 2H), 4.98 (m, 1H), 6.76 (d, 1H), 7.07 (dd, 1H), 7.12-7.25 (m, 3H), 7.66 (d, 1H), 7.99 (d, 2H), 8.34 (d, 2H), 9.24 (s, 1H).

Step D (+/−)-2-Methyl-4-{1-[2-(4-trifluoromethylphenyl)-2H-indazol-7-yl]ethylsulfanyl}phenoxyacetic Acid

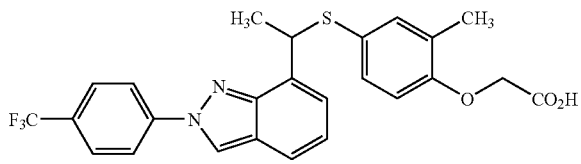

Add a 1 N solution of sodium hydroxide (1.45 mL, 1.45 mol) to a solution of ethyl 2-methyl-4-{1-[2-(4-trifluoromethylphenyl)-2H-indazol-7-yl] ethylsulfanyl}phenoxyacetate (1C, x g, x mmol) in methanol (4.0 mL) and methylene chloride (3.0 mL) at room temperature and heat the mixture at 40° C. for 2 h. Cool the mixture to 0° C., dilute with 1 N HCl (1.50 mL) and water (20 mL) and extract with methylene chloride (60 mL). Dry the organic phase over MgSO$_4$, remove the solvents under reduced pressure and purify the residue by flash column chromatography on silica gel, eluting with methanol:methylene chloride (1:19), to provide the product as a viscous oil. Triturate the residue with hexanes and collect the solids by vacuum filtration to provide 2-methyl-4-{1-[2-(4-trifluoromethylphenyl)-2H-indazol-7-yl]ethylsulfanyl}phenoxyacetic acid as a white solid (133 mg, 76%): mp 62-64° C.; $^1$H NMR (DMSO-d$_6$) δ 1.72 (d, 3H), 2.11 (s, 3H), 4.64 (s, 2H), 4.97 (q, 1H), 6.75 (d, 1H), 7.07 (dd, 1H), 7.10-7.23 (m, 3H), 7.65 (d, 1H), 7.99 (d, 2H), 8.35 (d, 2H), 9.24 (s, 1H), 12.95 (bs, 1H); APCI MS m/z 485 [C$_{25}$H$_{21}$F$_3$N$_2$O$_3$S−H]$^-$. HPLC analysis (retention time=13.33 min) showed one peak, with a total purity of 96.3% (area percent).

Prepare examples 9-13 by a similar method used to prepare example 8.

Example 9

(+/−)-3-(2-Methyl-4-{1-[2-(4-trifluoromethylphenyl)-2H-indazol-7-yl]ethylsulfanyl}phenyl)propionic Acid mp 59-61° C.; $^1$H NMR (DMSO-d$_6$) δ 1.75 (d, 3H), 2.18 (s, 3H), 2.42 (t, 2H), 2.73 (t, 2H), 5.11 (q, 1H), 7.03-7.20 (m, 4H), 7.30 (d, 1H), 7.67 (d, 1H), 8.00 (d, 2H), 8.36 (d, 2H), 9.25 (s, 1H), 12.11 (bs, 1H); APCI MS m/z 483 [C$_{26}$H$_{23}$F$_3$N$_2$O$_2$S−H]$^-$. HPLC analysis (retention time=13.66 min) showed one peak, with a total purity of 97.7% (area percent).

Example 10

(+/−)-2-Ethyl-4-{1-[2-(4-trifluoromethylphenyl)-2H-indazol-7-yl]ethylsulfanyl}phenoxyacetic Acid mp 65-67° C.; $^1$H NMR (DMSO-d$_6$) δ 1.02 (t, 3H), 1.72 (d, 3H), 2.48 (t, 2H), 4.64 (s, 2H), 4.98 (q, 1H), 6.76 (d, 1H), 7.03-7.10 (m, 2H), 7.11-7.21 (m, 2H), 7.66 (dd, 1H), 7.99 (d, 2H), 8.34 (d, 2H), 9.24 (s, 1H), 12.92 (bs, 1H); APCI MS m/z 499 [$C_{26}H_{23}F_3N_2O_3S$–H]⁻. HPLC analysis (retention time=14.04 min) showed one peak, with a total purity of 98.7% (area percent).

Example 11

(+/−)-6-{1-[2-(4-Trifluoromethylphenyl)-2H-indazol-7-yl]ethylsulfanyl}benzo[b]thiophen-3-ylacetic Acid

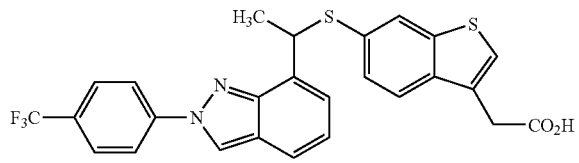

mp 76-78° C.; ¹H NMR (DMSO-$d_6$) δ 1.80 (d, 3H), 3.79 (s, 2H), 5.22 (q, 1H), 7.07 (dd, 1H), 7.32 (d, 1H), 7.43 (d, 1H), 7.55 (s, 1H), 7.68 (d, 2H), 8.02 (d, 2H), 8.04 (s, 1H), 8.34 (d, 2H), 9.26 (s, 1H), 12.44 (bs, 1H); APCI MS m/z 511 [$C_{26}H_{19}F_3N_2O_2S_2$–H]⁻. HPLC analysis (retention time=13.91 min) showed one peak, with a total purity of 96.7% (area percent).

Example 12

(+/−)-3-(2-Methyl-4{1-[2-(4-trifluoromethylphenyl)-2H-indazol-7yl]ethoxy}phenyl)propionic Acid

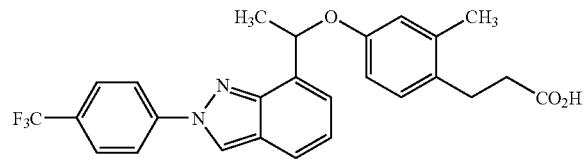

mp 66-68° C.; ¹H NMR (DMSO-$d_6$) δ 1.74 (d, 3H), 2.15 (s, 3H), 2.37 (t, 2H), 2.66 (t, 2H), 6.00 (q, 1H), 6.63 (dd, 1H), 6.79 (d, 1H), 6.93 (d, 1H), 7.09 (dd, 1H), 7.29 (d, 1H), 7.69 (d, 1H), 8.00 (d, 2H), 8.38 (d, 2H), 9.28 (s, 1H), 12.04 (bs, 1H); APCI MS m/z 467 [$C_{26}H_{23}F_3N_2O_3$–H]⁻. HPLC analysis (retention time=12.87 min) showed one peak, with a total purity of 95.3% (area percent).

Example 13

(+/−)-3-(2-Ethyl-4-{1-[2-(4-trifluoromethylphenyl)-2H-indazol-7-yl]ethoxyphenyl)propionic Acid

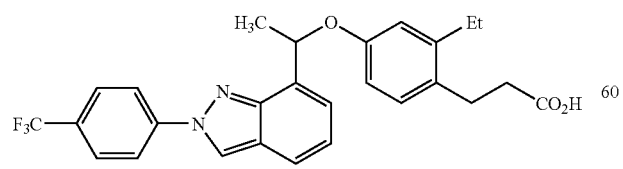

mp 61-63° C.; ¹H NMR (DMSO-$d_6$) δ 1.00 (t, 3H), 1.75 (d, 3H), 2.37 (t, 2H), 2.44 (t, 2H), 2.68 (t, 2H), 6.02 (q, 1H), 6.63 (dd, 1H), 6.80 (s, 1H), 6.94 (d, 1H), 7.09 (dd, 1H), 7.31 (d, 1H), 7.69 (dd, 1H), 8.00 (d, 2H), 8.39 (d, 2H), 9.28 (s, 1H), 12.12 (bs, 1H); APCI MS m/z 481 [$C_{27}H_{25}F_3N_2O_3$–H]⁻. HPLC analysis (retention time=13.66 min) showed one peak, with a total purity of 97.3% (area percent).

Example 14

2-Methyl-4-{1-methyl-1-[2-(4-trifluoromethylphenyl)-2H-indazol-7-yl]ethylsulfanyl}phenoxyacetic Acid

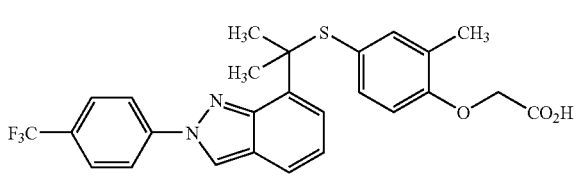

Step A

Methyl 3-Methyl-2-nitrobenzoate

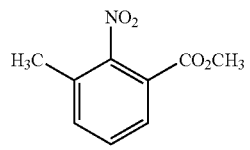

Add acetyl chloride (20 mL) dropwise to a suspension of commercially available 3-methyl-2-nitro-benzoic acid (13.45 g, 74.25 mmol) in methanol (200 mL) at 0° C., heat to reflux and stir for 20 h. Remove the solvents under reduced pressure and dissolve the residue in ethyl acetate (800 mL). Wash with saturated aqueous NaHCO₃ solution (200 mL) and brine (150 mL), dry over Na₂SO₄ and remove the solvents under reduced pressure to provide methyl 3-methyl-2-nitrobenzoate as a white solid (12.35 g, 85%): ¹H NMR (CDCl₃) δ 2.36 (s, 3H), 3.89 (s, 3H), 7.40-7.51 (m, 2H), 7.84 (m, 1H).

Step B

Methyl 3-Bromomethyl-2-nitrobenzoate

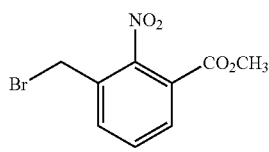

Heat a mixture of methyl 3-methyl-2-nitrobenzoate (12.34 g, 63.23 mmol), benzoyl peroxide (0.920 g, 3.80 mmol) and N-bromosuccinimide (11.25 g, 63.21 mmol) in carbon tetrachloride (330 mL) at reflux under nitrogen for 12 h. Dilute the cooled mixture with methylene chloride (150 mL), treat with silica gel (30 g) and remove the solvents under reduced pressure. Purify the residue by flash column chromatography on silica gel, eluting with ethyl acetate/hexanes (15:85), to provide methyl 3-bromomethyl-2-nitrobenzoate (1B) as a pale yellow solid (7.15 g, 41%): $^1$H NMR (CDCl$_3$) δ 3.91 (s, 3H), 4.46 (s, 2H), 7.58 (t, 1H), 7.74 (dd, 1H), 7.96 (dd, 1H).

Step C

Methyl 3-Formyl-2-nitrobenzoate

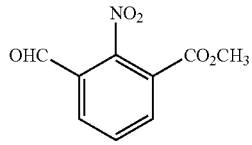

Add N-methylmorpholine oxide (NMO, 6.10 g, 52.07 mmol) to a mixture of methyl 3-bromomethyl-2-nitrobenzoate (7.13 g, 26.023 mmol) and 4 Å molecular sieves (35.32 g) in acetonitrile (150 mL)=at room temperature under nitrogen and stir for 1.5 h. Dilute the mixture with ethyl acetate (600 mL), filter the mixture by vacuum filtration and wash the filtrate with water (100 mL), 1 N HCl (100 mL) and brine (150 mL) and dry over Na$_2$SO$_4$. Remove the solvents under reduced pressure and purify the residue by flash column chromatography on silica gel, eluting with ethyl acetate/hexanes (1:3), to provide methyl 3-formyl-2-nitrobenzoate as an off-white solid (4.04 g, 74%): $^1$H NMR (CDCl$_3$) δ 3.95 (s, 3H), 7.77 (t, 1H), 8.18 (dd, 1H), 8.28 (dd, 1H), 9.98 (s, 1H).

Step D

Methyl 2-Nitro-3[(4-trifluoromethylphenylimino) methyl]benzoate

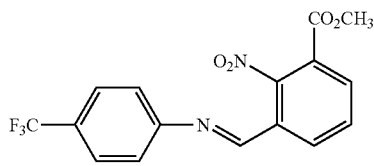

Heat a mixture of methyl 3-formyl-2-nitrobenzoate (4.03 g, 19.27 mmol) and 4-trifluoromethyl-phenylamine (3.26 g, 20.23 mmol) in ethanol (15 mL) at reflux under nitrogen for 2 h and cool the mixture to room temperature. Dilute the mixture with hexanes (75 mL), stir for 2.5 h and collect the solids by vacuum filtration, washing with hexanes (10 mL) to provide methyl 2-nitro-3-[(4-trifluoromethylphenylimino) methyl]benzoate as a white solid (5.35 g, 79%): $^1$H NMR (CDCl$_3$) δ 3.95 (s, 1H), 7.26 (d, 2H), 7.67 (d, 2H), 7.73 (d, 1H), 8.16 (dd, 1H), 8.36 (s, 1H), 8.51 (dd, 1H); APCI MS m/z 353 [C$_{16}$H$_{11}$F$_3$N$_2$O$_4$+H]$^+$.

Step E

Methyl 2-(4-Trifluoromethylphenyl)-2H-indazole-7-carboxylate

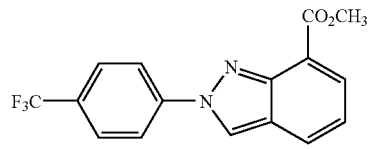

Heat a mixture of methyl 2-nitro-3-[(4-trifluoromethylphenylimino)methyl]benzoate (5.33 g, 15.13 mmol) and sodium azide (1.03 g, 15.84 mmol) in anhydrous DMF (60 mL) at 90° C. under nitrogen for 6 h and cool to room temperature. Dilute the mixture with water (200 mL) and extract with ethyl acetate (3× 200 mL). Wash the combined organic extracts with water (150 mL) and brine (2× 150 mL), dry over Na$_2$SO$_4$ and remove the solvents under reduced pressure. Purify the residue by flash column chromatography on silica gel, eluting with ethyl acetate/hexanes (1:4), to provide methyl 2-(4-trifluoromethylphenyl)-2H-indazole-7-carboxylate as a yellow solid (2.49 g, 51%): $^1$H NMR (CDCl$_3$) δ 4.06 (s, 3H), 7.22 (m, 1H), 7.81 (d, 2H), 7.97 (dd, 1H), 8.10-8.20 (m, 3H), 8.60 (s, 1H); APCI MS m/z 321 [C$_{16}$H$_{11}$F$_3$N$_2$O$_2$+H]$^+$.

Step F

2-[2-(4-Trifluoromethylphenyl)-2H-indazol-7-yl] propan-2-ol

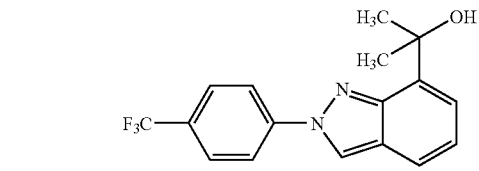

Add methylmagnesium bromide (3 M in diethyl ether, 8.50 mL, 25.50 mmol) dropwise over 10 min to a solution of methyl 2-(4-trifluoromethylphenyl)-2H-indazole-7-carboxylate (2.47 g, 7.71 mmol) in anhydrous THF (60.0 mL) at −25° C. under nitrogen, stir for 3 h and dilute with saturated aqueous NH$_4$Cl solution (150 mL). Extract with ethyl acetate (600 mL), wash with brine (150 mL), dry over MgSO$_4$ and remove the solvents under reduced pressure. Purify the residue by flash column chromatography on silica gel, eluting with ethyl acetate/hexanes (1:3), to provide 2-[2-(4-trifluoromethylphenyl)-2H-indazol-7-yl]propan-2-ol as a pale yellow solid in (1.17 g, 47%): $^1$H NMR (CDCl$_3$) δ 1.80 (s, 6H), 7.10 (dd, 1H), 7.23 (d, 1H), 7.60 (d, 1H), 7.81 (d, 2H), 8.05 (d, 2H), 8.49 (s, 1H).

Step G

Ethyl 2-Methyl-4-{1-methyl-1-[2-(4-trifluoromethylphenyl)-2H-indazol-7-yl]ethylsulfanyl}phenoxyacetate

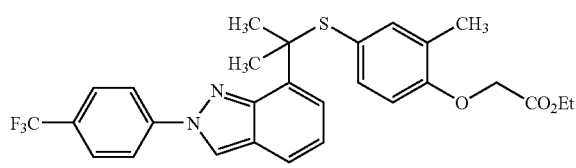

Add zinc(II) iodide (127 mg, 0.398 mmol) to a mixture of 2-[2-(4-trifluoromethylphenyl)-2H-indazol-7-yl]propan-2-ol (128 mg, 0.400 mmol) and ethyl 4-mercapto-2-methylphenoxyacetate (110 mg, 0.486 mmol) in methylene chloride (5 mL) at room temperature under nitrogen and stir for 10 h. Dilute the mixture with ethyl acetate (100 mL), wash with water (30 mL), saturated aqueous NaHCO$_3$ solution (30 mL) and brine (30 mL), dry over MgSO$_4$ and remove the solvents under reduced pressure. Purify the residue by flash column chromatography on silica gel, eluting with ethyl acetate/hexanes (1:9), to provide ethyl 2-methyl-4-{1-methyl-1-[2-(4-trifluoromethylphenyl)-2H-indazol-7-yl]ethylsulfanyl}phenoxyacetate as a pale yellow viscous (128 mg, 61%): $^1$H NMR (CDCl$_3$) δ 1.27 (t, 3H), 1.97(s, 6H), 2.09 (s, 3H), 4.25 (q, 2H), 4.55 (s, 2H), 6.45 (d, 1H), 6.75 (d, 1H), 6.77-6.95 (m, 3H), 7.59 (dd, 1H), 7.78 (d, 2H), 8.12 (d, 2H), 8.50 (s, 1H).

Step H

2-Methyl-4-{1-methyl-1-[2-(4-trifluoromethylphenyl)-2H-indazol-7-yl]ethylsulfanyl}phenoxyacetic Acid

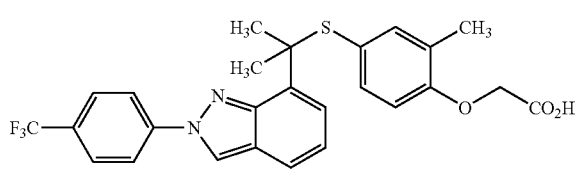

Add a solution of 1 N NaOH (1.00 mL, 1.00 mmol) to a solution of ethyl 2-methyl-4-{1-methyl-1-[2-(4-trifluoromethylphenyl)-2H-indazol-7-yl]ethylsulfanyl}phenoxyacetate (1G, 123 mg, 0.233 mmol) in methanol (3.00 mL) and methylene chloride (3.00 mL) at room temperature and stir for 3.5 h. Dilute the mixture with 1 N HCl (1.20 mL) and water (20 mL) and extract with methylene chloride (60 mL). Dry the organic extract with MgSO$_4$, remove the solvents under reduced pressure and purify the residue by flash column chromatography on silica gel, eluting with methanol/methylene chloride (1:9), to provide 2-methyl-4-{1-methyl-1-[2-(4-trifluoromethylphenyl)-2H-indazol-7-yl]ethylsulfanyl}phenoxyacetic acid as a white solid (61 mg, 53): mp 118-120° C.; $^1$H NMR (DMSO-d$_6$) δ 1.90 (s, 6H), 1.98 (s, 3H), 4.43 (s, 2H), 6.58-6.64 (m, 2H), 6.82 (d, 1H), 6.90-7.00 (m, 2H), 7.69 (d, 1H), 8.00 (d, 2H), 8.37 (d, 2H), 9.27 (s, 1H); APCI MS m/z 499 [C$_{26}$H$_{23}$F$_3$N$_2$O$_3$S−H]$^-$. HPLC analysis (retention time=13.89 min) showed one peak, with a total purity of 97.9% (area percent).

Prepare examples 15-17 by a similar method used to prepare example 14.

Example 15

3-(2-Methyl-4-{1-methyl-1-[2-(4-trifluoromethylphenyl)-2H-indazol-7-yl]ethylsulfanyl}phenyl) propionic Acid

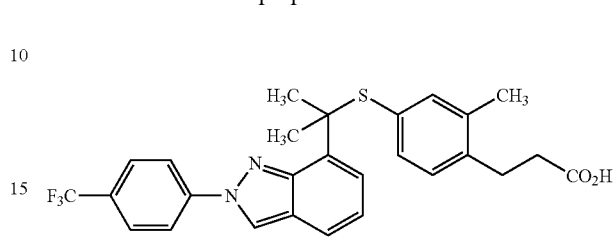

mp 68-70° C.; $^1$H NMR (DMSO-d$_6$) δ 1.92 (s, 6H), 2.08 (s, 3H), 2.40 (t, 2H), 2.71 (t, 2H), 6.71 (s, 1H), 6.79 (d, 1H), 6.94-7.03 (m, 3H), 7.70 (dd, 1H), 8.01 (d, 2H), 8.36 (d, 2H), 9.28 (s, 1H); APCI MS m/z 497 [C$_{27}$H$_{25}$F$_3$N$_2$O$_2$S−H]$^-$. HPLC analysis (retention time=14.71 min) showed one peak, with a total purity of >99% (area percent).

Example 16

2-Ethyl-4-{1-methyl-1-[2-(4-trifluoromethylphenyl)-2H-indazol-7-yl]ethylsulfanyl}phenoxyacetic Acid

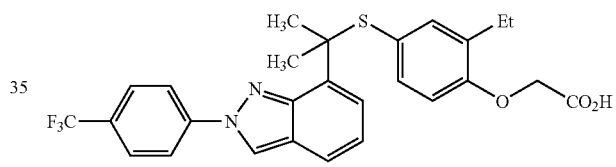

mp 114-116° C.; $^1$H NMR (DMSO-d$_6$) δ 0.92 (t, 3H), 1.90 (s, 6H), 2.36 (q, 2H), 4.47 (s, 2H), 6.48 (d, 1H), 6.64 (d, 1H), 6.85-6.99 (m, 3H), 7.68 (d, 1H), 8.01 (d, 2H), 8.37 (d, 2H), 9.28 (s, 1H); APCI MS m/z 513 [C$_{27}$H$_{25}$F$_3$N$_2$O$_3$S−H]$^-$. HPLC analysis (retention time=14.55 min) showed one peak, with a total purity of 97.6% (area percent).

Example 17

6-{1-Methyl-1-[2-(4-trifluoromethylphenyl)-2H-indazol-7-yl]ethylsulfanyl}benzo[b]thiophen-3-ylacetic Acid

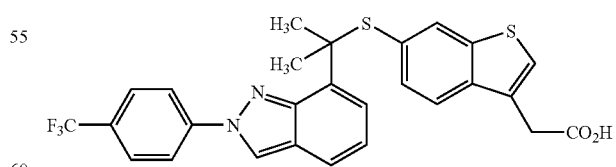

mp 120-122° C.; $^1$H NMR (DMSO-d$_6$) δ 1.96 (s, 6H), 3.76 (s, 2H), 6.94-7.07 (m, 3H), 7.46-7.60 (m, 3H), 7.72 (dd, 1H), 8.00 (d, 2H), 8.36 (d, 2H), 9.29 (s, 1H); APCI MS m/z 525 [C$_{27}$H$_{21}$F$_3$N$_2$O$_2$S$_2$−H]$^-$. HPLC analysis (retention time=14.35 min) showed one peak, with a total purity of 98.7% (area percent).

Example 18

Ethyl 2-Methyl-4-[2-(4-trifluoromethylphenyl)-2H-indazol-6-ylmethylsulfanyl]phenoxyacetic Acid

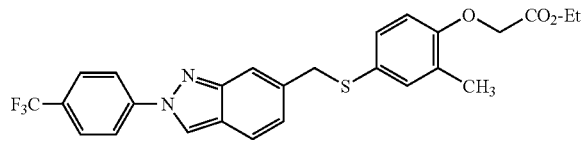

Step A

4-Bromomethyl-3-nitro-benzoic acid methyl ester

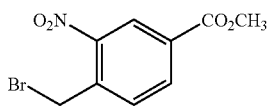

Add acetyl chloride (30.0 mL) dropwise to a solution of commercially available 4-methyl-3-nitro-benzoic acid (18.12 g, 100.0 mmol) in methanol (200 mL) at 0° C. under nitrogen, stir for 1 h, warm to room temperature and stir for 12 h. Remove the solvent under reduced pressure, dilute with ethyl acetate (600 mL), wash with saturated aqueous NaHCO$_3$ solution (3×150 mL) and brine (150 mL) and dry over MgSO$_4$ and remove the solvents under reduced pressure to provide methyl 4-methyl-3-nitrobenzoate (XCH-E-138) as off white solid (18.42 g, 94%). Dilute some of the ester (11.71 g, 60.0 mmol) with carbon tetrachloride (400 mL), treated with benzoyl peroxide (0.872 g, 3.60 mmol) and N-bromosuccinimide (10.68 g, 60.0 mmol) and heat at reflux under nitrogen for 12 h. Treat the mixture with silica gel (40 g), remove the solvents under reduced pressure and purify the residue by flash column chromatography on silica gel, eluting with ethyl acetate/hexanes (1:9), to provide methyl 4-bromomethyl-3-nitrobenzoate as a viscous yellow oil (11.16 g, 68%): $^1$H NMR (CDCl$_3$) δ 3.98 (s, 3H), 4.85 (s, 2H), 7.68 (d, 1H), 8.25 (dd, 1H), 8.66 (d, 1H).

Step B

Methyl 4-Formyl-3-nitrobenzoate

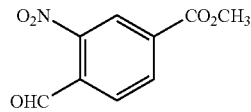

Add N-methylmorpholine oxide (NMO, 5.27 g, 45.0 mmol) to a mixture of methyl 4-bromomethyl-3-nitrobenzoate (8.22 g, 30.0 mmol) and 4 Å molecular sieves (20.05 g) in acetonitrile (150 mL) at room temperature under nitrogen and stir for 40 min. Add additional NMO (1.76 g, 15.02 mmol) and stir for an additional 30 min. Remove the solids by vacuum filtration and dilute the filtrate with ethyl acetate.(600 mL), wash with 1 N HCl (100 mL) and brine (2× 100 mL) and dry over MgSO$_4$. Remove the solvents under reduced pressure and purify the residue by flash column chromatography on silica gel, eluting with ethyl acetate/hexanes (15:85), to provide methyl 4-formyl-3-nitrobenzoate as a white solid (4.15 g, 66%): $^1$H NMR (CDCl$_3$) δ 4.02 (s, 3H), 8.01 (d, 1H), 8.42 (dd, 1H), 8.75 (d, 1H), 10.47 (s, 1H).

Step C

Methyl 3-Nitro-4-[(4-trifluoromethylphenylimino)methyl]benzoate

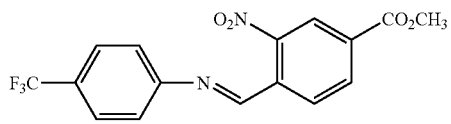

Stir a mixture of methyl 4-formyl-3-nitrobenzoate (4.15 g, 19.84 mmol) and 4-trifluoromethylphenylamine (3.36 g, 20.85 mmol) in ethanol (10 mL) at room temperature under nitrogen for 3 h, dilute the mixture with hexanes (60 mL) and stir for an additional 2 h. Collect the solids by vacuum filtration and wash with hexanes (20 mL) to provide methyl 3-nitro-4-[(4-trifluoromethylphenylimino)methyl]benzoate as a yellow solid (4.45 g, 64%): $^1$H NMR (CDCl$_3$) δ 4.02 (s, 3H), 7.35 (d, 2H), 7.70 (d, 2H), 8.39 (s, 2H), 8.74 (s, 1H), 8.96 (s, 1H); APCI MS m/z 353 [C$_{16}$H$_{11}$F$_3$N$_2$O$_4$+H]$^+$.

Step D

Methyl 2-(4-Trifluoromethylphenyl)-2H-indazole-6-carboxylate

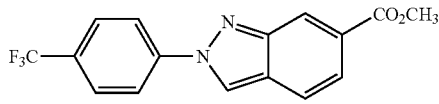

Heat a mixture of methyl 3-nitro-4-[(4-trifluoromethylphenylimino)methyl]benzoate (4.43 g, 12.58 mmol) and sodium azide (0.901 g, 13.86 mmol) in anhydrous DMF (126 mL) at 90° C. under nitrogen for 4 h, cool to room temperature, dilute with water (500 mL) and extract with ethyl acetate (3×250 mL). Wash the combined organic extracts with brine (2× 150 mL), dry over MgSO$_4$ and remove the solvents under reduced pressure. Purify the residue by flash column chromatography on silica gel, eluting with ethyl acetate/hexanes (15:85), to provide methyl 2-(4-trifluoromethylphenyl)-2H-indazole-6-carboxylate as a pale yellow solid (2.75 g, 68%): $^1$H NMR (CDCl$_3$) δ 3.98 (s, 3H), 7.75 (s, 1H), 7.76 (s, 1H), 7.82 (d, 2H), 8.09 (d, 2H), 8.51 (d, 1H), 8.58 (d, 1H); APCI MS m/z 321 [C$_{16}$H$_{11}$F$_3$N$_2$O$_2$+H]$^+$.

Step E

[2-(4-Trifluoromethylphenyl)-2H-indazol-6-yl]methanol

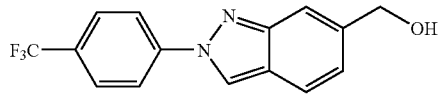

Add a solution of DIBAL-H (1.0 M in hexanes, 21.30 mL, 21.30 mmol) dropwise to a solution of methyl 2-(4-trifluoromethylphenyl)-2H-indazole-6-carboxylate (2.73 g, 7.71 mmol) in anhydrous THF (100 mL) at −78° C. under nitrogen and stir for 4 h. Add a second portion of DIBAL-H (1.0 M in hexanes, 10 mL, 10.0 mmol) and stir for an additional 2 h. Dilute the mixture with saturated aqueous NH$_4$Cl solution (50 mL), warm to room temperature and dilute with ethyl acetate (500 mL). Wash the mixture with 1 N HCl (2×100 mL) and brine (150 mL), dry over MgSO$_4$ and remove the solvents under reduced pressure. Purify the residue by flash column chromatography on silica gel, eluting with ethyl acetate/hexanes (3:7), to provide [2-(4-trifluoromethylphenyl)-2H-indazol-6-yl]methanol as a pale yellow solid (1.82 g, 73%): $^1$H NMR (CDCl$_3$) δ 1.82 (t, 1H), 4.80 (d, 2H), 7.15 (dd, 1H), 7.70 (d, 1H), 7.73 (d, 1H), 7.79 (d, 2H), 8.05 (d, 2H), 8.44 (d, 1H); APCI MS m/z 293 [C$_{15}$H$_{11}$F$_3$N$_2$+H]$^+$.

Step F

Ethyl 2-Methyl-4-[2-(4-trifluoromethylphenyl)-2H-indazol-6-ylmethylsulfanyl]phenoxyacetate

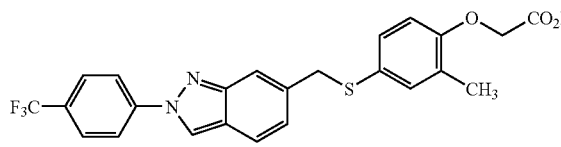

Add tri-n-butylphosphine (0.228 mL, 1.65 mmol) dropwise to a mixture of [2-(4-trifluoromethylphenyl)-2H-indazol-6-yl]methanol (161 mg, 0.551 mmol), ethyl 4-mercapto-2-methylphenoxyacetate (187 mg, 0.826 mmol) and 1,1'-(azodicarbonyl)dipiperidine (ADDP, 278 mg, 1.10 mmol) in anhydrous toluene (10 mL) at 0° C. under argon and stir for 2 h. Warm the mixture to room temperature, stir for 8 h and dilute with methylene chloride (300 mL). Treat the mixture with silica gel (3 g), remove the solvents under reduced pressure and purify the residue by flash column chromatography on silica gel, eluting with ethyl acetate/hexanes (1:9), to provide ethyl 2-methyl-4-[2-(4-trifluoromethylphenyl)-2H-indazol-6-ylmethylsulfanyl]phenoxy acetate as a pale yellow oil (275 mg): APCI MS m/z 501 [C$_{26}$H$_{23}$F$_3$N$_2$O$_3$S+H]$^+$.

Example 19

2-Methyl-4-[2-(4-trifluoromethylphenyl)-2H-indazol-6-ylmethylsulfanyl]phenoxyacetic Acid

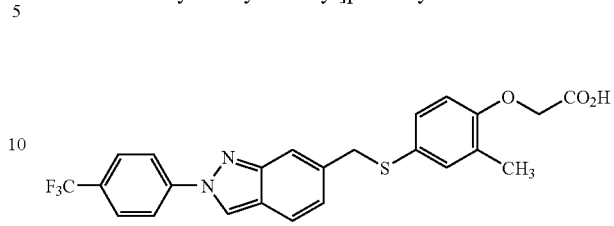

Add a solution of 1 N NaOH (2.75 mL, 2.75 mmol) to a mixture of ethyl 2-methyl-4-[2-(4-trifluoromethylphenyl)-2H-indazol-6-ylmethylsulfanyl]phenoxyacetate (275 mg, 0.549 mmol, crude product) in methanol (6.00 mL) and methylene chloride (5.00 mL) at room temperature under nitrogen and heat the mixture at 40° C. for 2 h. Cool the mixture to 0° C., dilute with 1 N HCl (2.80 mL) and extract with methylene chloride (60 mL). Dry the organic extract over MgSO$_4$, remove the solvent under reduced pressure and purify the residue by flash column chromatography on silica gel, eluting with methanol/methylene chloride (1:9), to provide 2-methyl-4-[2-(4-trifluoromethylphenyl)-2H-indazol-6-ylmethylsulfanyl]phenoxyacetic acid as a white solid (102 g, 39% over two steps): mp 142-144° C.; $^1$H NMR (DMSO-d$_6$) δ 2.10 (s, 3H), 4.18 (s, 2H), 4.29 (s, 2H), 6.66 (d, 1H), 7.05-7.17 (m, 3H), 7.49 (s, 1H), 7.71 (d, 1H), 7.93 (d, 2H), 8.29 (d, 2H), 9.16 (s, 1H); APCI MS m/z 471 [C$_{24}$H$_{19}$F$_3$N$_2$O$_3$S−H]$^−$. HPLC analysis (retention time=42.02 min) showed one peak, with a total purity of 98.7% (area percent).

Prepare examples 20-25 by a similar method used to prepare example 19.

Example 20

3-{2-Methyl-4-[2-(4-trifluoromethylphenyl)-2H-indazol-6-ylmethylsulfanyl]phenyl}propionic Acid

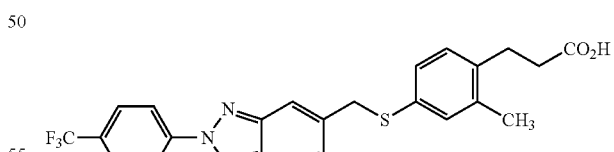

mp 130-132° C.; $^1$H NMR (DMSO-d$_6$) δ 2.22 (s, 3H), 2.44 (t, 2H), 2.74 (t, 2H), 4.30 (s, 2H), 7.07 (d, 1H), 7.08-7.18 (m, 3H), 7.61 (s, 1H), 7.72 (d, 1H), 7.95 (d, 2H), 8.30 (d, 2H), 9.18 (s, 1H), 12.10 (bs, 1H); APCI MS m/z 469 [C$_{25}$H$_{21}$F$_3$N$_2$O$_2$S−H]$^−$. HPLC analysis (retention time=12.39 min) showed one peak, with a total purity of >99% (area percent).

Example 21

2-Ethyl-4-[2-(4-trifluoromethylphenyl)-2H-indazol-6-ylmethylsulfanyl]phenoxyacetic Acid

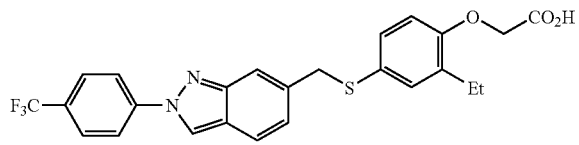

mp 119-121° C.; $^1$H NMR (DMSO-d$_6$) δ 1.05 (t, 3H), 2.53 (q, 2H), 4.21 (s, 2H), 4.65 (s, 2H), 6.77 (d, 1H), 7.05-7.20 (m, 3H), 7.48 (s, 1H), 7.72 (d, 1H), 7.95 (d, 2H), 8.30 (d, 2H), 9.17 (s, 1H), 13.05 (bs, 1H); APCI MS m/z 485 [C$_{25}$H$_{21}$F$_3$N$_2$O$_3$S–H]$^−$. HPLC analysis (retention time=12.58 min) showed one peak, with a total purity of >99% (area percent).

Example 22

3-{2-Ethyl-4-[2-(4-trifluoromethylphenyl)-2H-indazol-6-ylmethoxy]phenyl}propionic Acid

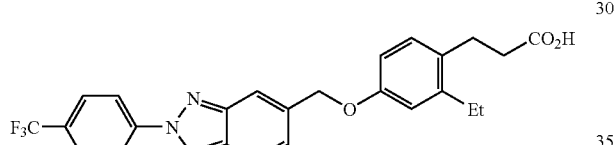

mp 190-192° C.; $^1$H NMR (DMSO-d$_6$) δ 1.16 (t, 3H), 2.44 (t, 2H), 2.58 (q, 2H), 2.77 (t, 2H), 5.17 (s, 2H), 6.81 (dd, 1H), 6.87 (d, 1H), 7.07 (d, 1H), 7.19 (d, 1H), 7.75-7.85 (m, 2H), 7.96 (d, 2H), 8.34 (d, 2H), 9.23 (s, 1H); APCI MS m/z 467 [C$_{26}$H$_{23}$F$_3$N$_2$O$_3$–H]$^−$. HPLC analysis (retention time=12.38 min) showed one peak, with a total purity of >99% (area percent).

Example 23

6-[2-(4-Trifluoromethylphenyl)-2H-indazol-6-ylmethylsulfanyl]benzo[b]thiophen-3ylacetic Acid

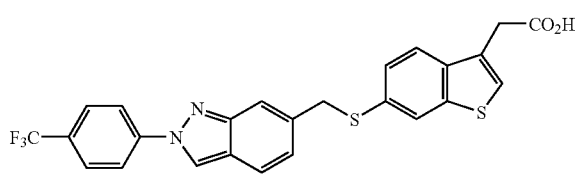

mp 194-196° C.; $^1$H NMR (DMSO-d$_6$) δ 3.80 (s, 2H), 4.42 (s, 2H), 7.18 (d, 1H), 7.42 (dd, 1H), 7.52 (s, 1H), 7.60-7.75 (m, 3H), 7.94 (d, 2H), 8.03 (s, 1H), 8.29 (d, 2H), 9.16 (s, 1H), 12.41 (bs, 1H); APCI MS m/z 497 [C$_{25}$H$_{17}$F$_3$N$_2$O$_2$S$_2$–H]$^−$. HPLC analysis (retention time=12.39 min) showed one peak, with a total purity of >99% (area percent).

Example 24

3-{2-Methyl-4-[2-(4-trifluoromethylphenyl)-2H-indazol-6-ylmethoxy]phenyl}propionic Acid

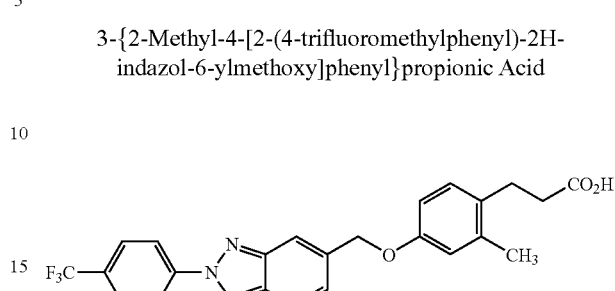

mp 181-183° C.; $^1$H NMR (DMSO-d$_6$) δ 2.24 (s, 3H), 2.44 (t, 2H), 2.74 (t, 2H), 5.17 (s, 2H), 6.81 (dd, 1H), 6.87 (s, 1H), 7.06 (d, 1H), 7.18 (d, 1H), 7.75-7.85 (m, 2H), 7.97 (d, 2H), 8.34 (d, 2H), 9.24 (s, 1H), 12.15 (bs, 1H); APCI MS m/z 453 [C$_{25}$H$_{21}$F$_3$N$_2$O$_3$–H]$^−$. HPLC analysis (retention time=11.92 min) showed one peak, with a total purity of 97.5% (area percent).

Example 25

{6-[2-(4-Trifluoromethylphenyl)-2H-indazol-6-ylmethoxy]benzo[b]thiophen-3-yl}acetic Acid

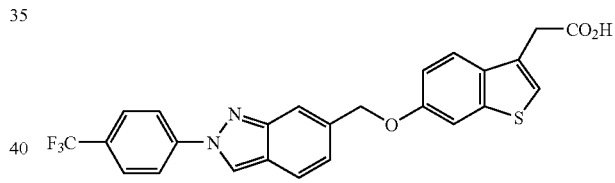

mp 240-242° C.; $^1$H NMR (DMSO-d$_6$) δ 5.28 (s, 2H), 7.09 (dd, 1H), 7.18 (s, 1H), 7.22 (d, 1H), 7.62 (dd, 1H), 7.63 (d, 1H), 7.80 (d, 1H), 7.82 (s, 1H), 7.96 (d, 2H), 8.34 (d, 2H), 9.24 (s, 1H); APCI MS m/z 481 [C$_{25}$H$_{17}$F$_3$N$_2$O$_3$S–H]$^−$. HPLC analysis (retention time=11.90 min) showed one peak, with a total purity of 98.9% (area percent).

Example 26

2-Methyl-4-[2-(4-trifluoromethylphenyl)-2H-indazol-4-ylmethylsulfanyl]phenoxyacetic Acid

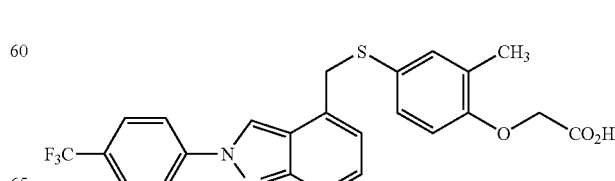

Step A (2-Methyl-6-nitrophenyl)methanol

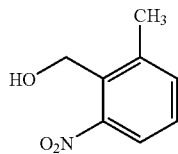

Add pyridine (0.44 mL, 5.5 mmol) to a solution of commercially available 2-nitro-5-methylbenzoic acid (1 g, 5.5 mmol) in methylene chloride (12 mL) at −10° C. under nitrogen, followed by cyanuric fluoride (0.92 mL, 11 mmol) and stir the mixture for 1 h. Dilute the mixture with cold water (80 mL) and extract with methylene chloride (200 mL). Back-extract the aqueous layer with methylene chloride (150 mL), dry the combined organic extracts over $Na_2SO_4$ and remove the solvents under reduced pressure. Dilute the residue with methylene chloride (8 mL) at room temperature under nitrogen and treat the solution with sodium borohydride (0.42 g, 11 mmol). Add methanol (10 mL) dropwise over 10 min and acidify the mixture with 1 N $H_2SO_4$. Remove the solvents under reduced pressure, dilute the residue with water (200 mL) and extract with ethyl acetate (200 mL). Back-extract the aqueous layer with ethyl acetate (250 mL), dry the combined organic extracts over $MgSO_4$ and remove the solvents under reduced pressure to produce (2-methyl-6-nitrophenyl)methanol as a colorless oil (0.67 g, 72%): $^1$H NMR ($CDCl_3$) δ 2.60 (s, 3H), 4.80 (s, 2H), 7.30 (t, 1H), 7.40 (d, 1H), 7.70 (d, 1H).

Step B

2-Methyl-6-nitrobenzaldehyde

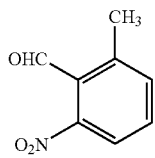

Stir a mixture of chromium(VI) oxide (1.08 g, 10.8 mmol) and 3,5-dimethylpyrazole (1.04 g, 10.8 mmol) in methylene chloride (25 mL) at room temperature under nitrogen for 15 min, and add (2-methyl-6-nitrophenyl)methanol (0.67 g, 4 mmol). Stir the mixture for 30 min and filter through a short plug of silica gel, eluting with ethyl acetate (300 mL). Wash the filtrate with brine (200 mL), dry over $MgSO_4$ and remove the solvents under reduced pressure to produce 2-methyl-6-nitrobenzaldehyde as a dark solid (850 mg, >99%): $^1$H NMR ($CDCl_3$) δ 2.70 (s, 3H), 7.60 (m, 2H), 8.00 (d, 1H), 10.20 (s, 1H).

Step C (2-Methyl-6-nitrobenzylidene)-4-trifluoromethylphenylamine

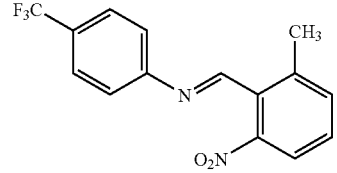

Add 4-(trifluoromethyl)aniline (2.7 g, 21 mmol) to a solution of 2-methyl-6-nitrobenzaldehyde (3.2 g, 19.3 mmol), 5 Å molecular sieves (2 g), $MgSO_4$ (1.5 g) and $Na_2SO_4$ (1.5 g) in HMPA (30 mL) at room temperature under nitrogen and stir the mixture for 130 h. Remove the solids by vacuum filtration, wash the filtrate with water (2× 200 mL), dry over $MgSO_4$ and remove the solvents under reduced pressure to produce (2-methyl-6-nitrobenzylidene)-4-trifluoromethylphenylamine as an off-white solid (5.48 g, 92%): $^1$H NMR ($CDCl_3$) δ 2.60 (s, 3H), 7.30 (d, 2H), 7.50 (t, 1H), 7.60 (d, 1H), 7.70 (d, 2H), 7.90 (d, 1H), 8.80 (s, 1H).

Step D

4-Methyl-2-(4-trifluoromethylphenyl)-2H-indazole

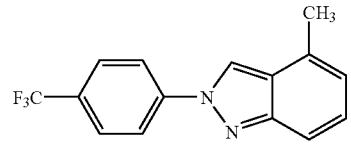

Heat a mixture of (2-methyl-6-nitrobenzylidene)-4-trifluoromethylphenylamine (2.36 g, 7.6 mmol) and sodium azide (600 mg, 9.2 mmol) in HMPA (20 mL) at 150° C. under nitrogen for 2.5 h. Dilute the cooled mixture with water (300 mL) and extract with diethyl ether (4× 250 mL). Dry the combined organic extracts over $MgSO_4$, remove the solvents under reduced pressure and purify the residue by flash column chromatography on silica gel, eluting with hexanes/ethyl acetate (98:2), to afford 4-methyl-2-(4-trifluoromethylphenyl)-2H-indazole as an off-white solid (1.2 g, 57%): $^1$H NMR ($CDCl_3$) δ 2.60 (s, 3H), 6.85 (d, 1H), 7.20 (m, 1H), 7.60 (d, 1H), 7.80 (d, 2H), 8.10 (d, 2H), 8.40 (s, 1H); APCI MS m/z 277 $[C_{15}H_{11}F_3N_2+H]^+$.

Step E

4-Bromomethyl-2-(4-trifluoromethylphenyl)-2H-indazole

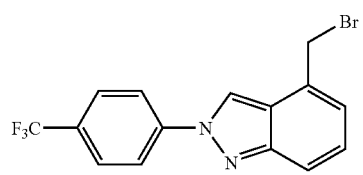

Add N-bromosuccinimide (355 mmol, 2 mmol) to a solution of 4-methyl-2-(4-trifluoromethylphenyl)-2H-indazole (750 mg, 2.7 mmol) in carbon tetrachloride (30 mL) at room temperature under nitrogen, followed by benzoyl peroxide (100 mg, 0.4 mmol). Heat the mixture at reflux for 20 h, add additional N-bromosuccinimide (70 mg, 0.4 mmol) and heat the mixture for an additional 5 h. Dilute the cooled mixture with water (200 mL) and extract with chloroform (2× 100 mL). Dry the combined organic extracts over MgSO$_4$ and remove the solvents under reduced pressure to afford 4-bromomethyl-2-(4-trifluoromethylphenyl)-2H-indazole as an amber oil (900 mg, 93%): $^1$H NMR (CDCl$_3$) δ 4.80 (s, 2H), 7.10 (d, 1H), 7.20 (m, 1H), 7.80 (m, 3H), 8.10 (d, 2H), 8.70 (s, 1H).

Step F

Ethyl 2-Methyl-4-[2-(4-trifluoromethylphenyl)-2H-indazol-4-ylmethylsulfanyl]phenoxyacetate

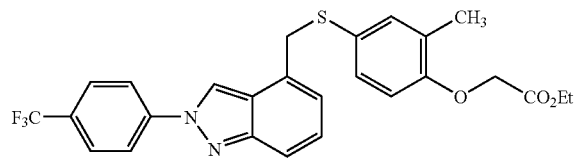

Add potassium carbonate (240 mg, 2.1 mmol) to a solution of 4-bromomethyl-2-(4-trifluoromethylphenyl)-2H-indazole (300 mg, 0.84 mmol) and ethyl 4-mercapto-2-methylphenoxyacetate (190 mg, 0.84 mmol) in acetonitrile (5 mL) at room temperature under nitrogen and stir the mixture for 17 h. Dilute the mixture with water (200 mL) and extract with chloroform (3× 100 mL). Dry the combined organic extracts over MgSO$_4$, remove the solvents under reduced pressure and purify the residue by flash column chromatography on silica gel, eluting with hexanes/ethyl acetate (97:3) to afford ethyl 2-methyl-4-[2-(4-trifluoromethylphenyl)-2H-indazol-4-yl-methylsulfanyl]phenoxyacetate as a white solid (250 mg, 60%): $^1$H NMR (CDCl$_3$) δ 1.30 (t, 3H), 2.20 (s, 3H), 4.20 (m, 4H), 4.60 (s, 2H), 6.60 (d, 1H), 6.80 (d, 1H), 7.10 (d, 1H), 7.20 (m, 2H), 7.60 (d, 1H), 7.70 (d, 2H), 8.10 (d, 2H), 8.30 (s, 1H).

Step G

2-Methyl-4-[2-(4-trifluoromethylphenyl)-2H-indazol-4-ylmethylsulfanyl]phenoxyacetic Acid

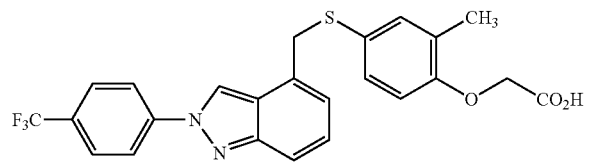

Add a solution of sodium hydroxide (200 mg) in water (1.5 mL) to a solution of ethyl 2-methyl-4-[2-(4-trifluoromethylphenyl)-2H-indazol-4-ylmethylsulfanyl]phenoxy}acetate (230 mg, 0.46 mmol) in diethyl ether (10 mL) and ethanol (12 mL) at room temperature under nitrogen and stir the mixture for 45 min. Dilute the mixture with water (30 mL), remove the solvents under reduced pressure, dilute the residue with water (20 mL) and adjust to pH 1 with 1 N HCl. Collect the solids by vacuum filtration and wash with water (15 mL) to afford {2-methyl-4-[2-(4-trifluoromethylphenyl)-2H-indazol-4-yl-methylsulfanyl]phenoxy}acetic acid as a white solid (200 mg, 92%): mp 105-108° C.; $^1$H NMR (DMSO-d$_6$) δ 2.00 (s, 3H), 4.20 (s, 2H), 4.30 (s, 2H), 6.60 (d, 1H), 6.90 (d, 1H), 7.20 (m, 2H), 7.30 (t, 1H), 7.60 (d, 1H), 8.00 (d, 2H), 8.40 (d, 2H), 9.30 (s, 1H); APCI MS m/z 471 [C$_{24}$H$_{19}$F$_3$N$_2$O$_3$S–H]$^-$. HPLC analysis (retention time=12.1 min) showed one peak, with a total purity of >99% (area percent).

Prepare examples 27-29 by a similar method used to prepare example 26.

Example 27

2-Ethyl-4-[2-(4-trifluoromethylphenyl)-2H-indazol-4-ylmethylsufanyl]phenoxyacetic Acid

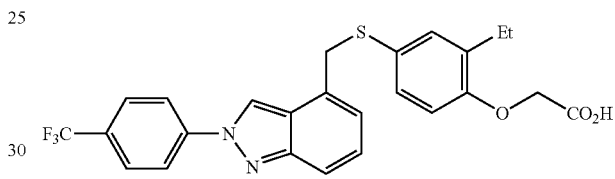

mp 65-70° C.; $^1$H NMR (DMSO-d$_6$) δ 1.00 (t, 3H), 2.50 (q, 2H), 4.40 (s, 2H), 4.50 (s, 2H), 6.70 (d, 1H), 6.90 (d, 1H), 7.10 (s, 1H), 7.20 (m, 2H), 7.60 (d, 1H), 8.00 (d, 2H), 8.30 (d, 2H), 9.20 (1H); APCI MS m/z 487 [C$_{25}$H$_{21}$F$_3$N$_2$O$_3$S+H]$^+$. HPLC analysis (retention time=12.7 min) showed one peak, with a total purity of >99% (area percent).

Example 28

3-{2-Methyl-4-[2-(4-trifluoromethylphenyl)-2H-indazol-4-ylmethylsulfanyl]phenyl}propionic Acid

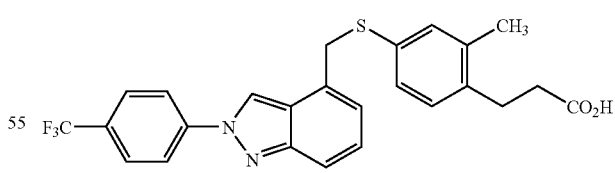

mp 55-59° C.; $^1$H NMR (DMSO-d$_6$) δ 2.20 (s, 3H), 2.50 (t, 2H), 2.80 (t, 2H), 4.50 (s, 2H), 7.00 (m, 5H), 7.50 (d, 1H), 7.90 (d, 2H), 8.40 (d, 2H), 9.30 (s, 1H), 12.00 (br s, 1H); APCI MS m/z 469 [C$_{25}$H$_{21}$F$_3$N$_2$O$_2$S—H]$^-$. HPLC analysis (retention time=12.5 min) showed one peak, with a total purity of 98.0% (area percent).

Example 29

6-[2-(4-Trifluoromethylphenyl)-2H-indazol-4-ylmethylsulfanyl]benzo[b]thiophen-3-ylacetic Acid

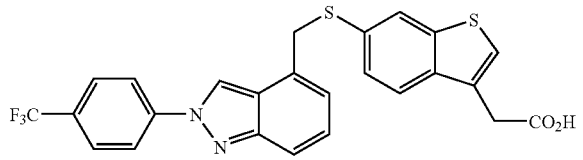

mp 183-185° C.; $^1$H NMR (DMSO-d$_6$) δ 3.80 (s, 2H), 4.60 (s, 2H), 7.10 (d, 1H), 7.30 (t, 1H), 7.40 (d, 1H), 7.50 (s, 1H), 7.60 (d, 1H), 7.70 (d, 1H), 8.00 (d, 2H), 8.10 (s, 1H), 8.30 (d, 2H), 9.40 (s, 1H); APCI MS m/z 497 [C$_{25}$H$_{17}$F$_3$N$_2$O$_2$S$_2$–H]$^-$. HPLC analysis (retention time=12.6 min) showed one peak, with a total purity of 98.5% (area percent).

Example 30

2-Methyl-4-[1-(4-trifluoromethylphenyl)-1H-indazol-4-ylmethylsulfanyl]phenoxyacetic Acid

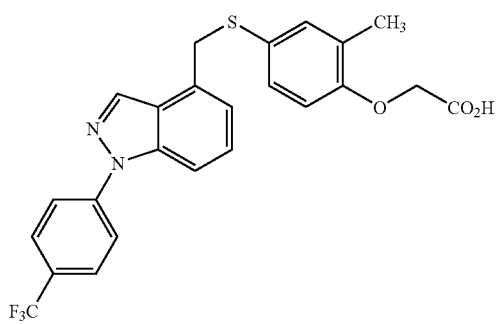

Step A

4-Methyl-1H-indazole

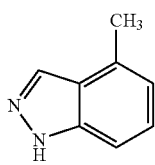

Add tert-butyl nitrite (30 mL, 248 mmol) to a solution of commercially available 2,3-dimethylaniline (20 mL, 165 mmol) in chloroform (600 mL) at room temperature under nitrogen, stir the mixture for 15 min and add 18-crown-6 (4.3 g, 16.5 mmol) and potassium acetate (32 g, 333 mmol). Stir the mixture for 45 min and then heat at reflux for 1 h. Add additional tert-butyl nitrite (10 mL, 82 mmol) and heat the mixture at reflux for an additional 1 h. Remove the solids from the cooled mixture and wash with chloroform (3× 200 mL). Wash the filtrate washed with water (400 mL), dry over MgSO$_4$, remove the solvents under reduced pressure and purify the residue by flash column chromatography on silica gel, eluting with hexanes/ethyl acetate (9:1), to afford 4-methyl-1H-indazole as an off-white solid (5.4 g, 25%): $^1$H NMR (CDCl$_3$) δ 2.70 (s, 3H), 6.90 (d, 1H), 7.50 (m, 2H), 8.10 (s, 1H).

Step B

4-Methyl-1-(4-trifluoromethylphenyl)-1H-indazole

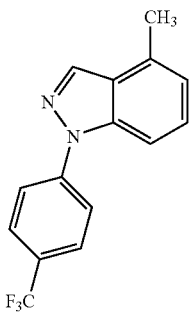

Add triethylamine (10 mL) to a mixture of 4-methyl-1H-indazole (4.9 g, 37 mmol), copper(II) acetate (8.7 g, 48 mmol) and 4-(trifluoromethyl)phenylboronic acid (10 g, 53 mmol) in methylene chloride (200 mL) at room temperature under nitrogen, stir for 19 h and filter the mixture through a short plug of silica gel, eluting with hexanes/ethyl acetate (4:1, 500 mL). Remove approximately two thirds of the solvent volume under reduced pressure, dilute the remaining filtrate with chloroform (400 mL) and wash with water (300 mL). Back-extract the aqueous phase with ethyl acetate (250 mL)dry the combined organic extracts over MgSO$_4$ and remove the solvents under reduced pressure. Purify the residue by flash column chromatography on silica gel, eluting with hexanes/ethyl acetate (99:1), to afford 4-methyl-1-(4-trifluoromethylphenyl)-1H-indazole as an off-white solid (950 mg, 10%): $^1$H NMR (CDCl$_3$) δ 2.70 (s, 3H), 7.00 (d, 1H), 7.40 (t, 1H), 7.60 (d, 1H), 7.80 (d, 2H), 7.90 (d, 2H), 8.20 (s, 1H).

Step C

4-Bromomethyl-1-(4-trifluoromethylphenyl)-1H-indazole

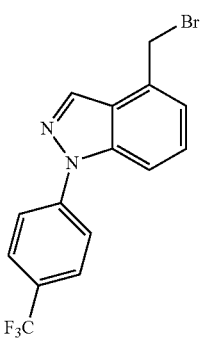

Heat a solution of 4-methyl-1-(4-trifluoromethylphenyl)-1H-indazole (900 mg, 3.2 mmol), N-bromosuccinimide (610 mg, 3.4 mmol) and benzoyl peroxide (40 mg, 0.16 mmol) in carbon tetrachloride (25 mL) under nitrogen at reflux for 16 h. Add additional N-bromosuccinimide (150 mg, 0.8 mmol) and continue to heat the mixture for an additional 5 h at reflux. Dilute the cooled mixture with water (200 mL), extract with methylene chloride (300 mL), dry over MgSO$_4$ and remove the solvents under reduced pressure to afford 4-bromomethyl-1-(4-trifluoromethylphenyl)-1H-indazole as a red solid (1.4 g, >99%): $^1$H NMR (CDCl$_3$) δ 5.00 (s, 2H), 7.20 (d, 1H), 7.40 (t, 1H), 7.70 (d, 1H), 7.80 (d, 2H), 7.90 (d, 2H), 8.5 (s, 1H).

Step D

Ethyl 2-Methyl-4-[1-(4-trifluoromethylphenyl)-1H-indazol-4-ylmethylsulfanyl]phenoxyacetate

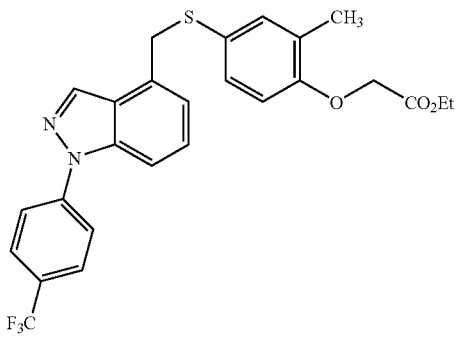

Add potassium carbonate (300 mg, 2.2 mmol) to a solution of 4-bromomethyl-1-(4-trifluoromethylphenyl)-1H-indazole (320 mg, 0.9 mmol) and ethyl 4-mercapto-2-methylphenoxyacetate (230 mg, 1 mmol) in acetonitrile (5 mL) at room temperature under nitrogen and stir the mixture for 16 h. Remove the solids by vacuum filtration, wash the solids with methylene chloride (200 mL) and wash the filtrate with water (200 mL). Back-extract the aqueous phase with methylene chloride (200 mL), dry the combined organic extracts over MgSO$_4$ and remove the solvents were removed under reduced pressure. Purify the residue was purified by flash column chromatography on silica gel, eluting with hexanes/ethyl acetate (96:4), to afford ethyl 2-methyl-4-[1-(4-trifluoromethylphenyl)-1H-indazol-4-ylmethylsulfanyl]phenoxyacetate as a white solid (230 mg, 51%): $^1$H NMR (CDCl$_3$) 1.30 (t, 3H), 2.10 (s, 3H), 4.20 (q, 2H), 4.30 (s, 2H), 4.60 (s, 2H), 6.60 (d, 1H), 7.00 (d, 1H), 7.10 (m, 2H), 7.30 (t, 1H), 7.70 (d, 1H), 7.80 (d, 2H), 7.90 (d, 2H), 8.20 (s, 1H).

Step E

2-Methyl-4-[1-(4-trifluoromethylphenyl)-1H-indazol-4-ylmethylsulfanyl]phenoxyacetic Acid

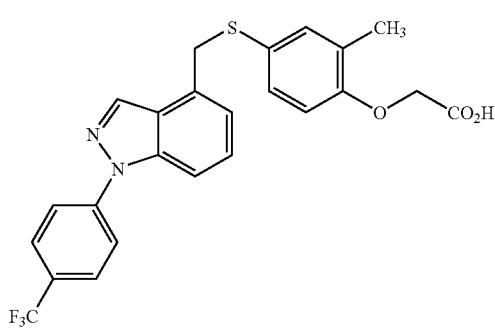

Add a solution of sodium hydroxide (200 mg, 5 mmol) in water (2 mL) to a solution of ethyl 2-methyl-4-[1-(4-trifluoromethylphenyl)-1H-indazol-4-ylmethylsulfanyl]phenoxyacetate (230 mg, 0.46 mmol) in diethyl ether (6 mL) and methanol (10 mL) at room temperature under nitrogen and stir the mixture for 45 min. Dilute the mixture with water (5 mL), remove the solvents under reduced pressure, dilute the residue with water (10 mL) and acidified to pH 1 with 1 N HCl. Collect the solids by vacuum filtration and wash with water (10 mL) to afford 2-ethyl-4-[1-(4-trifluoromethylphenyl)-1H-indazol-4-ylmethylsulfanyl]phenoxyacetic acid as a white solid (180 mg, 82%): mp 132-134° C.; $^1$H NMR (DMSO-d$_6$) δ 2.00 (s, 3H), 4.50 (s, 2H), 4.60 (s, 2H), 6.70 (d, 1H), 7.20 (m, 3H), 7.40 (t, 1H), 7.80 (d, 1H), 7.90 (d, 2H), 8.00 (d, 2H), 8.60 (s, 1H); APCI MS m/z 471 [C$_{24}$H$_{19}$F$_3$N$_2$O$_3$S−H]$^-$. HPLC analysis (retention time=12.6 min) showed one peak, with a total purity of >99% (area percent).

Prepare examples 31-32 by a similar method used to prepare example 30.

Example 31

2-Ethyl-4-[1-(4-trifluoromethylphenyl)-1H-indazol-4-ylmethylsulfanyl]phenoxyacetic Acid

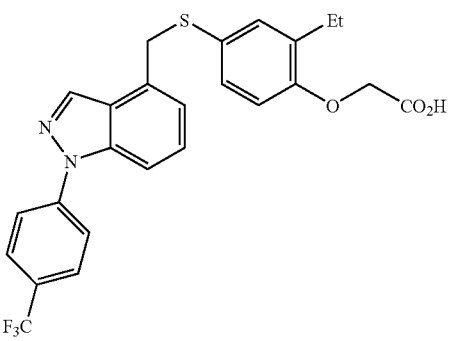

mp 122-124° C.; $^1$H NMR (DMSO-d$_6$) δ 1.00 (t, 3H), 2.50 (q, 2H), 4.50 (s, 2H), 4.70 (s, 2H), 6.70 (d, 1H), 7.10 (m, 3H), 7.40 (t, 1H), 7.80 (d, 1H), 7.90 (d, 2H), 8.10 (d, 2H), 8.50 (s, 1H); APCI MS m/z 487 [C$_{25}$H$_{21}$F$_3$N$_2$O$_3$S+H]$^+$. HPLC analysis (retention time=13.1 min) showed one peak, with a total purity of >99% (area percent).

Example 32

3-{2-Methyl-4-[1-(4-trifluoromethylphenyl)-1H-indazol-4-ylmethylsulfanyl]phenyl}propionic Acid

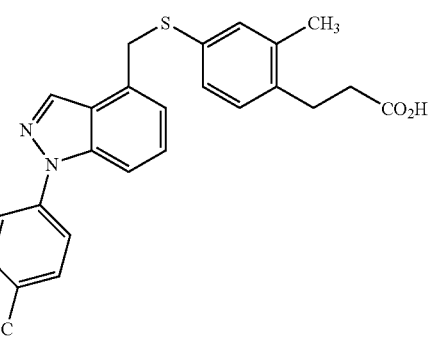

mp 113-115° C.; $^1$H NMR (DMSO-d$_6$) δ 2.20 (s, 3H), 2.40 (t, 2H), 2.70 (t, 2H), 4.60 (s, 2H), 7.10 (d, 1H), 7.20 (m, 3H), 7.40 (t, 1H), 7.80 (d, 1H), 7.90 (d, 2H), 8.10 (d, 2H), 8.60 (s, 1H); APCI MS m/z 469 [C$_{25}$H$_{21}$F$_3$N$_2$O$_2$S−H]$^-$. HPLC analysis (retention time=12.8 min) showed one peak, with a total purity of >99% (area percent).

Example 33

3-{2-Methyl-4-[1-(4-trifluoromethylphenyl)-1H-indazol-7-ylmethylsulfanyl]phenyl}propionic Acid

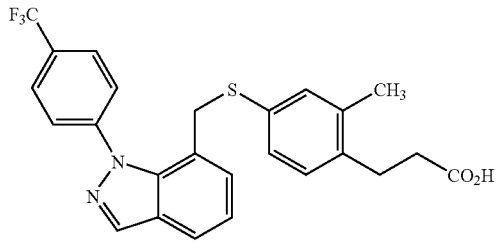

Step A

7-Methyl-1H-indazole

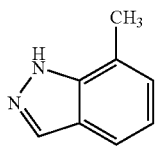

Add tert-butyl nitrite (52 mL) to a solution of commercially available 2,6-dimethylaniline (25 g, 206 mmol) in chloroform (750 mL) at room temperature under nitrogen, stir the mixture for 20 min and add potassium acetate (40 g, 412 mmol) and 18-crown-6 (5.4 g, 20.6 mmol). Heat the mixture at reflux for 3 h, cool to room temperature and stir for an additional 15 h. Remove the solids from the cooled mixture by vacuum filtration and wash with chloroform (400 mL). Wash the filtrate with water (2×250 mL), dry over MgSO$_4$ and remove the solvents were removed under reduced pressure. Purify the residue by flash column chromatography on silica gel, eluting with hexanes/ethyl acetate (9:1), to afford 7-methyl-1H-indazole as an orange solid (23 g, 85%): $^1$H NMR (CDCl$_3$) δ 2.60 (s, 3H), 7.10 (m, 2H), 7.70 (d, 1H), 8.10 (s, 1H).

Step B

7-Methyl-1-(4-trifluoromethylphenyl)-1H-indazole

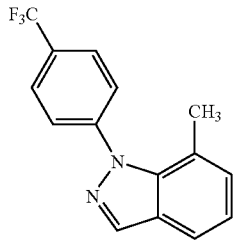

Add triethylamine (15 mL) to a mixture of 7-methyl-1H-indazole (7.6 g, 57 mmol), copper(II) acetate (15.6 g, 87 mmol) and 4-(trifluoromethyl)phenylboronic acid (11 g, 58 mmol) and methylene chloride (220 mL) at room temperature under nitrogen, stir for 18 h and filter the mixture through a short plug of silica gel, eluting with hexanes/ethyl acetate (4:1). Wash the filtrate with water (400 mL), dry over MgSO$_4$, remove the solvents under reduced pressure and purify the residue by flash column chromatography on silica gel, eluting with hexanes/ethyl acetate (97:3), to afford 7-methyl-1-(4-trifluoromethylphenyl)-1H-indazole as a brown solid (500 mg, 4%): $^1$H NMR (CDCl$_3$) δ 2.20 (s, 3H), 7.20 (m, 2H), 7.60 (d, 2H), 7.70 (d, 1H), 7.80 (d, 2H), 8.20 (s, 1H).

Step C

7-Bromomethyl-1-(4-trifluoromethylphenyl)-1H-indazole

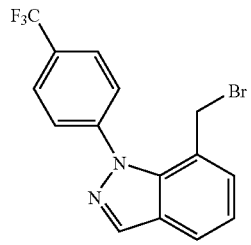

Heat a mixture of 7-methyl-1-(4-trifluoromethylphenyl)-1H-indazole (400 mg, 1.4 mmol), N-bromosuccinimide (267 mg, 1.5 mmol) and benzoyl peroxide (50 mg, 0.14 mmol) in carbon tetrachloride (20 mL) at reflux under nitrogen for 16 h, dilute the cooled mixture with water (200 mL) and extract with chloroform (2× 200 mL). Dry the combined organic extracts over MgSO$_4$ and remove the solvents under reduced pressure to afford 7-bromomethyl-1-(4-trifluoromethylphenyl)-1H-indazole as a brown oil (500 mg, >99%): $^1$H NMR (CDCl$_3$) δ 4.40 (s, 2H), 7.20 (m, 1H), 7.50 (m, 1H), 7.70 (d, 2H), 7.80 (m, 3H), 8.25 (s, 1H).

Step D

Methyl 3-{2-Methyl-4-[1-(4-trifluoromethylphenyl)-1H-indazol-7-ylmethylsulfanyl]phenyl}propionate

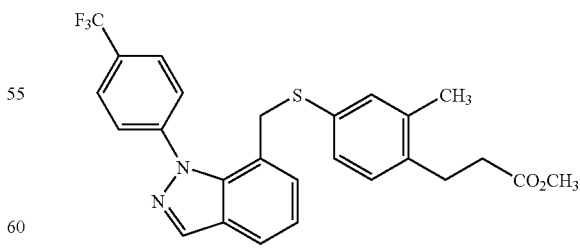

Add potassium carbonate (250 mg, 1.8 mmol) to a solution of 7-bromomethyl-1-(4-trifluoromethylphenyl)-1H-indazole (250 mg, 0.74 mmol) and methyl 3-(4-mercapto-2-methylphenyl)propionate (200 mg, 0.95 mmol) in acetonitrile (5 mL) at room temperature under nitrogen and stir the mixture for 15 h. Remove the solids by vacuum filtration and wash with methylene chloride (200 mL). Wash the filtrate with water (250 mL) and back-extract the aqueous layer with methylene chloride (2× 150 mL). Dry the combined organic extracts over $MgSO_4$, remove the solvents under reduced pressure and purify the residue by flash column chromatography on silica gel, eluting with hexanes/ethyl acetate (9:1), to afford methyl 3-{2-methyl-4-[1-(4-trifluoromethylphenyl)-1H-indazol-7-ylmethylsulfanyl]phenyl}propionate as a white solid (80 mg, 23%): $^1$H NMR ($CDCl_3$) δ 2.20 (s, 3H), 2.50 (t, 2H), 2.90 (t, 2H), 3.70 (s, 3H), 4.00 (s, 2H), 6.70 (m, 2H), 6.90 (d, 1H), 7.20 (d, 1H), 7.30 (m, 2H), 7.70 (m, 4H), 8.20 (s, 1H).

Step E

3-{2-Methyl-4-[1-(4-trifluoromethylphenyl)-1H-indazol-7-ylmethylsulfanyl]phenyl}propionic Acid

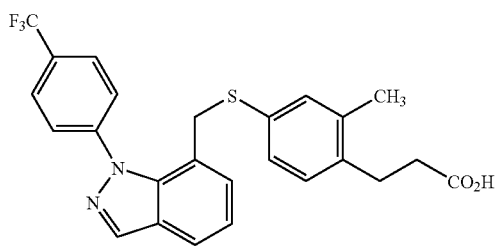

Add a solution of sodium hydroxide (100 mg, 2.5 mmol) in water (1.5 mL) to a solution of methyl 3-{2-methyl-4-[1-(4-trifluoromethylphenyl)-1H-indazol-7-ylmethylsulfanyl]phenyl}propionate (80 mg, 0.16 mmol) in methylene chloride (3 mL) and methanol (3 mL) at room temperature under nitrogen and stir the mixture for 1 h. Add additional sodium hydroxide (100 mg, 2.5 mmol), stir the mixture for an additional 1.5 h, dilute the mixture with water (10 mL) and remove the solvents under reduced pressure. Add water (15 mL), adjust the mixture to pH 1 with 1 N HCl and cool the mixture to 0° C. Collect the solids by vacuum filtration and wash with water (15 mL) and hexanes (20 mL) to afford 3-{2-methyl-4-[1-(4-trifluoromethylphenyl)-1H-indazol-7-ylmethylsulfanyl]phenyl}propionic acid as a white solid (35 mg, 46%): mp 120-123° C.;

$^1$H NMR ($CDCl_3$) δ 2.10 (s, 3H), 2.50 (t, 2H), 2.80 (t, 2H), 3.90 (s, 2H), 6.70 (m, 2H), 6.90 (d, 1H), 7.10 (t, 1H), 7.20 (m, 1H), 7.60 (m, 4H), 7.70 (d, 1H), 8.20 (s, 1H); APCI MS m/z 471 $[C_{25}H_{21}F_3N_2O_2S+H]^+$. HPLC analysis (retention time=11.8 min) showed one peak, with a total purity of 95.9% (area percent).

Prepare example 34 by a similar method used to prepare example 33.

Example 34

2-Methyl-4-[1-(4-trifluoromethylphenyl)-1H-indazol-7-ylmethylsulfanyl]phenoxyacetic Acid

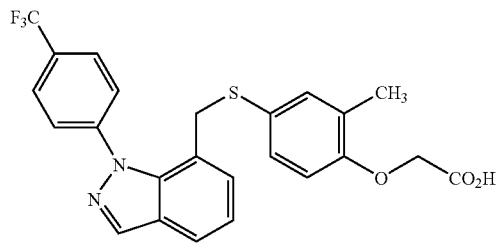

mp 118-121° C.; $^1$H NMR ($CDCl_3$) δ 2.10 (s, 3H), 3.80 (s, 2H), 4.60 (s, 2H), 6.50 (d, 1H), 6.70 (d, 1H), 6.80 (s, 1H), 7.10 (m, 2H), 7.70 (m, 5H), 8.20 (s, 1H); APCI MS m/z 471 $[C_{24}H_{19}F_3N_2O_3S-H]^-$. HPLC analysis (retention time=8.7 min) showed one peak, with a total purity of 96.3% (area percent).

Prepare Examples 35-39 by a similar method used to prepare Example 1.

Example 35

2-Methyl-2-{2-methyl-4-[2-(4-trifluoromethylphenyl)-2H-indazol-7-ylmethylsulfanyl]phenoxy}propionic Acid mp 135-137° C.; $^1$H NMR ($CDCl_3$) δ 1.59 (s, 6H), 2.18 (s, 3H), 4.49 (s, 2H), 6.68 (d, 1H), 6.99 (dd, 1H), 7.06-7.12 (m, 2H), 7.55 (d, 1H), 7.77 (d, 2H), 8.05 (d, 2H), 8.44 (s, 1H); ESI MS m/z 499 $[C_{26}H_{23}F_3N_2O_3S-H]^-$. HPLC analysis (retention time=13.57 min) showed one peak, with a total purity of >99% (area percent).

Example 36

2-Methyl-2-{4-[2-(4-trifluoromethylphenyl)-2H-indazol-7-ylmethylsulfanyl]phenoxy}propionic Acid mp 140-142° C.; $^1$H NMR (CDCl$_3$) δ 1.57 (s, 6H), 4.51 (s, 2H), 6.82 (d, 2H), 6.84-7.08 (m, 2H), 7.31 (d, 2H), 7.58 (d, 1H), 7.78 (d, 2H), 8.06 (d, 2H), 8.46 (s, 1H); ESI MS m/z 485 [C$_{25}$H$_{21}$F$_3$N$_2$O$_3$S–H]$^-$. HPLC analysis (retention time=12.95 min) showed one peak, with a total purity of 98.0% (area percent).

Example 37

2-Methyl-2-{2-methyl-4-[2-(4-trifluoromethylphenyl)-2H-indazol-7-ylmethoxy]phenoxy}propionic Acid

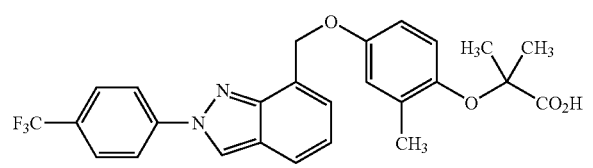

mp 165-167° C.; $^1$H NMR (CDCl$_3$) δ 1.56 (s, 6H), 2.24 (s, 3H), 5.53 (s, 2H), 6.83 (d, 2H), 6.95 (s, 1H), 7.15 (dd, 1H), 7.46 (dd, 1H), 7.67 (d, 1H), 7.79 (d, 2H), 8.08 (d, 2H), 8.49 (s, 1H), 9.70 (bs, 1H); ESI MS m/z 483 [C$_{26}$H$_{23}$F$_3$N$_2$O$_4$–H]$^-$. HPLC analysis (retention time=13.11 min) showed one peak, with a total purity of 98.7% (area percent).

Example 38

2-Methyl-2-{4-[2-(4-trifluoromethylphenyl)-2H-indazol-7-ylmethoxy]phenylsulfanyl}propionic Acid

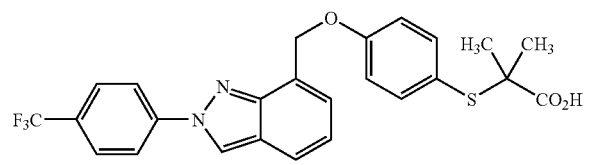

mp 175-177° C.; $^1$H NMR (CDCl$_3$) δ 1.48 (s, 6H), 5.56 (s, 2H), 7.01-7.06 (m, 2H), 7.12 (d, 1H), 7.41-7.46 (m, 3H), 7.65 (d, 1H), 7.77 (d, 2H), 8.05 (d, 2H), 8.47 (s, 1H); APCI MS m/z 485 [C$_{25}$H$_{21}$F$_3$N$_2$O$_3$S–H]$^-$. HPLC analysis (retention time=13.07 min) showed one peak, with a total purity of 98.3% (area percent).

Example 39

2-Methyl-2-{4-[2-(4-trifluoromethylphenyl)-2H-indazol-7-ylmethoxy]phenoxy}propionic Acid

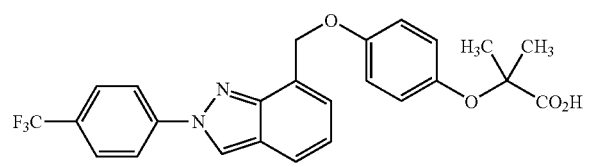

mp 178-180° C.; $^1$H NMR (DMSO-d$_6$) δ 1.45 (s, 6H), 5.44 (s, 2H), 6.85 (d, 2H), 7.00 (d, 2H), 7.16 (dd, 1H), 7.42 (d, 1H), 7.77 (d, 1H), 7.98 (d, 2H), 8.35 (d, 2H), 9.30 (s, 1H); APCI MS m/z 469 [C$_{25}$H$_{21}$F$_3$N$_2$O$_4$–H]$^-$. HPLC analysis (retention time=11.68 min) showed one peak, with a total purity of 95.1% (area percent).

Prepare Examples 40-44 by a similar method used to prepare Example 8.

Example 40

(+/−)-2-Methyl-2-(2-methyl-4-{1-[2-(4-trifluoromethylphenyl)-2H-indazol-7-yl]ethoxy}phenoxy)propionic Acid

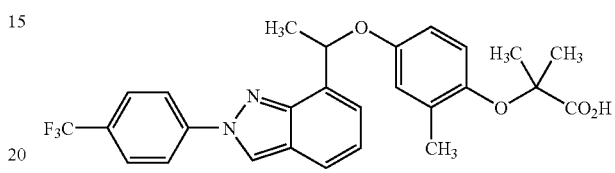

mp 139-141° C.; $^1$H NMR (CDCl$_3$) δ 1.49 (s, 6H), 1.81 (d, 3H), 2.14 (s, 3H), 6.03 (q, 1H), 6.61-6.70 (m, 2H), 6.82 (d, 1H), 7.08 (dd, 1H), 7.36 (d, 1H), 7.60 (dd, 1H), 7.81 (d, 2H), 8.10 (d, 2H), 8.50 (s, 1H), 9.80 (bs, 1H); ESI MS m/z 497 [C$_{27}$H$_{25}$F$_3$N$_2$O$_4$–H]$^-$.

HPLC analysis (retention time=13.91 min) showed one peak, with a total purity of 95.5% (area percent).

Example 41

(+/−)-2-Methyl-2-(2-methyl-4-{1-[2-(4-trifluoromethylphenyl)-2H-indazol-7-yl]ethylsulfanyl}phenoxy)propionic Acid

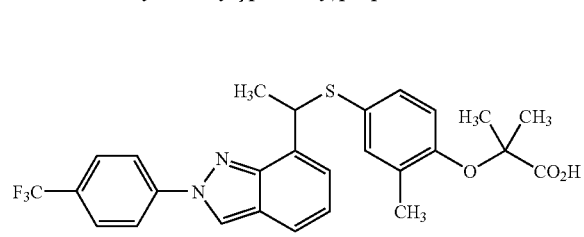

mp 140-142° C.; $^1$H NMR (CDCl$_3$) δ 1.56 (s, 6H), 1.79 (d, 3H), 2.15 (s, 3H), 5.09 (q, 1H), 6.64 (d, 1H), 7.01-7.10 (m, 2H), 7.17 (d, 1H), 7.24 (d, 1H), 7.56 (dd, 1H), 7.78 (d, 2H), 8.07 (d, 2H), 8.45 (s, 1H); ESI MS m/z 513 [C$_{27}$H$_{25}$F$_3$N$_2$O$_3$S–H]$^-$. HPLC analysis (retention time=14.49 min) showed one peak, with a total purity of 98.0% (area percent).

Example 42

(+/−)-2-Methyl-2-(4-{1-[2-(4-trifluoromethylphenyl)-2H-indazol-7-yl]ethylsulfanyl}phenoxy)propionic Acid

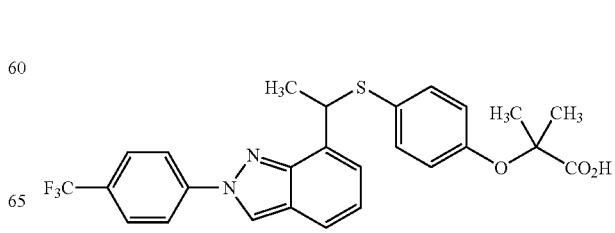

mp 150-152° C.; $^1$H NMR (CDCl$_3$) δ 1.55 (s, 6H), 1.79 (d, 3H), 5.09 (q, 1H), 6.77 (d, 2H), 7.03 (dd, 1H), 7.16 (d, 1H), 7.26-7.30 (m, 2H), 7.56 (d, 1H), 7.78 (d, 2H), 8.06 (d, 2H), 8.45 (s, 1H); ESI MS m/z 499 [C$_{26}$H$_{23}$F$_3$N$_2$O$_3$S−H]$^−$. HPLC analysis (retention time=13.51 min) showed one peak, with a total purity of 97.2% (area percent).

Example 43

(+/−)-2-Methyl-2-(4-{1-[2-(4-trifluoromethylphenyl)-2H-indazol-7-yl]ethoxy}phenylsulfanyl)propionic Acid

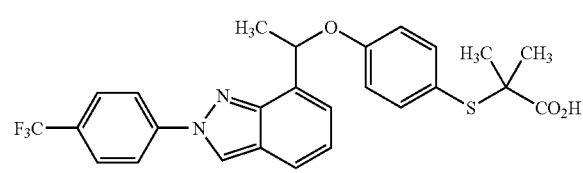

mp 158-160° C.; $^1$H NMR (CDCl$_3$) δ 1.41 (s, 6H), 1.82 (d, 3H), 6.08 (q, 1H), 6.85 (d, 1H), 7.06 (dd, 1H), 7.25-7.33 (m, 3H), 7.59 (d, 1H), 7.79 (d, 2H), 8.07 (d, 2H), 8.47 (s, 1H); APCI MS m/z 499 [C$_{26}$H$_{23}$F$_3$N$_2$O$_3$S−H]$^−$. HPLC analysis (retention time=14.27 min) showed one peak, with a total purity of 96.0% (area percent).

Example 44

(+/−)-2-Methyl-2-(4-{1-[2-(4-trifluoromethylphenyl)-2H-indazol-7-yl]ethoxy}phenoxy)propionic Acid

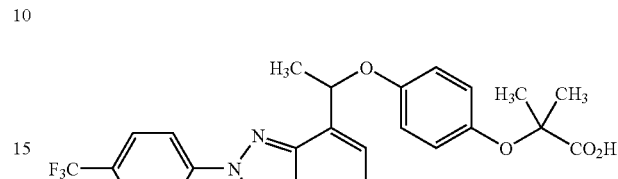

mp 130-132° C.; $^1$H NMR (DMSO-d$_6$) δ 1.39 (s, 6H), 1.74 (d, 3H), 5.95 (q, 1H), 6.73 (d, 2H), 6.83 (d, 2H), 7.10 (dd, 1H), 7.30 (d, 1H), 7.70 (s, 1H), 8.00 (d, 2H), 8.38 (d, 2H), 9.29 (s, 1H); APCI MS m/z 483 [C$_{26}$H$_{23}$F$_3$N$_2$O$_4$−H]$^−$. HPLC analysis (retention time=12.23 min) showed one peak, with a total purity of 96.4% (area percent).

Preparation of examples 45-50.

Scheme IX

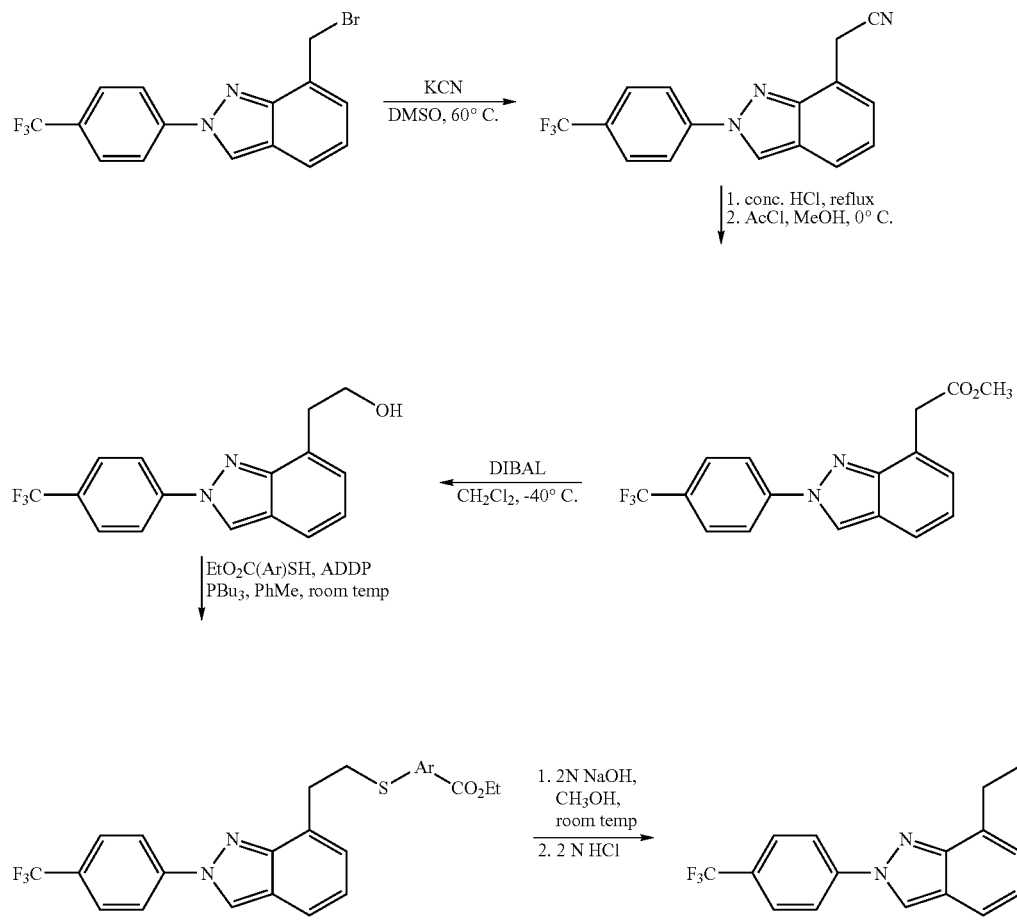

Preparation 40

[2-(4-Trifluoromethylphenyl)-2H-indazol-7-yl]acetonitrile

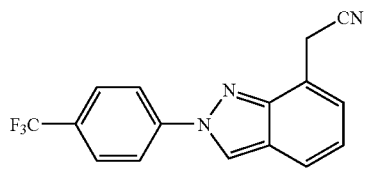

Add potassium cyanide (2.01 g, 31 mmol) to a solution of 7-bromomethyl-2-(4-trifluoromethylphenyl)-2H-indazole (1.31 g, 10.2 mmol) in DMSO (40 mL) at room temperature under nitrogen, heat the mixture to 60° C. and stir the mixture for 3.5 h. Cool the mixture, dilute with water and extract with diethyl ether (3× 100 mL). Wash the combined organic extracts with brine (2× 60 mL), dry over magnesium sulfate and remove the solvents under reduced pressure. Purify the residue by flash column chromatography on silica gel, eluting with hexanes/ethyl acetate (9:1), to afford [2-(4-trifluoromethylphenyl)-2H-indazol-7-yl]acetonitrile as a yellow solid (1.51 g, 50%): $^1$H NMR (CDCl$_3$) δ 4.17 (s, 2H), 7.17 (t, 1H), 7.40 (d, 1H), 7.68 (d, 1H), 7.80 (d, 2H), 8.07 (d, 2H), 8.47 (s, 1H).

Preparation 41

Methyl [2-(4-Trifluoromethylphenyl)-2H-indazol-7-yl]acetate

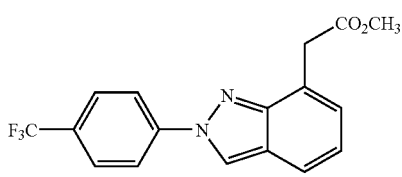

Heat a suspension of preparation 40, [2-(4-trifluoromethylphenyl)-2H-indazol-7-yl]acetonitrile (1.23 g, 4.08 mmol), in concentrated hydrochloric acid (100 mL) at reflux for 8 h and extract the cooled mixture with ethyl acetate (300 mL). Wash the organic extract with water (100 mL) and brine (100 mL), dry over sodium sulfate and remove the solvent under reduced pressure to afford the crude carboxylic acid as a yellow solid (1.27 g). Dissolve the acid in methanol (50 mL) and cool the mixture to 0° C. under nitrogen. Add acetyl chloride (5 mL), warm the mixture to room temperature and stir for 12 h. Remove the solvent under reduced pressure, and dilute the residue with ethyl acetate (250 mL). Wash the mixture with water (100 mL), brine (50 mL), saturated aqueous sodium bicarbonate solution (50 mL) and brine (50 mL), dry over sodium sulfate and remove the solvents under reduced pressure to afford methyl [2-(4-trifluoromethylphenyl)-2H-indazol-7-yl]acetate as a yellow solid (1.29 g, 97% over two steps), which was used in the next step without further purification.

Preparation 42

2-[2-(4-Trifluoromethylphenyl)-2H-indazol-7-yl]ethanol

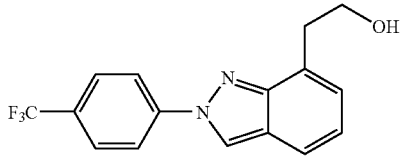

Add a solution of diisobutylaluminum hydride (15.0 ML, 15.0 mmol, 1 M solution in hexanes) to a solution of preparation 41, methyl [2-(4-trifluoromethylphenyl)-2H-indazol-7-yl]acetate, (1.28 g, 3.83 mmol) in methylene chloride (40 mL) at −40° C. under nitrogen and stir the mixture for 5 h. Dilute the mixture with saturated aqueous ammonium chloride solution (20 mL), warm the mixture to room temperature and dilute with ethyl acetate (200 mL). Wash the organic extract with 1 N HCl (2× 50 mL) and brine (100 mL), dry over sodium sulfate and remove the solvents under reduced pressure. Purify the residue by flash column chromatography on silica gel, eluting with hexanes/ethyl acetate (7:3), to afford 2-[2-(4-trifluoromethylphenyl)-2H-indazol-7-yl]ethanol as a yellow solid (1.06 g, 91%): $^1$H NMR (CDCl$_3$) δ 3.33 (t, 2H), 4.07 (t, 2H), 7.07 (s, 2H), 7.63 (d, 1H), 7.80 (d, 2H), 8.05 (d, 2H), 8.47 (s, 1H).

Preparation 43

Ethyl (2-Ethyl-4-{2-[2-(4-trifluoromethylphenyl)-2H-indazol-7-yl]ethylsulfanyl}phenoxy)acetate

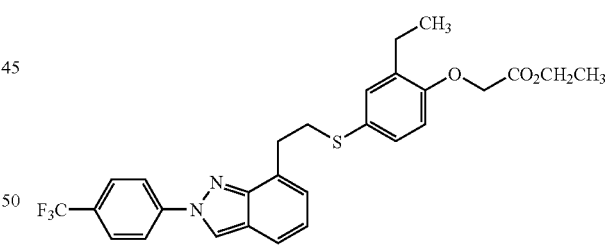

Add-tri-n-butylphosphine (0.25 mL, 1.8 mmol) and 1,1'-(azodicarbonyl)dipiperidine (ADDP, 202 mg, 0.80 mmol) to a solution of preparation 42, 2-[2-(4-trifluoromethylphenyl)-2H-indazol-7-yl]ethanol, (122 mg, 0.40 mmol) and ethyl 4-mercapto-2-ethylphenoxyacetate (125 mg, 0.52 mmol) in toluene (7 mL) at room temperature under nitrogen at 0° C., warm the mixture to room temperature and stir for 16 h. Dilute the mixture with ethyl acetate (60 mL), treat with silica gel (2 g) and remove the solvents were removed under reduced pressure. Purify the residue by flash column chromatography on silica gel, eluting with hexanes/ethyl acetate (9:1), to afford ethyl (2-ethyl-4-{2-[2-(4-trifluoromethylphenyl)-2H-indazol-7-yl]ethylsulfanyl}phenoxy)acetate as a viscous yellow oil (129 mg, 61%): $^1$H NMR (CDCl$_3$) δ 1.15

(t, 3H), 1.25 (t, 3H), 2.18 (q, 2H), 3.40 (q, 2H), 3.45 (q, 2H), 4.25 (q, 2H), 6.65 (d, 1H), 7.00-7.10 (m, 2H), 7.20-7.25 (m, 2H), 7.55 (d, 1H), 7.85 (d, 2H), 8.10 (d, 2H), 8.50 (s, 1H).

Example 45

(2-Ethyl-4-{2-[2-(4-trifluoromethylphenyl)-2H-indazol-7-yl]ethylsulfanyl}phenoxy)acetic Acid

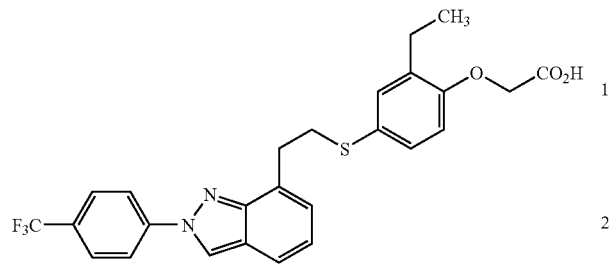

Add a solution of sodium hydroxide (100 mg) in water (1.5 mL) to a solution of ethyl (2-ethyl-4-{2-[2-(4-trifluoromethylphenyl)-2H-indazol-7-yl]ethylsulfanyl}phenoxy)acetate (129 mg, 0.18 mmol) in methanol (4 mL) and diethyl ether (5 mL) at room temperature under nitrogen and stir the mixture for 2 h. Dilute the mixture with water (30 mL) and remove the solvents under reduced pressure. Dilute the residue with water (30 mL), acidify to pH 1 with 1 N HCl and cool to 0° C. Collect the solids by vacuum filtration and wash with water (15 mL) and hexanes (15 mL) to afford (2-ethyl-4-{2-[2-(4-trifluoromethylphenyl)-2H-indazol-7-yl] ethylsulfanyl}phenoxy)acetic acid as a white solid (80 mg, 84%): mp 115-117° C.; $^1$H NMR (CDCl$_3$) δ 1.12 (t, 3H), 2.50-2.61 (m, 2H), 3.29-3.39 (m, 4H), 4.51 (s, 2H), 6.61 (d, 1H), 6.97-7.03 (m, 2H), 7.21-7.26 (m, 2H), 7.52 (d, 1H), 7.74 (d, 2H), 8.00 (d, 2H), 8.38 (s, 1H); APCI MS m/z 499 [$C_{26}H_{23}F_3N_2O_3S$—H]$^-$. HPLC analysis (retention time=13.74 min) showed one peak, with a total purity of 99.0% (area percent).

Prepare Examples 46-50 by a similar method used to prepare Example 45.

Example 46

(2-Methyl-4-{2-[2-(4-trifluoromethylphenyl)-2H-indazol-7-yl]ethylsulfanyl}phenoxy)acetic Acid

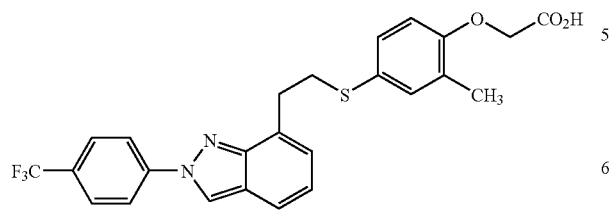

mp 137-139° C.; $^1$H NMR (CDCl$_3$) δ 2.25 (s, 3H), 3.30-3.36 (m, 2H), 3.39-3.45 (m, 2H), 4.67 (s, 2H), 6.67 (d, 1H), 7.01-7.10 (m, 2H), 7.25-7.28 (m, 2H), 7.56 (d, 1H), 7.79 (d, 2H), 8.05 (d, 2H), 8.44 (s, 1H); APCI MS m/z 485 [$C_{25}H_{21}F_3N_2O_3S$–H]$^-$. HPLC analysis (retention time=13.12 min) showed one peak, with a total purity of 98.6% (area percent).

Example 47

2-Methyl-2-(4-{2-[2-(4-trifluoromethylphenyl)-2H-indazol-7-yl]ethoxy}phenoxy)propionic Acid

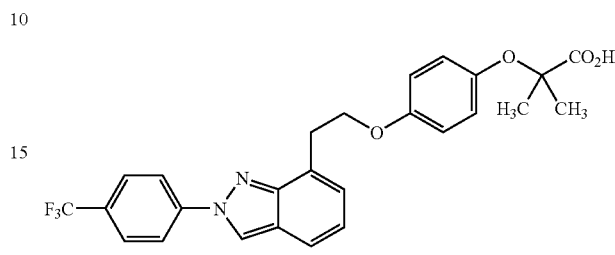

mp 122-124° C.; $^1$H NMR (CDCl$_3$) δ 1.52 (s, 6H), 3.53 (t, 2H), 4.44 (t, 2H), 6.90 (s, 4H), 7.07 (dd, 1H), 7.21 (dd, 1H), 7.59 (d, 1H), 7.79 (d, 2H), 8.08 (d, 2H), 8.46 (s, 1H); APCI MS m/z 483 [$C_{26}H_{23}F_3N_2O_4$–H]$^-$. HPLC analysis (retention time=13.05 min) showed one peak, with a total purity of 98.4% (area percent).

Example 48

2-Methyl-2-(2-methyl-4-{2-[2-(4-trifluoromethylphenyl)-2H-indazol-7-yl]ethoxy}phenoxy)propionic Acid

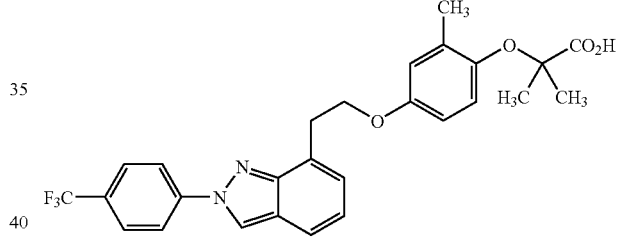

mp 133-135° C.; $^1$H NMR (CDCl$_3$) δ 1.54 (s, 6H), 2.21 (s, 3H), 3.52 (t, 2H), 4.42 (t, 2H), 6.70-6.83 (m, 3H), 7.07 (dd, 1H), 7.21 (d, 1H), 7.59 (d, 1H), 7.79 (d, 2H), 8.08 (d, 2H), 8.46 (s, 1H); APCI MS m/z 497 [$C_{27}H_{25}F_3N_2O_4$–H]$^-$. HPLC analysis (retention time=13.68 min) showed one peak, with a total purity of 98.3% (area percent).

Example 49

2-Methyl-2-(2-methyl-4-{2-[2-(4-trifluoromethylphenyl)-2H-indazol-7-yl]ethylsulfanyl}phenoxy)propionic Acid

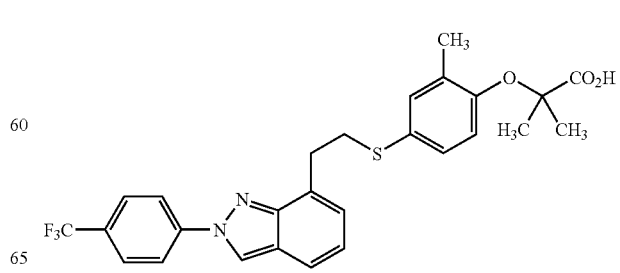

mp 141-143° C.; ¹H NMR (CDCl₃) δ 1.60 (s, 6H), 2.19 (s, 3H), 3.31-3.39 (m, 2H), 3.41-3.45 (m, 2H), 6.75 (d, 1H), 7.01-7.10 (m, 2H), 7.19-7.26 (m, 2H), 7.56 (dd, 1H), 7.79 (d, 2H), 8.04 (d, 2H) 8.43 (s, 1H); APCI-MS m/z 513 [$C_{27}H_{25}F_3N_2O_3S$–H]⁻. HPLC analysis (retention time=14.98 min) showed one peak, with a total purity of >99% (area percent).

Example 50

2-Methyl-2-(4-{2-[2-(4-trifluoromethylphenyl)-2H-indazol-7-yl]ethylsulfanyl}phenoxy)propionic Acid

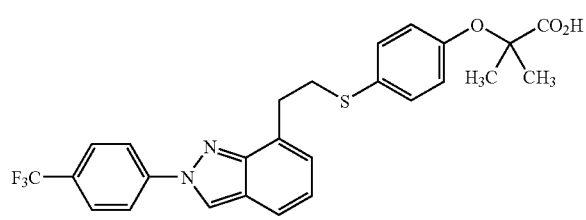

mp 112-114° C.; ¹H NMR (CDCl₃) δ 1.59 (s, 6H), 3.31-3.37 (m, 2H), 3.41-3.47 (m, 2H), 6.88 (d, 2H), 7.02-7.10 (m, 2H), 7.39 (d, 2H), 7.57 (d, 1H), 7.80 (d, 2H), 8.05 (d, 2H), 8.44 (s, 1H); APCI MS m/z 499 [$C_{26}H_{23}F_3N_2O_3S$–H]⁻. HPLC analysis (retention time=14.00 min) showed one peak, with a total purity of 96.3% (area percent).

Prepare Examples 51-56 by a similar method used to prepare Example 18.

Example 51

2-Methyl-2-{2-methyl-4-[2-(4-trifluoromethylphenyl)-2H-indazol-6-ylmethoxy]phenoxy}propionic Acid

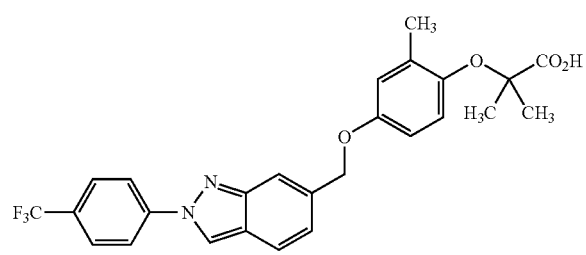

mp 119-121° C.; ¹H NMR (DMSO-d₆) δ 1.44 (s, 6H), 2.15 (s, 3H), 5.13 (s, 2H), 6.72 (d, 1H), 6.79 (dd, 1H), 6.90 (d, 1H), 7.18 (d, 1H), 7.76-7.81 (m, 2H), 7.97 (d, 2H), 8.34 (d, 2H), 9.24 (s, 1H); APCI MS m/z 483 [$C_{26}H_{23}F_3N_2O_4$—H]⁻. HPLC analysis (retention time=12.38 min) showed one peak, with a total purity of 98.0% (area percent).

Example 52

2-Methyl-2-{4-[2-(4-trifluoromethylphenyl)-2H-indazol-6-ylmethoxy]phenoxy}propionic Acid

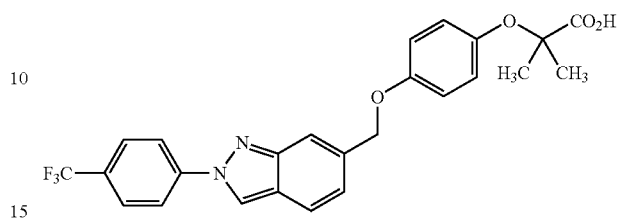

mp 199-201° C.; ¹H NMR (DMSO-d₆) δ 1.44 (s, 6H), 5.15 (s, 2H), 6.82-6.86 9 m, 2H), 6.95-6.99 (m, 2H), 7.18 (dd, 1H), 7.77-7.82 (m, 2H), 7.97 (d, 2H), 8.34 (d, 2H), 9.24 (s, 1H), 12.89 (bs, 1H); APCI MS m/z 469 [$C_{25}H_{21}F_3N_2O_4$—H]⁻. HPLC analysis (retention time=12.01 min) showed one peak, with a total purity of 97.5% (area percent).

Example 53

2-Methyl-2-{2-methyl-4-[2-(4-trifluoromethylphenyl)-2H-indazol-6-ylmethylsulfanyl]phenoxy}propionic Acid

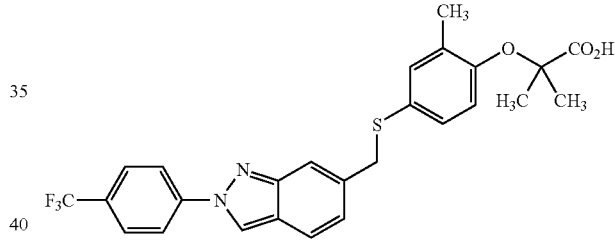

mp 116-118° C.; ¹H NMR (DMSO-d₆) δ 1.48 (s, 6H), 2.10 (s, 3H), 4.23 (s, 2H), 6.62 (d, 1H), 7.12 (d, 2H), 7.21 (d, 1H), 7.52 (d, 1H), 7.72 (d, 1H), 7.95 (d, 2H), 8.31 (d, 2H), 9.19 (s, 1H), 13.05 (s, 1H); APCI MS m/z 499 [$C_{26}H_{23}F_3N_2O_3S$–H]⁻. HPLC analysis (retention time=13.18 min) showed one peak, with a total purity of >99% (area percent).

Example 54

2-Methyl-2-{4-[2-(4-trifluoromethylphenyl)-2H-indazol-6-ylmethylsulfanyl]phenoxy}propionic Acid

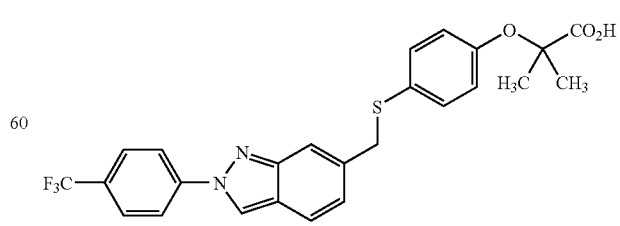

mp 176-178° C.; ¹H NMR (CDCl₃) δ 1.62 (s, 6H), 3.91 (s, 2H), 6.48 (s, 1H), 6.77 (d, 2H), 7.07-7.14 (m, 3H), 7.66 (dd,

1H), 7.79 (d, 2H), 8.00 (d, 2H), 8.38 (s, 1H); APCI MS m/z 485 $[C_{25}H_{21}F_3N_2O_3S-H]^-$. HPLC analysis (retention time=12.40 min) showed one peak, with a total purity of 98.9% (area percent).

Example 55

2-Methyl-2-{4-[2-(4-trifluoromethylphenyl)-2H-indazol-6-ylmethoxy]phenylsulfanyl}propionic Acid

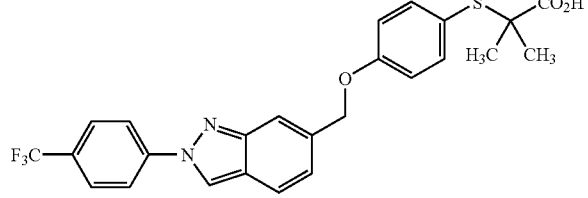

mp 133-135° C.; $^1$H NMR (CDCl$_3$) δ 1.49 (s, 6H), 5.14 (s, 2H), 6.97 (d, 2H), 7.16 (dd, 1H), 7.45 (d, 2H), 7.70 (d, 1H), 7.71-7.79 (m, 3H), 8.03 (d, 2H), 8.43 (s, 1H); APCI MS m/z 485 $[C_{25}H_{21}F_3N_2O_3S-H]^-$. HPLC analysis (retention time=12.63 min) showed one peak, with a total purity of 98.9% (area percent).

Example 56

2-Methyl-2-{4-[2-(4-trifluoromethylphenyl)-2H-indazol-6-ylmethoxymethyl]phenoxy}propionic Acid

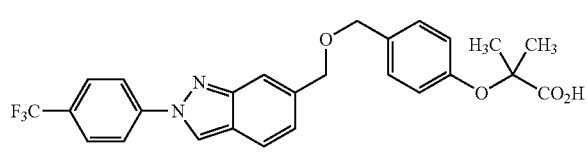

mp 129-131° C.; $^1$H NMR (CDCl$_3$) δ 161 (s, 6H), 4.54 (s, 2H), 4.65 (s, 2H), 6.93 (d, 2H), 7.15 (dd, 1H), 7.25-7.31 (m, 2H), 7.68 (d, 2H), 7.78 (d, 2H), 8.03 (d, 2H), 8.42 (s, 1H); APCI MS m/z 483 $[C_{26}H_{23}F_3N_2O_4-H]^-$. HPLC analysis (retention time=11.95 min) showed one peak, with a total purity of 96.2% (area percent).

Prepare Examples 57-60 by a similar method used to prepare Example 8 except starting from 2-(4-(trifluoromethylphenyl)-2H-indazole-6-carbaldehyde in step B as shown below:

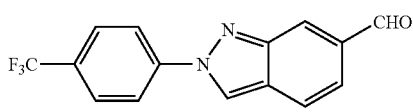

Example 57

(+/−)-2-Methyl-2-(2-methyl-4-{1-[2-(4-trifluoromethylphenyl)-2H-indazol-6-yl]ethoxy}phenoxy)propionic Acid

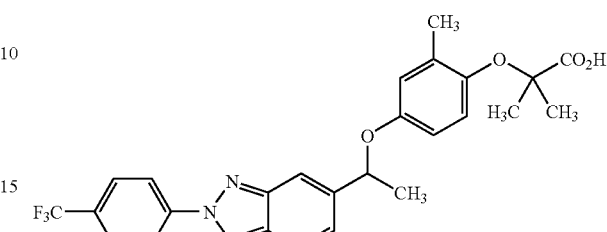

mp 156-158° C.; $^1$H NMR (DMSO-d$_6$) δ 1.40 (s, 6H), 1.58 (d, 3H), 2.08 (s, 3H), 5.48 (q, 1H), 6.59-6.70 (m, 2H), 6.80 (d, 1H), 7.18 (d, 1H), 7.70 (s, 1H), 7.76 (d, 1H), 7.95 (d, 2H), 8.31 (d, 2H), 9.19 (s, 1H), 12.83 (bs, 1H); APCI MS m/z 497 $[C_{27}H_{25}F_3N_2O_4-H]^-$. HPLC analysis (retention time=12.90 min) showed one peak, with a total purity of 98.2% (area percent).

Example 58

(+/−)-2-Methyl-2-(4-{1-[2-(4-trifluoromethylphenyl)-2H-indazol-6-yl]ethoxy}phenoxy)propionic Acid

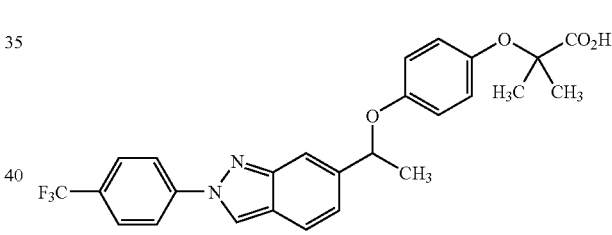

mp 144-146° C.; $^1$H NMR (DMSO-d$_6$) δ 1.39 (s, 6H), 1.59 (d, 3H), 5.49 (q, 1H), 6.73 (d, 2H), 6.86 (d, 2H), 7.18 (d, 1H), 7.70 (s, 1H), 7.77 (d, 1H), 7.95 (d, 2H), 8.31 (d, 2H), 9.20 (s, 1H), 12.90 (bs, 1H); APCI MS m/z 483 $[C_{26}H_{23}F_3N_2O_4—H]^-$. HPLC analysis (retention time=12.26 min) showed one peak, with a total purity of 95.9% (area percent).

Example 59

(+/−)-2-Methyl-2-(4-{1-[2-(4-trifluoromethylphenyl)-2H-indazol-6-yl]ethylsulfanyl}phenoxy)propionic Acid

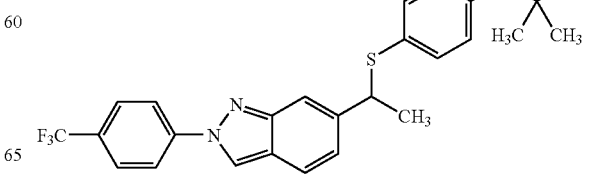

mp 130-132° C.; ¹H NMR (DMSO-d₆) δ 1.44 (s, 6H), 1.58 (d, 3H), 4.52 (q, 1H), 6.71 (d, 2H), 7.18-7.25 (m, 3H), 7.46 (s, 1H), 7.73 (d, 1H), 7.95 (d, 2H), 8.30 (d, 2H), 9.17 (s, 1H), 13.05 (bs, 1H); APCI MS m/z 499 [C$_{26}$H$_{23}$F$_3$N$_2$O$_3$S-H]⁻. HPLC analysis (retention time=13.19 min) showed one peak, with a total purity of 97.8% (area percent).

Example 60

(+/−)-2-Methyl-2-(2-methyl-4-{1-[2-(4-trifluoromethylphenyl)-2H-indazol-6-yl]ethylsulfanyl}phenoxy)propionic Acid

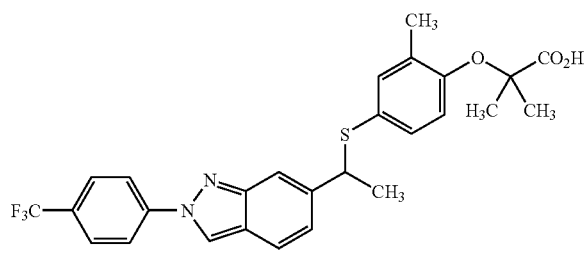

mp 114-116° C.; ¹H NMR (CDCl₃) δ 1.60 (s, 6H), 1.72 (d, 3H), 2.20 (s, 3H), 4.17 (q, 1H), 6.46 (d, 1H), 6.57 (d, 1H), 6.60 (s, 1H), 7.22-7.28 (m, 2H), 7.68 (d, 1H), 7.80 (d, 2H), 8.00 (d, 2H), 8.40 (s, 1H); APCI MS m/z 513 [C$_{27}$H$_{25}$F$_3$N$_2$O$_3$S-H]⁻. HPLC analysis (retention time=14.10 min) showed one peak, with a total purity of >99% (area percent).

Prepare Examples 61-65 by a similar method used to prepare Example 8 except starting from 2-(4-(trifluoromethylphenyl)-2H-indazole-6-carbaldehyde in step B as shown below:

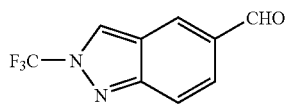

Example 61

2-Methyl-2-{2-methyl-4-[2-(4-trifluoromethylphenyl)-2H-indazol-5-ylmethoxy]phenoxy}propionic Acid

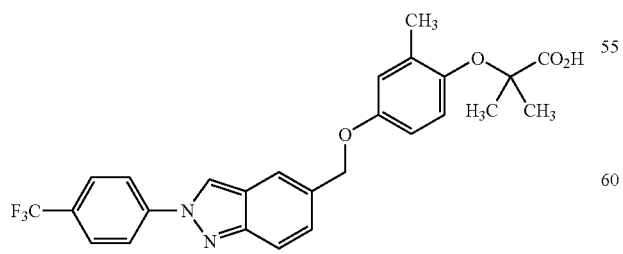

mp 164-166° C.; ¹H NMR (CDCl₃) δ 1.56 (s, 6H), 2.24 (s, 3H), 5.07 (s, 2H), 6.76 (d, 1H), 6.84 (d, 2H), 7.39 (d, 1H), 7.72-7.81 (m, 4H), 8.05 (d, 2H), 8.44 (s, 1H); APCI MS m/z 483 [C$_{26}$H$_{23}$F$_3$N$_2$O$_4$-H]⁻. HPLC analysis (retention time=12.66 min) showed one peak, with a total purity of >99% (area percent).

Example 62

2-Methyl-2-{4-[2-(4-trifluoromethylphenyl)-2H-indazol-5-ylmethoxy]phenylsulfanyl}propionic Acid

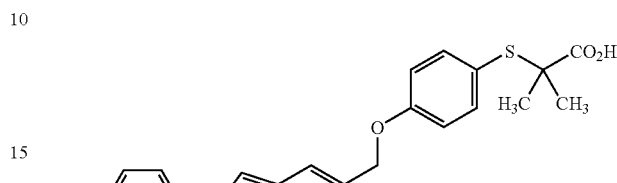

mp 192-194° C.; ¹H NMR (CDCl₃) δ 1.49 (s, 6H), 5.10 (s, 2H), 6.97 (d, 2H), 7.36 (dd, 1H) 7.46 (d, 2H), 7.69 (s, 1H), 7.76-7.80 (m, 3H), 8.02 (d, 2H), 8.41 (s, 1H); APCI MS m/z 485 [C$_{25}$H$_{21}$F$_3$N$_2$O$_3$S-H]⁻. HPLC analysis (retention time=12.18 min) showed one peak, with a total purity of 96.4% (area percent).

Example 63

2-Methyl-2-{4-[2-(4-trifluoromethylphenyl)-2H-indazol-5-ylmethylsulfanyl]phenoxy}propionic Acid

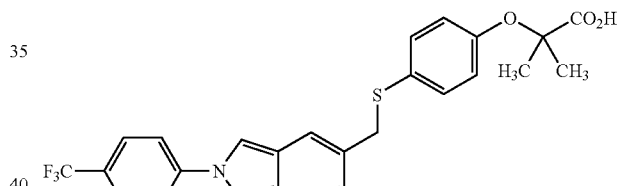

mp 159-161° C.; ¹H NMR (CDCl₃) δ 1.56 (s, 6H), 4.09 (s, 2H), 6.80 (d, 2H), 7.20-7.35 (m, 4H), 7.70 (d, 1H), 7.77 (d, 2H), 8.01 (d, 2H), 8.32 (s, 1H); APCI MS m/z 485 [C$_{25}$H$_{21}$F$_3$N$_2$O$_3$S-H]⁻. HPLC analysis (retention time=12.01 min) showed one peak, with a total purity of 97.7% (area percent).

Example 64

2-Methyl-2-{2-methyl-4-[2-(4-trifluoromethylphenyl)-2H-indazol-5-ylmethylsulfanyl]phenoxy}propionic Acid

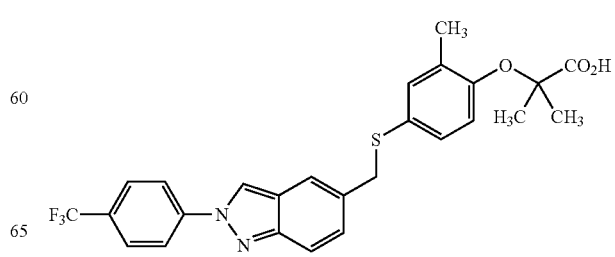

mp 143-145° C.; $^1$H NMR (CDCl$_3$) δ 1.59 (s, 6H), 2.16 (s, 3H), 4.08 (s, 2H), 6.68 (d, 1H), 7.03 (dd, 1H), 7.16 (d, 1H), 7.29 (dd, 1H), 7.37 (s, 1H), 7.70 (d, 1H), 7.76 (d, 2H), 8.00 (d, 2H), 8.32 (s, 1H); APCI MS m/z 501 [C$_{26}$H$_{23}$F$_3$N$_2$O$_3$S+H]$^+$. HPLC analysis (retention time=12.47 min) showed one peak, with a total purity of 98.9% (area percent).

Example 65

2-Methyl-2-{4-[2-(4-trifluoromethylphenyl)-2H-indazol-5-ylmethoxy]phenoxy}propionic Acid

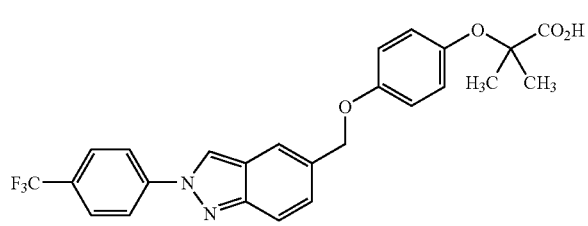

mp 203-205° C.; $^1$H NMR (DMSO-d$_6$) δ 1.44 (s, 6H), 5.11 (s, 2H), 6.83 (d, 2H), 6.96 (d, 2H), 7.41 (dd, 1H), 7.75 (d, 1H), 7.84 (s, 1H), 7.97 (d, 2H), 8.34 (d, 2H), 9.26 (s, 1H); APCI MS m/z 469 [C$_{25}$H$_{21}$F$_3$N$_2$O$_4$–H]$^-$. HPLC analysis (retention time=12.52 min) showed one peak, with a total purity of 98.5% (area percent).

Prepare Examples 66-70 by a similar method used to prepare Example 8 except starting from 2-(4-(trifluoromethylphenyl)-2H-indazole-5-carbaldehyde in step B as shown below:

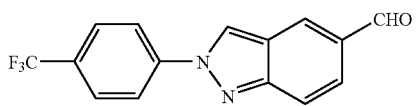

Example 66

(+/−)-2-Methyl-2-(2-methyl-4-{1-[2-(4-trifluoromethylphenyl)-2H-indazol-5-yl]ethoxy}phenoxy)propionic Acid

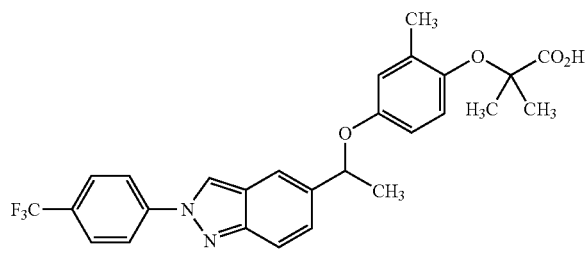

mp 129-131° C.; $^1$H NMR (CDCl$_3$) δ 1.50 (s, 6H), 1.66 (d, 3H), 2.16 (s, 3H), 5.29 (q, 1H), 6.59-6.63 (m, 1H), 6.69-6.76 (m, 2H), 7.36 (dd, 1H), 7.65 (s, 1H), 7.75-7.79 (m, 3H), 8.02 (d, 2H), 8.39 (s, 1H); APCI MS m/z 497 [C$_{27}$H$_{25}$F$_3$N$_2$O$_4$–H]$^-$. HPLC analysis (retention time=12.92 min) showed one peak, with a total purity of 98.2% (area percent).

Example 67

(+/−)-2-Methyl-2-(4-{1-[2-(4-trifluoromethylphenyl)-2H-indazol-5-yl]ethoxy}phenylsulfanyl)propionic Acid

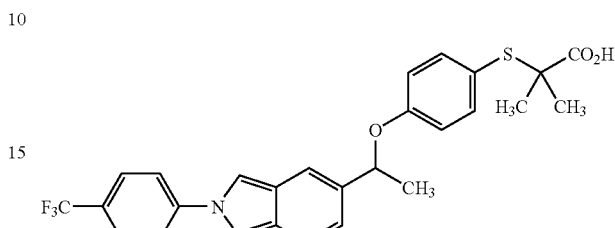

mp 153-155° C.; $^1$H NMR (CDCl$_3$) δ 1.42 (s, 3H), 1.44 (s, 3H), 1.68 (d, 3H), 5.35 (q, 1H), 6.85 (d, 2H), 7.31-7.35 (m, 3H), 7.63 (s, 1H), 7.74-7.78 (m, 3H), 8.01 (d, 2H), 8.38 (s, 1H); APCI MS m/z 499 [C$_{26}$H$_{23}$F$_3$N$_2$O$_3$S–H]$^-$. HPLC analysis (retention time=12.41 min) showed one peak, with a total purity of 97.2% (area percent).

Example 68

(+/−)-2-Methyl-2-(4-{1-[2-(4-trifluoromethylphenyl)-2H-indazol-5-yl]ethylsulfanyl}phenoxy)propionic Acid

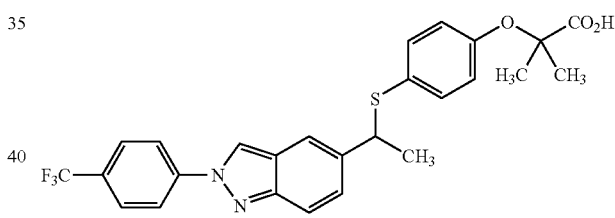

mp 109-111° C.; $^1$H NMR (CDCl$_3$) δ 1.54 (s, 6H), 1.67 (d, 3H), 4.28 (q, 1H), 6.74 (d, 2H), 7.17 (d, 2H), 7.29 (s, 1H), 7.37 (dd, 1H), 7.70 (d, 1H), 7.76 (d, 2H), 8.00 (d, 2H), 8.29 (s, 1H); APCI MS m/z 501 [C$_{26}$H$_{23}$F$_3$N$_2$O$_3$S+H]$^+$. HPLC analysis (retention time=12.33 min) showed one peak, with a total purity of 98.9% (area percent).

Example 69

(+/−)-2-Methyl-2-(2-methyl-4-{1-[2-(4-trifluoromethylphenyl)-2H-indazol-5-yl]ethylsulfanyl}phenoxy)propionic Acid

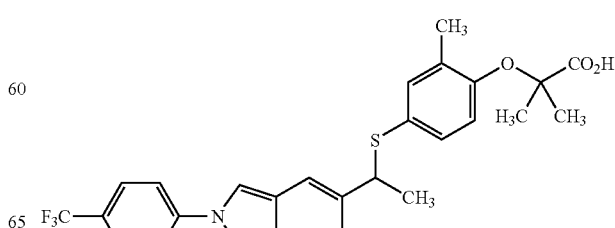

mp 70-72° C.; ¹H NMR (CDCl₃) δ 1.56 (s, 6H), 1.66 (d, 3H), 2.11 (s, 3H), 4.28 (q, 1H), 6.61 (d, 1H), 6.98 (dd, 1H), 7.12 (d, 1H), 7.31 (s, 1H), 7.38 (dd, 1H), 7.68-7.77 (m, 3H), 7.99 (d, 2H), 8.29 (s, 1H); APCI MS m/z 515 $[C_{27}H_{25}F_3N_2O_3S+H]^+$. HPLC analysis (retention time=13.01 min) showed one peak, with a total purity of 98.2% (area percent).

Example 70

(+/−)-2-Methyl-2-(4-{1-[2-(4-trifluoromethylphenyl)-2H-indazol-5-yl]ethoxy}phenoxy)propionic Acid

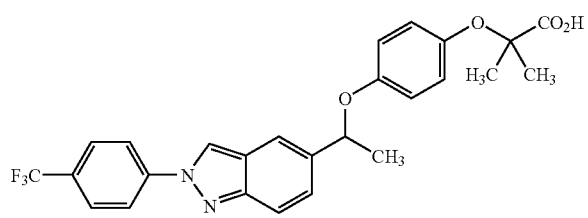

mp 152-154° C.; ¹H NMR (DMSO-d₆) δ 1.39 (s, 6H), 1.58 (d, 3H), 5.48 (q, 1H), 6.72 (d, 2H), 6.86 (d, 2H), 7.41 (dd, 1H), 7.72 (d, 1H), 7.76 (s, 1H), 7.96 (d, 2H), 8.31 (d, 2H), 9.19 (s, 1H); APCI MS m/z 483 $[C_{26}H_{23}F_3N_2O_4-H]^-$. HPLC analysis (retention time=11.72 min) showed one peak, with a total purity of 97.8% (area percent).

Prepare Example 71 by a similar method used to prepare Example 26.

Example 71

2-Methyl-2-{2-methyl-4-[2-(4-trifluoromethylphenyl)-2H-indazol-4-ylmethylsulfanyl]phenoxy}propionic Acid

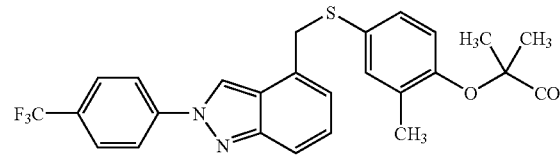

mp 125-127° C.; ¹H NMR (DMSO-d₆) δ 1.46 (s, 6H), 2.09 (s, 3H), 4.41 (s, 2H), 6.61 (d, 1H), 6.91 (d, 1H), 7.11 (dd, 1H), 7.20 (s, 1H), 7.22 (dd, 1H), 7.59 (d, 1H), 7.98 (d, 2H), 8.33 (d, 2H), 9.29 (s, 1H); APCI MS m/z 501 $[C_{26}H_{23}F_3N_2O_3S+H]^+$. HPLC analysis (retention time=12.64 min) showed one peak, with a total purity of 95.2% (area percent).

Prepare Examples 72-76 by a similar method used to prepare Example 8 but starting from 2-(4-(trifluoromethylphenyl)-2H-indazole-4-carbaldehyde in step B as shown below:

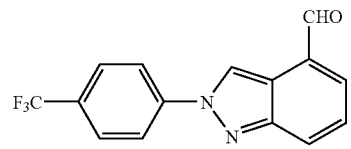

Example 72

(+/−)-2-Methyl-2-(2-methyl-4-{1-[2-(4-trifluoromethylphenyl)-2H-indazol-4-yl]ethylsulfanyl}phenoxy)propionic Acid

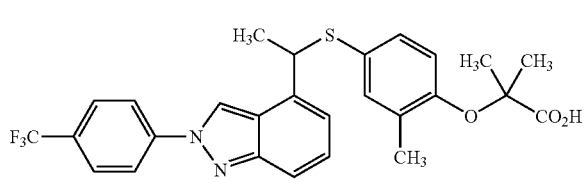

mp 153-155° C.; ¹H NMR (CDCl₃) δ 1.56 (s, 6H), 1.76 (d, 3H), 2.11 (s, 3H), 4.50 (q, 1H), 6.60 (d, 1H), 6.82 (d, 1H), 6.94 (dd, 1H), 7.05 (s, 1H), 7.17 (dd, 1H), 7.63 (s, 1H), 7.79 (d, 2H), 8.06 (d, 2H), 8.59 (s, 1H); APCI MS m/z 515 $[C_{27}H_{25}F_3N_2O_3S+H]^+$. HPLC analysis (retention time=13.10 min) showed one peak, with a total purity of 96.7% (area percent).

Example 73

(+/−)-2-Methyl-2-(4-{1-[2-(4-trifluoromethylphenyl)-2H-indazol-4-yl]ethylsulfanyl}phenoxy)propionic Acid

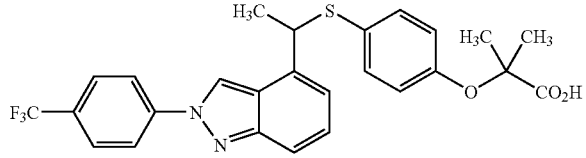

mp 148-150° C.; ¹H NMR (CDCl₃) δ 1.55 (s, 6H), 1.77 (d, 3H), 4.51 (q, 1H), 6.73 (d, 2H), 6.80 (d, 1H), 7.09-7.18 (m, 3H), 7.62 (d, 1H), 7.79 (d, 2H), 8.06 (d, 2H), 8.61 (s, 1H); APCI MS m/z 501 $[C_{26}H_{23}F_3N_2O_3S+H]^+$. HPLC analysis (retention time=12.45 min) showed one peak, with a total purity of 97.1% (area percent).

Example 74

(+/−)-2-Methyl-2-(2-methyl-4-{1-[2-(4-trifluoromethylphenyl)-2H-indazol-4-yl]ethoxy}phenoxy)propionic Acid

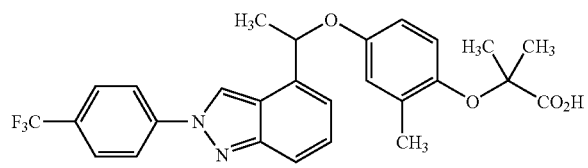

mp 130-132° C.; $^1$H NMR (CDCl$_3$) δ 1.49 (s, 6H), 1.76 (d, 3H), 2.14 (s, 3H), 5.47 (q, 1H), 6.60-6.70 (m, 2H), 6.77 (d, 1H), 7.08 (d, 1H), 7.28 (dd, 1H), 7.69 (d, 1H), 7.74 (d, 2H), 8.05 (d, 2H), 8.65 (s, 1H); APCI MS m/z 497 [C$_{27}$H$_{25}$F$_3$N$_2$O$_4$−H]$^-$. HPLC analysis (retention time=12.30 min) showed one peak, with a total purity of 96.9% (area percent).

Example 75

(+/−)-2-Methyl-2-(4-{1-[2-(4-trifluoromethylphenyl)-2H-indazol-4-yl]ethoxy}phenoxy)propionic Acid

mp 86-88° C.; $^1$H NMR (CDCl$_3$) δ 1.47 (s, 6H), 1.78 (d, 3H), 5.48 (q, 1H), 6.76-6.84 (m, 4H), 7.08 (d, 1H), 7.28 (dd, 1H), 7.69 (d, 1H), 7.78 (d, 2H), 8.04 (d, 2H), 8.65 (s, 1H); APCI MS m/z 485 [C$_{26}$H$_{23}$F$_3$N$_2$O$_4$+H]$^+$. HPLC analysis (retention time=11.80 min) showed one peak, with a total purity of 95.7% (area percent).

Example 76

(+/−)-2-Methyl-2-(4-{1-[2-(4-trifluoromethyl-phenyl)-2H-indazol-4-yl]ethoxy}phenylsulfanyl)propionic Acid

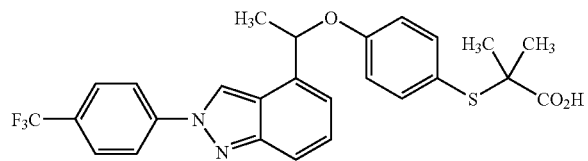

mp 138-140° C.; $^1$H NMR (CDCl$_3$) δ 1.40 (s, 3H), 1.42 (s, 3H) 1.77 (d, 3H), 5.54 (q, 1H), 6.86 (d, 2H), 7.08 (d, 1H), 7.24-7.33 (m, 3H), 7.68 (d, 1H), 7.76 (d, 2H), 8.01 (d, 2H), 8.59(s, 1H); APCI MS m/z 501 [C$_{26}$H$_{23}$F$_3$N$_2$O$_3$S+H]$^+$.

HPLC analysis (retention time=12.44 min) showed one peak, with a total purity of 95.1% (area percent).

Prepare Examples 77-81 by a similar method used to prepare Example 30.

Example 77

2-Methyl-2-{2-methyl-4-[1-(4-trifluoromethylphenyl)-1H-indazol-4-ylmethoxy]phenoxy}propionic Acid

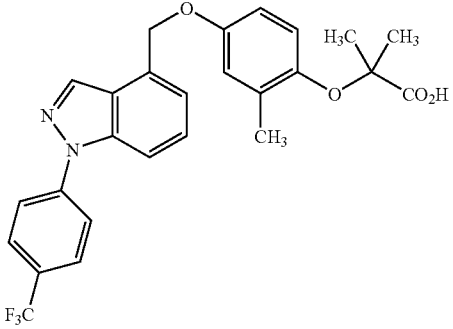

mp 100-104° C.; $^1$H NMR (CDCl$_3$) δ 8.3 (s, 1H), 7.85 (d, 2H, J=9 Hz), 7.79 (d, 2H, J=9 Hz), 7.7 (d, 1H, J=8 Hz), 7.4 (t, 1H, J=8 Hz), 7.2 (d, 1H, J=7 Hz), 6.82 (d, 1H, J=3 Hz), 6.7 (m, 2H), 5.3 (s, 2H), 2.2 (s, 3H), 1.5 (s, 6H); APCI mass spectrum m/z 483 [C$_{26}$H$_{23}$F$_3$N$_2$O$_4$−H]$^-$. HPLC analysis (retention time=12.5 min) showed one peak, with a total purity of 98.0% (area percent).

Example 78

2-Methyl-2-{2-methyl-4-[1-(4-trifluoromethylphenyl)-1H-indazol-4-ylmethylsufanyl]phenoxy}propionic Acid

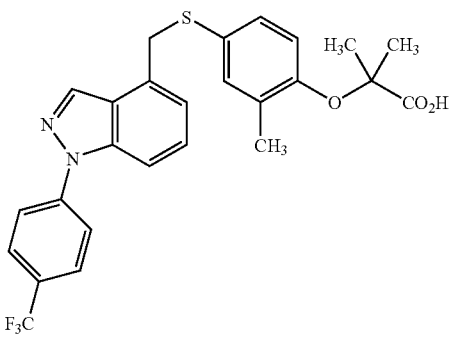

mp 62-66-° C.; $^1$H NMR (CDCl$_3$) δ 8.0 (s, 1H), 7.88 (d, 2H, J=9 Hz), 7.79 (d, 2H, J=9 Hz), 7.63 (d, 1H, J=8 Hz), 7.35 (t, 1H, J=8 Hz), 7.19 (d, 1H, J=2H), 7.04 (d, 1H, 7 Hz), 7.0 (dd, 1H, J=8 Hz, 2 Hz), 6.65 (d, 1H, J=8 Hz), 4.3 (s, 2H), 2.2 (s, 3H), 1.6 (s, 6H); APCI mass spectrum m/z 499

[C$_{26}$H$_{23}$F$_3$N$_2$O$_3$S−H]$^-$. HPLC analysis (retention time=13 min) showed one peak, with a total purity of 98.6% (area percent).

Example 79

2-Methyl-2-{4-[1-(4-trifluoromethylphenyl)-1H-indazol-4-ylmethylsulfanyl]phenoxy}propionic Acid

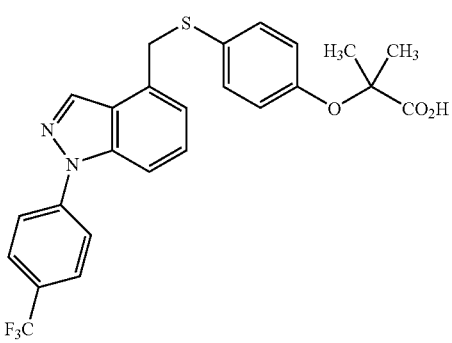

mp 158-160° C.; $^1$H NMR (CDCl$_3$+DMSO-d$_6$) δ 8.3 (s, 1H), 7.9 (d, 2H, J=9 Hz), 7.8 (d, 2H, J=9 Hz), 7.7 (d, 1H, 8 Hz), 7.48 (m, 1H), 7.33 (t, 1H, J=8 Hz), 7.2 (d, 2H, J=7 Hz), 7.0 (d, 1H, J=7 Hz), 6.8 (d, 2H, J=7 Hz), 4.3 (s, 2H), 1.5 (s, 6H); APCI mass spectrum m/z 485 [C$_{25}$H$_{21}$F$_3$N$_2$O$_3$S−H]$^-$. HPLC analysis (retention time=12.2 min) showed one peak, with a total purity of 96.6% (area percent).

Example 80

2-Methyl-2-{4-[1-(4-trifluoromethylphenyl)-1H-indazol-4-ylmethoxy]phenylsulfanyl}propionic Acid

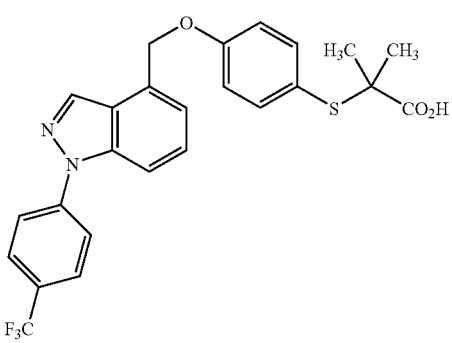

mp 168-170° C.; $^1$H NMR (CDCl$_3$+DMSO-d$_6$) δ 8.4 (s, 1H), 7.9 (d, 2H, J=8 Hz), 7.82 (d, 2H, J=8 Hz), 7.79 (d, 1H, J=7 Hz), 7.5 (m, 3H), 7.3 (d, 1H, J=7 Hz), 7.0 (d, 2H, J=7 Hz), 5.4 (s, 2H), 1.4 (s, 6H); APCI mass spectrum m/z 485 [C$_{25}$H$_{21}$F$_3$N$_2$O$_3$S−H]$^-$. HPLC analysis (retention time=14.3 min) showed one peak, with a total purity of >99% (area percent).

Example 81

2-Methyl-2-{4-[1-(4-trifluoromethylphenyl)-1H-indazol-4-ylmethoxy]phenoxy}propionic Acid

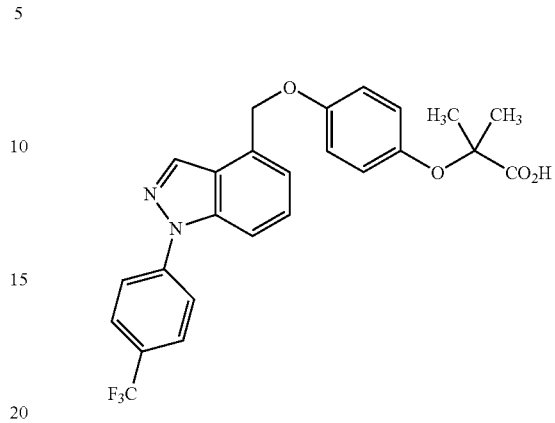

mp 128-130° C.; $^1$H NMR (CDCl$_3$) δ 8.4 (s, 1H), 7.9 (d, 2H, J=8 Hz), 7.8 (d, 2H, J=8 Hz), 7.75 (d, 1H, J=8 Hz), 7.5 (t, 1H, J=7 Hz), 7.3 (d, 1H, J=7 Hz), 6.9 (m, 4H), 5.4 (s, 2H), 1.5 (s, 6H); APCI mass spectrum m/z 469 [C$_{25}$H$_{21}$F$_3$N$_2$O$_4$−H]$^-$. HPLC analysis (retention time=11.9 min) showed one peak, with a total purity of >99% (area percent).

Prepare Examples 82-86 by a similar method used to prepare Example 8 except starting from 2-(4-(trifluoromethylphenyl)-1H-indazole-4-carbaldehyde in step B as shown below:

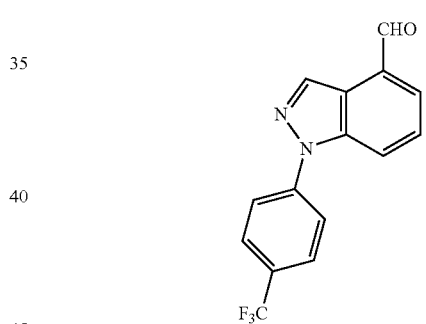

Example 82

(+/−)-2-Methyl-2-(2-methyl-4-{1-[1-(4-trifluoromethylphenyl)-1H-indazol-4-yl]ethoxy}phenoxy)propionic Acid

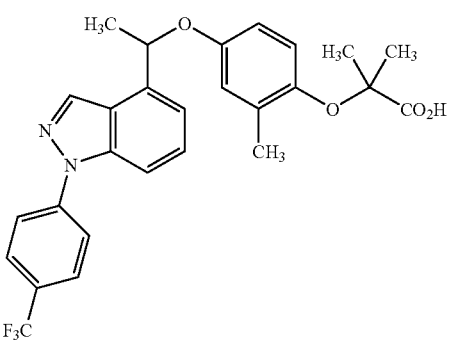

mp 82-85° C.; ¹H NMR (CDCl₃) δ 8.48 (s, 1H), 7.88 (d, 2H, J=9 Hz), 7.8 (d, 2H, J=9 Hz), 7.7 (d, 1H, 8 Hz), 7.4 (t, 1H, J=7 Hz), 7.25 (d, 1H, J=8 Hz), 6.8 (d, 1H, J=3 Hz), 6.7 (d, 1H, J=8 Hz), 6.6 (dd, 1H, J=8 Hz, 3 Hz), 5.6 (q, 1H, J=7 Hz), 2.2 (s, 3H), 1.7 (d, 3H, J=7 Hz), 1.5 (s, 6H); APCI mass spectrum m/z 498 [$C_{27}H_{25}F_3N_2O_4$]⁻. HPLC analysis (retention time=14.5 min) showed one peak, with a total purity of >99% (area percent).

Example 83

(+/−)-2-Methyl-2-(2-methyl-4-{1-[1-(4-trifluoromethylphenyl)-1H-indazol-4-yl]ethylsulfanyl}phenoxy)propionic Acid

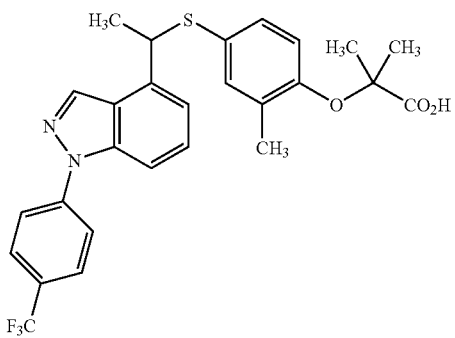

mp 85-87° C.; ¹H NMR (CDCl₃) δ 8.2 (s, 1H), 7.85 (d, 2H, J=8 Hz), 7.8 (d, 2H, J=8 Hz), 7.6 (d, 1H, 8 Hz), 7.35 (t, 1H, J=8 Hz), 7.13 (d, 1H, J=7 Hz), 7.07 (s, 1H), 6.92 (d, 1H, J=8 Hz), 6.5 (d, 1H, J=8 Hz), 5.6 (q, 1H, J=7 Hz), 2.05 (s, 3H), 1.8 (d, 3H, J=7 Hz), 1.5 (s, 6H); APCI mass spectrum m/z 514 [$C_{27}H_{25}F_3N_2O_3S$]⁻. HPLC analysis (retention time=15.5 min) showed one peak, with a total purity of 97.7% (area percent).

Example 84

(+/−)-2-Methyl-2-(4-{1-[1-(4-trifluoromethylphenyl)-1H-indazol-4-yl]ethoxy}phenylsulfanyl)propionic Acid

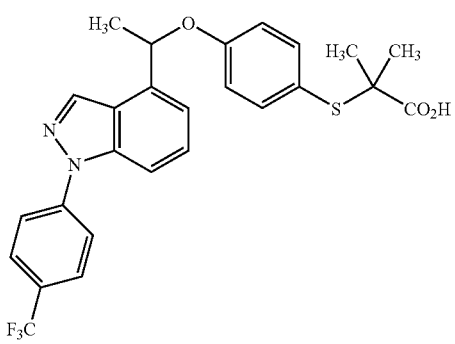

No clear melt observed; ¹H NMR (CDCl₃) δ 8.42 (s, 1H), 7.85 (d, 2H, J=9 Hz), 7.79 (d, 2H, J=9 Hz), 7.7 (d, 1H, J=9 Hz), 7.4 (t, 1H, J=9 Hz), 7.3 (d, 2H, J=9 Hz), 7.25 (m, 1H), 6.85 (d, 2H, J=9 Hz), 5.7 (q, 1H, J=7 Hz), 1.8 (d, 3H, J=7 Hz), 1.4 (s, 6H). APCI mass spectrum m/z 500 [$C_{26}H_{23}F_3N_2O_3S$]⁻. HPLC analysis (retention time=14.6 min) showed one peak, with a total purity of >99% (area percent).

Example 85

(+/−)-2-Methyl-2-(4-{1-[1-(4-trifluoromethylphenyl)-1H-indazol-4-yl]ethoxy}phenoxy)propionic Acid

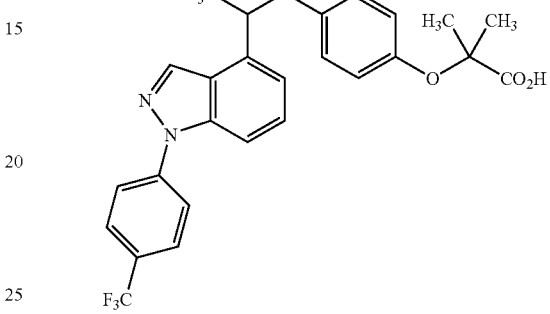

mp 99-102° C.; ¹H NMR (CDCl₃) δ 8.50 (s, 1H), 7.90 (d, J=9 Hz, 2H), 7.80 (d, J=9 Hz, 2H), 7.70 (d, J=8 Hz, 1H), 7.40 (t, J=8 Hz, 1H), 7.25 (m, 1H), 6.80 (m, 4H), 5.60 (q, J=6 Hz, 1H), 1.80 (d, J=6 Hz, 3H), 1.50 (s, 6H); APCI mass spectrum m/z 483 [$C_{26}H_{23}F_3N_2O_4$–H]⁻. HPLC analysis (retention time=14.2 min) showed one peak, with a total purity of 98.7% (area percent).

Example 86

(+/−)-2-Methyl-2-(4-{1-[1-(4-trifluoromethylphenyl)-1H-indazol-4-yl]ethylsulfanyl}phenoxy)propionic Acid

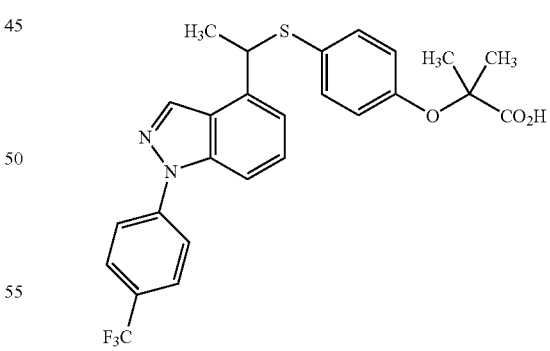

mp 85-90° C.; ¹H NMR (CDCl₃) δ 8.3 (s, 1H), 7.85 (d, J=9 Hz, 2H), 7.80 (d, J=9 Hz, 2H), 7.60 (d, J=9 Hz, 1H), 7.35 (t, J=7 Hz, 1H), 7.15 (d, J=9 Hz, 2H), 7.10 (d, J=7 Hz, 1H), 6.75 (d, J=9 Hz, 2H), 4.60 (q, J=7 Hz, 1H), 1.80 (d, J=7 Hz, 3H), 1.55 (s, 6H); APCI mass spectrum m/z 499 [$C_{26}H_{23}F_3N_2O_3S$–H]⁻. HPLC analysis (retention time=15.1 min) showed one peak, with a total purity of >99% (area percent).

Prepare examples 87-90 by a similar method used to prepare example 8 but starting from 2-(4-trifluoromethylphenyl)-1H-indazole-4-carbaldehyde as shown below and using 3,3,3-trifluoropropylmagnesium bromide in step B:

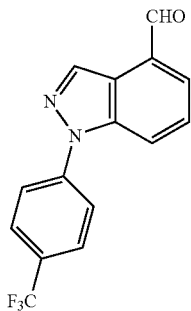

Example 87

(+/−)-2-Methyl-2-(2-methyl-4-{4,4,4-trifluoro-1-[1-(4-trifluoromethylphenyl)-1H-indazol-4-yl]butoxy}phenoxy)propionic Acid

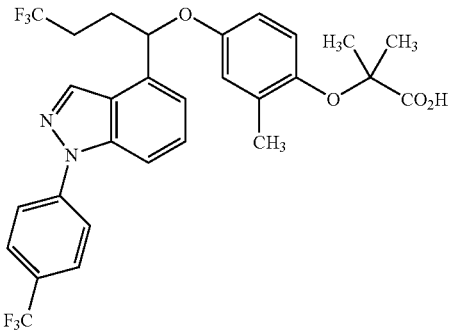

mp 218-222° C.; $^1$H NMR (CDCl$_3$+DMSO-d$_6$) δ 8.50 (s, 1H), 7.90 (d, J=9 Hz, 2H), 7.80 (d, J=9 Hz, 2H), 7.70 (m, 1H), 7.50 (t, J=7 Hz, 1H), 7.30 (d, J=7 Hz, 1H), 6.70 (m, 2H), 6.50 (dd, J=7, 3 Hz, 1H), 5.50 (m, 1H), 2.50-2.10 (m, 4H), 2.05 (s, 3H), 1.40 (s, 6H); APCI mass spectrum m/z 580 [C$_{29}$H$_{26}$F$_6$N$_2$O$_4$]$^-$. HPLC analysis (retention time=15.7 min) showed one peak, with a total purity of 98.3% (area percent).

Example 88
(+/−)-2-Methyl-2-(2-methyl-4-{4,4,4-trifluoro-1-[1-(4-trifluoromethylphenyl)-1H-indazol-4-yl]butylsulfanyl}phenoxy)propionic Acid

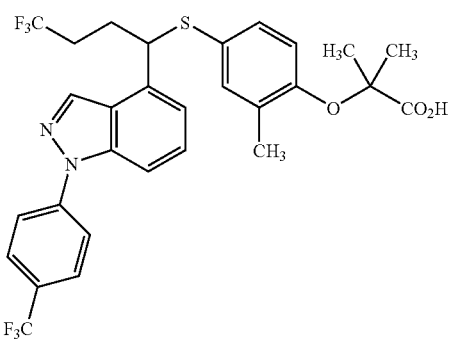

mp 205-210° C.; $^1$H NMR (CDCl$_3$+DMSO-d$_6$) δ 8.30 (s, 1H), 7.90 (d, J=9 Hz, 2H), 7.80 (d, J=9 Hz, 2H), 7.70 (m, 1H), 7.40 (t, J=8 Hz, 1H), 7.00 (d, J=7 Hz, 1H), 6.90 (s, 1H), 6.85 (d, J=9 Hz, 1H), 6.80 (d, J=9 Hz, 1H), 4.50 (t, 1H), 2.40-2.10 (m, 4H), 2.00 (s, 3H), 1.50 (s, 3H), 1.45 (s, 3H); APCI mass spectrum m/z 596 [C$_{29}$H$_{26}$F$_6$N$_2$O$_3$S]$^-$. HPLC analysis (retention time=16.6 min) showed one peak, with a total purity of 99.0% (area percent).

Example 89

(+/−)-2-Methyl-2-(4-{4,4,4-trifluoro-1-[1-(4-trifluoromethylphenyl)-1H-indazol-4-yl]butoxy}phenylsulfanyl)propionic Acid

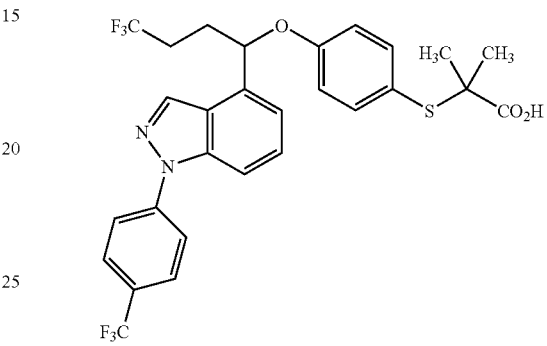

mp>260° C.; $^1$H NMR (CDCl$_3$+DMSO-d$_6$) δ 8.50 (s, 1H), 7.90 (d, J=8 Hz, 2H), 7.80 (d, J=8 Hz, 2H), 7.75 (m, 1H), 7.45 (t, J=7 Hz, 1H), 7.30 (m, 3H), 6.80 (d, J=9 Hz, 2H), 5.65 (m, 1H), 2.50-2.10 (m, 4H), 1.25 (s, 6H); APCI mass spectrum m/z 581 [C$_{28}$H$_{24}$F$_6$N$_2$O$_3$S−H]$^-$. HPLC analysis (retention time=16.1 min) showed one peak, with a total purity of >99% (area percent).

Example 90

(+/−)-2-Methyl-2-(4-{4,4,4-trifluoro-1-[1-(4-trifluoromethylphenyl)-1H-indazol-4-yl]butoxy}phenoxy)propionic Acid

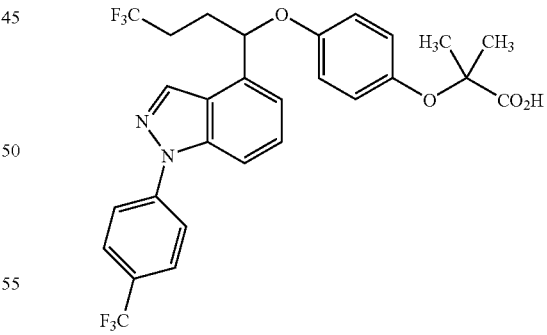

mp 175-180° C.; $^1$H NMR (CDCl$_3$+DMSO-d$_6$) δ 8.50 (s, 1H), 8.00 (m, 3H), 7.80 (m, 3H), 7.50 (t, J=9 Hz, 1H), 7.30 (d, J=7 Hz, 1H), 6.20 (m, 4H), 5.60 (m, 1H), 2.50-2.10 (m, 4H), 1.40 (s, 6H); APCI mass spectrum m/z 565 [C$_{28}$H$_{24}$F$_6$N$_2$O$_4$—H]$^-$. HPLC analysis (retention time=10.5 min) showed one peak, with a total purity of 98.3% (area percent).

Prepare examples 91-95 by a similar method used to prepare example 8 but starting from 2-(4-trifluoromethylphenyl)-1H-indazole-4-carbaldehyde as shown below and using phenylmagnesium bromide in step B:

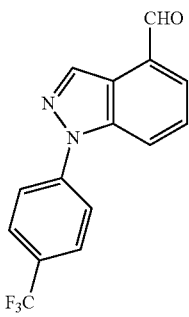

Example 91

(+/−)-2-Methyl-2-(2-methyl-4-{phenyl-[1-(4-trifluoromethylphenyl)-1H-indazol-4-yl]methoxy}phenoxy)propionic Acid

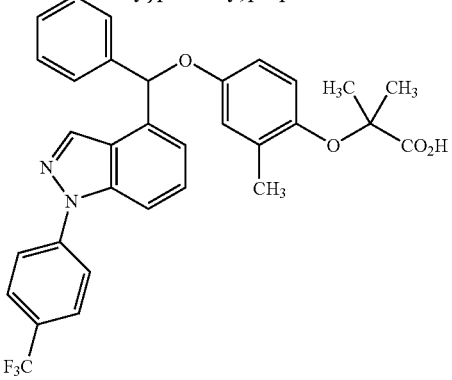

mp 140-145° C.; $^1$H NMR (CDCl$_3$) δ 8.35 (s, 1H), 7.85 (d, J=9 Hz, 2H), 7.80 (d, J=9 Hz, 2H), 7.70 (d, J=8 Hz, 1H), 7.50-7.20 (m, 7H), 6.80 (s, 1H), 6.60 (m, 2H), 6.50 (s, 1H), 2.05 (s, 3H), 1.40 (s, 6H); APCI mass spectrum m/z 559 [C$_{32}$H$_{27}$F$_3$N$_2$O$_4$−H]$^−$. HPLC analysis (retention time=16.3 min) showed one peak, with a total purity of >99% (area percent).

Example 92

(+/−)-2-Methyl-2-(2-methyl-4-{phenyl-[1-(4-trifluoromethylphenyl)-1H-indazol-4-yl]methylsulfanyl}phenoxy)propionic Acid

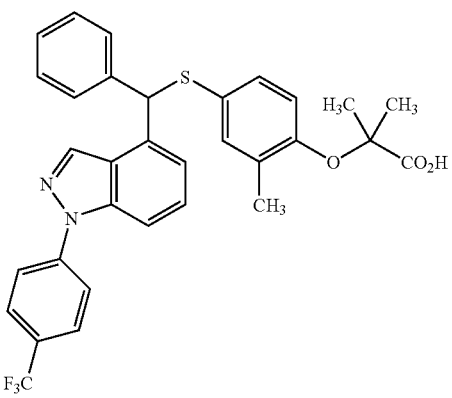

mp 181-186° C.; $^1$H NMR (CDCl$_3$+DMSO-d$_6$) δ 8.40 (s, 1H), 7.95 (d, J=8 Hz, 2H), 7.85 (d, J=8 Hz, 2H), 7.75 (m, 1H), 7.50-7.40 (m, 4H), 7.30-7.20 (m, 3H), 7.10 (s, 1H), 6.95 (dd, J=8, 2 Hz, 1H), 6.70 (d, J=9 Hz, 1H), 5.95 (s, 1H), 2.05 (s, 3H), 1.40 (s, 6H); APCI mass spectrum m/z 575 [C$_{32}$H$_{27}$F$_3$N$_2$O$_3$S−H]$^−$. HPLC analysis (retention time=16.5 min) showed one peak, with a total purity of >99% (area percent).

Example 93

(+/−)-2-Methyl-2-(4-{phenyl-[1-(4-trifluoromethylphenyl)-1H-indazol-4-yl]methoxy}phenylsulfanyl) propionic Acid

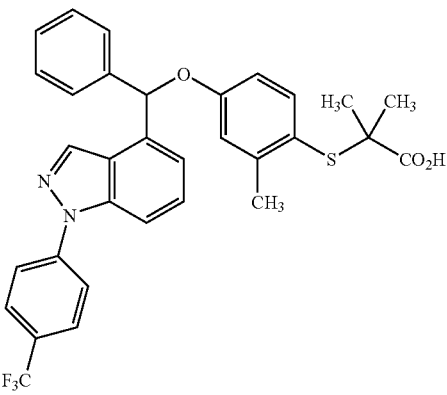

$^1$H NMR (CDCl$_3$+DMSO-d$_6$) δ 8.45 (s, 1H), 7.70 (d, J=8 Hz, 2H), 7.80 (m, 3H), 7.55 (d, J=7 Hz, 2H), 7.30 (t, J=9 Hz, 1H), 7.40-7.20 (m, 6H), 7.00 (d, J=9 Hz, 2H), 6.70 (s, 1H), 1.30 (s, 6H); APCI mass spectrum m/z 561 [C$_{31}$H$_{25}$F$_3$N$_2$O$_3$S−H]$^−$. HPLC analysis (retention time=15.8 min) showed one peak, with a total purity of >99% (area percent).

Example 94

(+/−)-2-Methyl-2-(4-{phenyl-[1-(4-trifluoromethylphenyl)-1H-indazol-4-yl]methylsulfanyl}phenoxy) propionic Acid

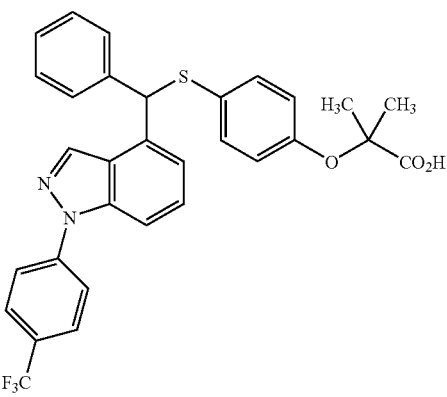

$^1$H NMR (CDCl$_3$) δ 8.15 (s, 1H), 7.80 (d, J=9 Hz, 2H), 7.75 (d, J=9 Hz, 2H), 7.65 (d, 1H), 7.50-7.20 (m, 7H), 7.10 (d, J=8

Hz, 2H), 6.65 (d, J=8 Hz, 2H), 5.80 (s, 1H), 1.40 (s, 6H); APCI mass spectrum m/z 561 [$C_{31}H_{25}F_3N_2O_3S-H$]$^-$. HPLC analysis (retention time=16.0 min) showed one peak, with a total purity of >99% (area percent).

Example 95

(+/−)-2-Methyl-2-(4-{phenyl-[1-(4-trifluoromethylphenyl)-1H-indazol-4-yl]methoxy}phenoxy)propionic Acid

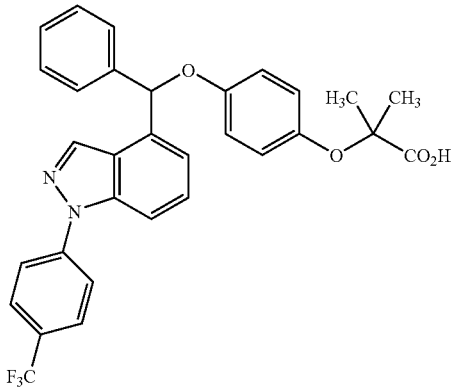

$^1$H NMR (CDCl$_3$+DMSO-d$_6$) δ 8.40 (s, 1H), 7.70 (d, J=9 Hz, 2H), 7.80 (d, J=9 Hz, 2H), 7.75 (m, 2H), 7.55 (d, J=7 Hz, 2H), 7.45 (t, J=8 Hz, 1H), 7.40-7.20 (m, 4H), 6.90 (d, J=9 Hz, 2H), 6.80 (d, J=9 Hz, 2H), 6.60 (s, 1H), 1.50 (s, 6H); APCI mass spectrum m/z 545 [$C_{31}H_{25}F_3N_2O_4-H$]$^-$. HPLC analysis (retention time=14.9 min) showed one peak, with a total purity of >99% (area percent).

Prepare examples 96-100 by a similar method used to prepare example 33.

Example 96

2-Methyl-2-{2-methyl-4-[1-(4-trifluoromethylphenyl)-1H-indazol-7-ylmethoxy]phenoxy}propionic Acid

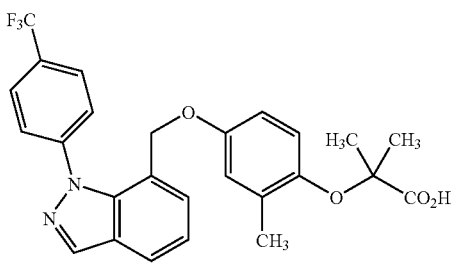

mp 124-126° C.; $^1$H NMR (CDCl$_3$+DMSO-d$_6$) δ 8.20 (s, 1H), 7.85 (d, J=8 Hz, 1H), 7.60 (d, J=9 Hz, 2H), 7.55 (d, J=9 Hz, 2H), 7.45 (m, 1H), 7.25 (t, J=8 Hz, 1I), 6.70 (d, J=9 Hz, 1H), 6.30 (m, 2H), 4.70 (s, 2H), 2.10 (s, 3H), 1.50 (s, 6H); APCI mass spectrum m/z 483 [$C_{26}H_{23}F_3N_2O_4-H$]$^-$. HPLC analysis (retention time=13.3 min) showed one peak, with a total purity of 99.0% (area percent).

Example 97

2-Methyl-2-{4-[1-(4-trifluoromethylphenyl)-1H-indazol-7-ylmethoxy]phenylsulfanyl}propionic Acid

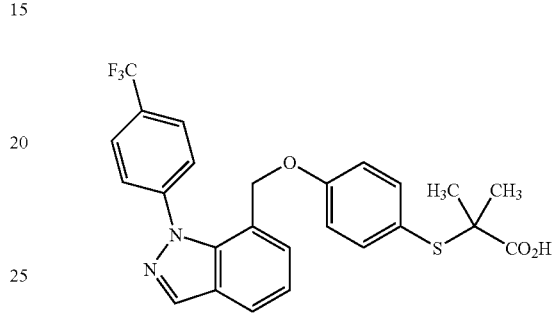

mp 214-216° C.; $^1$H NMR (CDCl$_3$+DMSO-d$_6$) δ 8.30 (s, 1H), 7.90 (d, J=7 Hz, 1H), 7.65 (d, J=8 Hz, 2H), 7.50 (m, 3H), 7.30 (m, 3H), 6.50 (d, J=8 Hz, 2H), 4.85 (s, 2H), 1.30 (s, 6H); APCI mass spectrum m/z 485 [$C_{25}H_{21}F_3N_2O_3S-H$]$^-$. HPLC analysis (retention time=13.3 min) showed one peak, with a total purity of 98.9% (area percent).

Example 98

2-Methyl-2-{2-methyl-4-[1-(4-trifluoromethylphenyl)-1H-indazol-7-ylmethylsulfanyl]phenoxy}propionic Acid

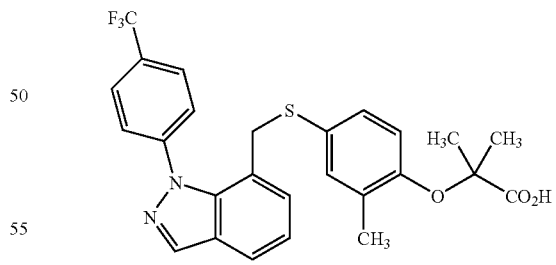

mp 154-158° C.; $^1$H NMR (CDCl$_3$) δ 8.20 (s, 1H), 7.65 (m, 5H), 7.10 (m, 2H), 6.70 (s, 1H), 6.55 (d, J=9 Hz, 1H), 6.45 (d, J=9 Hz, 1H), 3.80 (s, 2H), 2.00 (s, 3H), 1.50 (s, 6H); APCI mass spectrum m/z 499 [$C_{26}H_{23}F_3N_2O_3S-H$]$^-$. HPLC analysis (retention time=14.0 min) showed one peak, with a total purity of 98.2% (area percent).

Example 99

2-Methyl-2-{4-[1-(4-trifluoromethylphenyl)-1H-indazol-7-ylmethylsulfanyl]phenoxy}propionic Acid

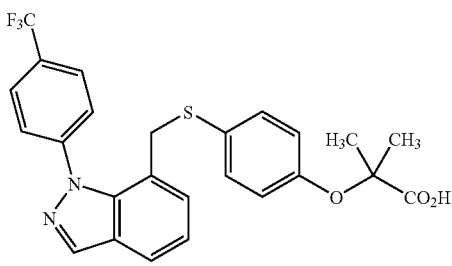

mp 125-128° C.; $^1$H NMR (CDCl$_3$) δ 8.25 (s, 1H), 7.70 (m, 5H), 7.10 (m, 2H), 6.85 (d, J=8 Hz, 2H), 6.70 (d, J=8 Hz, 2H), 3.90 (s, 2H), 1.60 (s, 6H); APCI mass spectrum m/z 485 [C$_{25}$H$_{21}$F$_3$N$_2$O$_3$S−H]$^−$. HPLC analysis (retention time=13.4 min) showed one peak, with a total purity of 98.9% (area percent).

Example 100

2-Methyl-1-2-{4-[1-(4-trifluoromethylphenyl)-1H-indazol-7-ylmethoxy]phenoxy}propionic Acid

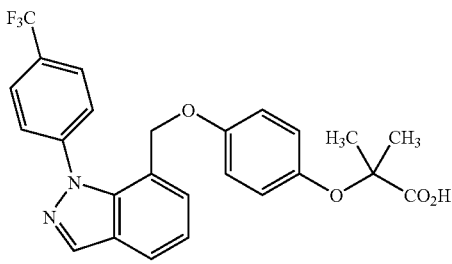

mp 146-149° C.; $^1$H NMR (CDCl$_3$) δ 8.25 (s, 1H), 7.80 (d, J=8 Hz, 1H), 7.60 (d, J=8 Hz, 2H), 7.50 (d, J=8 Hz, 2H), 7.45 (d, J=7 Hz, 1H), 7.20 (t, J=8 Hz, 1H), 6.70 (d, J=9 Hz, 2H), 6.40 (d, J=9 Hz, 2H), 4.70 (s, 2H), 1.40 (s, 6H); APCI mass spectrum m/z 469 [C$_{25}$H$_{21}$F$_3$N$_2$O$_4$−H]$^−$. HPLC analysis (retention time=12.7 min) showed one peak, with a total purity of >99% (area percent).

Biological Assays

Binding and Cotransfection Studies

The in vitro potency of compounds in modulating PPARα receptors are determined by the procedures detailed below. DNA-dependent binding (ABCD binding) is carried out using SPA technology with PPAR receptors. Tritium-labeled PPARα agonists are used as radioligands for generating displacement curves and IC$_{50}$ values with compounds of the invention. Cotransfection assays are carried out in CV-1 cells. The reporter plasmid contained an acylCoA oxidase (AOX) PPRE and TK promoter upstream of the luciferase reporter cDNA. Appropriate PPARs are constitutively expressed using plasmids containing the CMV promoter. For PPARα, interference by endogenous PPARγ in CV-1 cells is an issue. In order to eliminate such interference, a GAL4 chimeric system is used in which the DNA binding domain of the transfected PPAR is replaced by that of GAL4, and the GAL4 response element is utilized in place of the AOX PPRE. Cotransfection efficacy is determined relative to PPARα agonist reference molecules. Efficacies are determined by computer fit to a concentration-response curve, or in some cases at a single high concentration of agonist (10 μM).

These studies are carried out to evaluate the ability of compounds of the invention to bind to and/or activate various nuclear transcription factors, particularly huPPARα ("hu" indicates "human"). These studies provide in vitro data concerning efficacy and selectivity of compounds of the invention. Furthermore, binding and cotransfection data for compounds of the invention are compared with corresponding data for marketed compounds that act on huPPARα.

The binding and cotransfection efficacy values for compounds of the invention which are especially useful for modulating a PPAR receptor, are ≦100 nM and ≧50%, respectively.

Evaluation of Triglyceride Reduction and HDL Cholesterol Elevation in HuapoAI Transgenic Mice Compounds of the present invention are studied for effects upon HDL and triglyceride levels in human apoAI mice. For each compound tested, seven to eight week old male mice, transgenic for human apoAI (C57BL/6-tgn(apoa1)1rub, Jackson Laboratory, Bar Harbor, Me.) are acclimated in individual cages for two weeks with standard chow diet (Purina 5001) and water provided ad libitum. After the acclimation, mice and chow are weighed and assigned to test groups (n=5) with randomization by body weight. Mice are dosed daily by oral gavage for 8 days using a 29 gauge, 1½ inch curved feeding needle (Popper & Sons). The vehicle for the controls, test compounds and the positive control (fenofibrate 100 mg/kg) is 1% carboxymethylcellulose (w/v) with 0.25% tween 80 (w/v). All mice are dosed daily between 6 and 8 a.m. with a dosing. volume of 0.2 ml. Prior to termination, animals and diets are weighed and body weight change and food consumption are calculated. Three hours after last dose, mice are euthanized with CO2 and blood is removed (0.5-1.0 ml) by cardiac puncture. After sacrifice, the liver, heart, and epididymal fat pad are excised and weighed. Blood is permitted to clot and serum is separated from the blood by centrifugation.

Cholesterol and triglycerides are measured calorimetrically using commercially prepared reagents (for example, as available from Sigma #339-1000 and Roche #450061 for triglycerides and cholesterol, respectively). The procedures are modified from published work (McGowan M. W. et al., Clin Chem 29:538-542,1983; Allain C. C. et al., Clin Chem 20:470-475,1974. Commercially available standards for triglycerides and total cholesterol, respectively, commercial quality control plasma, and samples are measured in duplicate using 200 μl of reagent. An additional aliquot of sample, added to a well containing 200 μl water, provided a blank for each specimen. Plates are incubated at room temperature on a plate shaker and absorbance is read at 500 nm and 540 nm for total cholesterol and triglycerides, respectively. Values for the positive control are always within the expected range and the coefficient of variation for samples is below 10%. All samples from an experiment are assayed at the same time to minimize inter-assay variability.

Serum lipoproteins are separated and cholesterol quantitated by fast protein liquid chromatography (FPLC) coupled to an in line detection system. Samples are applied to a Superose 6HR size exclusion column (Amersham Pharmacia Biotech) and eluted with phosphate buffered saline-EDTA at 0.5 mL/min. Cholesterol reagent (Roche Diagnostics Chol/HP 704036) at 0.16 ml/min mixed with the column effluent through a T-connection and the mixture passed through a 15 m×0.5 mm id knitted tubing reactor immersed in a 37 C water bath. The colored product produced in the presence of cholesterol is monitored in the flow stream at 505 nm and the analog voltage from the monitor is converted to a digital signal for collection and analysis. The change in voltage corresponding to change in cholesterol concentration is plotted vs time and the area under the curve corresponding to the elution of very low density lipoprotein (VLDL), low density lipoprotein (LDL) and high density lipoprotein (HDL) is calculated using Perkin Elmer Turbochrome software.

Triglyceride Serum Levels in Mice Dosed with a Compound of the Invention is Compared to Mice Receiving the Vehicle to identify compounds which could be particularly useful for lowering triglycerides. Generally, triglyceride decreases of greater than or equal to 30% (thirty percent) compared to control following a 30 mg/kg dose suggests a compound that can be especially useful for lowering triglyceride levels.

The percent increase of HDLc serum levels in mice receiving a compound of the invention is compared to mice receiving vehicle to identify compounds of the invention that could be particularly useful for elevating HDL levels. Generally, and increase of greater than or equal to 25% (twenty five percent) increase in HDLc level following a 30 mg/kg dose suggests a compound that can be especially useful for elevating HDLc levels.

It may be particularly desirable to select compounds of this invention that both lower triglyceride levels and increase HDLc levels. However, compounds that either lower triglyceride levels or increase HDLc levels may be desirable as well.

Evaluation of Glucose Levels in db/db Mice

The effects upon plasma glucose associated with administering various dose levels of different compounds of the present invention and the PPAR gamma agonist rosiglitazone (BRL49653) or the PPAR alpha agonist fenofibrate, and the control, to male db/db mice, are studied.

Five week old male diabetic (db/db) mice [for example, $C_{57}BlKs/j$-m +/+ Lepr(db), Jackson Laboratory, Bar Harbor, Me.] or lean littermates are housed 6 per cage with food and water available at all times. After an acclimation period of 2 weeks, animals are individually identified by ear notches, weighed, and bled via the tail vein for determination of initial glucose levels. Blood is collected (100 µl) from unfasted animals by wrapping each mouse in a towel, cutting the tip of the tail with a scalpel, and milking blood from the tail into a heparinized capillary tube. Sample is discharged into a heparinized microtainer with gel separator and retained on ice. Plasma is obtained after centrifugation at 4° C. and glucose measured immediately. Remaining plasma is frozen until the completion of the experiment, when glucose and triglycerides are assayed in all samples. Animals are grouped based on initial glucose levels and body weights. Beginning the following morning, mice are dosed daily by oral gavage for 7 days. Treatments are test compounds (30 mg/kg), a positive control agent (30 mg/kg) or vehicle [1% carboxymethylcellulose (w/v)/0.25% Tween80 (w/v); 0.3 ml/mouse]. On day 7, mice are weighed and bled (tail vein) 3 hours after dosing. Twenty-four hours after the $7^{th}$ dose (i.e., day 8), animals are bled again (tail vein). Samples obtained from conscious animals on days 0, 7 and 8 are assayed for glucose. After the 24-hour bleed, animals are weighed and dosed for the final time. Three hours after dosing on day 8, animals are anesthetized by inhalation of isoflurane and blood obtained via cardiac puncture (0.5-0.7 ml). Whole blood is transferred to serum separator tubes, chilled on ice and permitted to clot. Serum is obtained after centrifugation at 4° C. and frozen until analysis for compound levels. After sacrifice by cervical dislocation, the liver, heart and epididymal fat pads are excised and weighed.

Glucose is measured calorimetrically using commercially purchased reagents. According to the manufacturers, the procedures are modified from published work (McGowan, M. W., Artiss, J. D., Strandbergh, D. R. & Zak, B. Clin Chem, 20:470-5 (1974) and Keston, A. Specific calorimetric enzymatic analytical reagents for glucose. Abstract of papers 129th Meeting ACS, 31C (1956).); and depend on the release of a mole of hydrogen peroxide for each mole of analyte, coupled with a color reaction first described by Trinder (Trinder, P. Determination of glucose in blood using glucose oxidase with an alternative oxygen acceptor. Ann Clin Biochem, 6:24 (1969)). The absorbance of the dye produced is linearly related to the analyte in the sample. The assays are further modified in our laboratory for use in a 96 well format. The commercially available standard for glucose, commercially available quality control plasma, and samples (2 or 5 µl/well) are measured in duplicate using 200 µl of reagent. An additional aliquot of sample, pipetted to a third well and diluted in 200 µl water, provided a blank for each specimen. Plates are incubated at room temperature for 18 minutes for glucose on a plate shaker (DPC Micormix 5) and absorbance read at 500 nm on a plate reader. Sample absorbances are compared to a standard curve (100-800 for glucose). Values for the quality control sample are always within the expected range and the coefficient of variation for samples is below 10%. All samples from an experiment are assayed at the same time to minimize inter-assay variability.

Evaluation of the Effects of Compounds of the Present Invention upon $A^y$ Mice Body Weight, Fat Mass, Glucose and Insulin Levels Female $A^y$ Mice Female $A^y$ mice are singly housed, maintained under standardized conditions (22° C., 12 h light:dark cycle), and provided free access to food and water throughout the duration of the study. At twenty weeks of age the mice are randomly assigned to vehicle control and treated groups based on body weight and body fat content as assessed by DEXA scanning (N=6). Mice are then dosed via oral gavage with either vehicle or a Compound of this invention (50 mg/kg) one hour after the initiation of the light cycle (for example, about 7 A.M.) for 18 days. Body weights are measured daily throughout the study. On day 14 mice are maintained in individual metabolic chambers for indirect calorimetry assessment of energy expenditure and fuel utilization. On day 18 mice are again subjected to DEXA scanning for post treatment measurement of body composition.

The results of p.o. dosing of compound for 18 days on body weight, fat mass, and lean mass are evaluated and suggest which compounds of this invention can be especially useful for maintaining desirable weight and/or promoting desired lean to fat mass.

Indirect calorimetry measurements revealing a significant reduction in respiratory quotient (RQ) in treated animals during the dark cycle [0.864±0.013 (Control) vs. 0.803±0.007 (Treated); p<0.001] is indicative of an increased utilization of fat during the animals' active (dark) cycle and can be used to selected especially desired compounds of this invention. Additionally, treated animals displaying significantly higher rates of energy expenditure than control animals suggest such compounds of this invention can be especially desired.

Male KK/A$^y$ Mice

Male KK/A$^y$ mice are singly housed, maintained under standardized conditions (22° C., 12 h light:dark cycle), and provided free access to food and water throughout the duration of the study. At twenty-two weeks of age the mice are randomly assigned to vehicle control and treated groups based on plasma glucose levels. Mice are then dosed via oral gavage with either vehicle or a Compound of this invention (30 mg/kg) one hour after the initiation of the light cycle (7 A.M.) for 14 days. Plasma glucose, triglyceride, and insulin levels are assessed on day 14.

The results of p.o. dosing of compound for 14 days on plasma glucose, triglycerides, and insulin are evaluated to identify compounds of this invention which may be especially desired.

Method to Elucidate the LDL-cholesterol Total-cholesterol and Triglyceride Lowering Effect Male Syrian hamsters (Harlan Sprague Dawley) weighing 80-120 g are placed on a high-fat cholesterol-rich diet for two to three weeks prior to use. Feed and water are provided ad libitum throughout the course of the experiment. Under these conditions, hamsters become hypercholesterolemic showing plasma cholesterol levels between 180-280 mg/dl. (Hamsters fed with normal chow have a total plasma cholesterol level between 100-150 mg/dl.) Hamsters with high plasma cholesterol (180 mg/dl and above) are randomized into treatment groups based on their total cholesterol level using the GroupOptimize V211.xls program.

A Compound of this invention is dissolved in an aqueous vehicle (containing CMC with Tween 80) such that each hamster received once a day approx. 1 ml of the solution by gavage at doses 3 and 30 mg/kg body weight. Fenofibrate (Sigma Chemical, prepared as a suspension in the same vehicle) is given as a known alpha-agonist control at a dose of 200 mg/kg, and the blank control is vehicle alone. Dosing is performed daily in the early morning for 14 days.

Quantification of Plasma Lipids

On the last day of the test, hamsters are bled (400 ul) from the suborbital sinus while under isoflurane anesthesia 2 h after dosing. Blood samples are collected into heparinized microfuge tubes chilled in ice bath. Plasma samples are separated from the blood cells by brief centrifugation. Total cholesterol and triglycerides are determined by means of enzymatic assays carried out automatically in the Monarch equipment (Instrumentation Laboratory) following the manufacturer's procedure. Plasma lipoproteins (VLDL, LDL and HDL) are resolved by injecting 25 ul of the pooled plasma samples into an FPLC system eluted with phosphate buffered saline at 0.5 ml/min through a Superose 6HR 10/30 column (Pharmacia) maintained room temp. Detection and characterization of the isolated plasma lipids are accomplished by postcolumn incubation of the effluent with a Cholesterol/HP reagent (for example, Roche Lab System; infused at 0.12 min) in a knitted reaction coil maintained at 37° C. The intensity of the color formed is proportional to the cholesterol concentration and is measured photometrically at 505 nm.

The effect of administration of a Compound of this invention for 14 days is studied for the percent reduction in LDL level with reference to the vehicle group. Especially desired compounds are markedly more potent than fenofibrate in LDL-lowering efficacy. Compounds of this invention that decrease LDL greater than or equal to 30% (thirty percent) compared to vehicle can be especially desired.

The total-cholesterol and triglyceride lowering effects of a Compound of this invention is also studied. The data for reduction in total cholesterol and triglyceride levels after treatment with a compound of this invention for 14 days is compared to the vehicle to suggest compounds that can be particularly desired. The known control fenofibrate did not show significant efficacy under the same experimental conditions.

Method to Elucidate the Fibrinogen-Lowering Effect of PPAR Modulators

Zucker Fatty Rat Model:

The life phase of the study on fibrinogen-lowering effect of compounds of this invention is part of the life phase procedures for the antidiabetic studies of the same compounds. On the last (14$^{th}$) day of the treatment period, with the animals placed under surgical anesthesia, ~3 ml of blood is collected, by cardiac puncture, into a syringe containing citrate buffer. The blood sample is chilled and centrifuged at 4° C. to isolate the plasma that is stored at −70° C. prior to fibrinogen assay.

Quantification of Rat Plasma Fibrinogen

Rat plasma fibrinogen levels are quantified by using a commercial assay system consists of a coagulation instrument following the manufacturer's protocol. In essence, 100 ul of plasma is sampled from each specimen and a 1/20 dilution is prepared with buffer. The diluted plasma is incubated at 37° C. for 240 seconds. Fifty microliters of clotting reagent thrombin solution (provided by the instrument's manufacturer in a standard concentration) is then added. The instrument monitors the clotting time, a function of fibrinogen concentration quantified with reference to standard samples. Compounds that lower fibrinogen level greater than vehicle can be especially desired.

Cholesterol and triglyceride lowering effects of compounds of this invention are also studied in Zucker rats.

Method to Elucidate the Anti-body Weight Gain and Anti-appetite Effects of Compounds of this Invention Fourteen-Day Study in Zucker Fatty Rat[1] or ZDF Rat[2] Models Male Zucker Fatty rats, non-diabetic (Charles River Laboratories, Wilmington, Mass.) or male ZDF rats (Genetic Models, Inc, Indianapolis, Ind.) of comparable age and weight are acclimated for 1 week prior to treatment. Rats are on normal chow and water is provided ad libitum throughout the course of the experiment.

Compounds of this invention are dissolved in an aqueous vehicle such that each rat received once a day approximately 1 ml of the solution by gavage at doses 0.1, 0.3, 1 and 3 mg/kg body weight. Fenofibrate (Sigma Chemical, prepared as a suspension in the same vehicle) a known alpha-agonist given at doses of 300 mg/kg, as well as the vehicle are controls. Dosing is performed daily in the early morning for 14 days. Over the course of the experiment, body weight and food consumption are monitored. Using this assay, compounds of this invention are identified to determine which can be associated with a significant weight reduction.

Method to Elucidate the Activation of the PPAR Delta Receptor In Vivo

This method is particularly useful for measuring the in vivo PPAR delta receptor activation of compounds of this invention that are determined to possess significant in vitro activity for that receptor isoform over the PPAR gamma isoform.

Male PPARa null mice (129s4 SvJae-PPARa<tm1Gonz>mice; Jackson Laboratories) of 8-9 weeks of age are maintained on Purina 5001 chow with water ad libitum for at least one week prior to use. Feed and water are provided ad libitum throughout the course of the experiment. Using the GroupOptimizeV211.xls program, mice are randomized into treatment groups of five animals each based on their body weight.

Compounds of this invention are suspended in an aqueous vehicle of 1% (w/v) carboxymethylcellulose and 0.25% Tween 80 such that each mouse receives once a day approx. 0.2 ml of the solution by gavage at doses ranging from 0.2 to 20 mg/kg body weight. A control group of mice is included in each experiment whereby they are dosed in parallel with vehicle alone. Dosing is performed daily in the early morning for 7 days.

On the last day of dosing, mice are euthanized by CO2 asphyxiation 3 hours after the final dose. Blood samples are collected by heart draw into EDTA-containing microfuge tubes and chilled on ice. Liver samples are collected by necropsy and are flash-frozen in liquid nitrogen and stored at −80 degrees Celsius. For RNA isolation from liver, five to ten mg of frozen liver is placed in 700 µl of 1× Nucleic Acid Lysis Solution (Applied Biosystems Inc., Foster City, Calif.) and homogenized using a hand-held tissue macerator (Biospec Products Inc., Bartlesville, Okla.). The homogenate is filtered through an ABI Tissue pre-filter (Applied Biosystems Inc., Foster City, Calif.) and collected in a deep well plate on an ABI 6100 Nucleic Acid prep station (Applied Biosystems Inc., Foster City, Calif.). The filtered homogenate is then loaded onto an RNA isolation plate and the RNA Tissue-Filter-DNA method is run on the ABI 6100. The isolated RNA is eluted in 150 µl of RNase free water. For quality assessment, 9 µl of the isolated RNA solution is loaded onto a 1% TBE agarose gel, and the RNA is visualized by ethidium bromide fluorescence.

Complementary DNA (cDNA) is synthesized using the ABI High Capacity Archive Kit (Applied Biosystems Inc., Foster City, CA). Briefly, a 2× reverse transcriptase Master Mix is prepared according to the manufacturer's protocol for the appropriate number of samples (RT Buffer, dNTP, Random Primers, MultiScribe RT (50 U/µl), RNase free water). For each reaction, 50 µl of 2× RT Master Mix is added to 50 µl of isolated RNA in a PCR tube that is incubated in a thermocycler (25° C. for 10 minutes followed by 37° C. for 2 hours). The resultant cDNA preparation is diluted 1:100 in dH2O for analysis by real-time PCR. Also, a standard curve of cDNA is diluted 1:20, 1:100, 1:400, 1:2000, 1:10,000 for use in final quantitation.

A real-time PCR Master Mix for mouse Cyp4A1 gene expression is mixed to contain:

1× Taqman Universal PCR Master Mix (Applied Biosystems Inc., Foster City, Calif.)
6 micromolar final concentration Forward primer; Qiagen/Operon Technologies, Alameda, Calif.)
6 micromolar final concentration Reverse primer (Qiagen/Operon Technologies, Alameda, Calif.)
0.15 micromolar final concentration Probe (5' 6-FAM and 3' Tamra-Q; Qiagen/Operon Technologies, Alameda, Calif.)
RNase free water to 10 microliters A real-time PCR Master Mix for the 18S ribosomal RNA control gene expression is mixed to contain 1× Taqman Universal PCR Master Mix (Applied Biosystems Inc., Foster City, Calif.)
0.34 micromolar Probe/Primer TaqMan® Ribosomal RNA Control Reagents #4308329 Applied Biosystems Inc., Foster City, Calif.)
RNase free water to 10 microliters For the real-time PCR analysis, 6 ul of the respective Master Mix solution (either Cyp4A1 or 18S) and 4 ul either of diluted cDNA or of Standard Curve samples is added to individual wells of a 384-well plate (n=2 for Standards; n=4 for unknowns). Reactions are performed using the ABI 7900HT standard universal RT-PCR cycling protocol. Data are analyzed using SDS 2.1 (Applied Biosystems Inc., Foster City, Calif.). Average quantity and standard deviation are calculated automatically for each individual sample, according to the standard curve values. Using Microsoft Excel 2000, mean values for each group of five individual mice is calculated. The mean value of each compound-treated group is divided by the mean value of the vehicle-treated group. The fold induction over the vehicle group is determined by assigning the vehicle group to the value of 1.0, and the fold change of the mean value for each group is expressed as fold-induction versus vehicle (1.0). Data are plotted using Jandel SigmaPlot 8.0.

Monkey Studies

Efficacy Studies

Compounds of the invention may be examined in a dyslipidemic rhesus monkey model. After an oral dose-escalation study for 28 days in obese, non-diabetic rhesus monkeys a determination of HDL-c elevation is made with each dose and compared with pretreatment levels. LDL cholesterol is also determined with each dose. C-reactive protein levels are measured and compared to pretreatment levels.

Compound of Formula 1 may be shown to elevate plasma HDL-cholesterol levels in an African Green Monkey model in a manner similar to that described above in rhesus monkeys.

Two groups of monkeys are placed in a dose-escalating study that consists of one week of baseline measurements, 9 weeks of treatments (vehicle, Compound of Formula I), and four weeks of washout. During baseline, monkeys in all three groups are administered vehicle once daily for seven days. Test compound of Formula I, is administered in vehicle once daily for three weeks, then at a greater concentration (double the dose may be desired) once daily for three weeks, and then a still greater concentration (double the most recent dose may be desired) once daily for three weeks. At the completion of treatment, monkeys in both groups are administered vehicle once daily and monitored for an additional six weeks.

Animals are fasted overnight and then sedated for body weight measurements and blood collection at weeks 1 (vehicle), 2, 3, 4, 6, 7, 9, 10, 12, and 14 of the study.

Parameters to Measured, for Example:
Body weight
Total plasma cholesterol
HDL
LDL
Triglycerides
Insulin
Glucose PK parameters at week 4, 7, and 10 (plasma drug concentration at last week of each dose)
ApoAI
ApoAII
ApoB
ApoCIII
Liver enzymes (SGPT, SGOT, □GT)
Complete blood count Additionally, other measures may be made, as appropriate, and consistent with the stated study design.

EQUIVALENTS:

While this invention has been particularly shown and described with references to preferred embodiments thereof, it will be understood by those skilled in the art that various changes in form and details may be made therein without departing from the scope of the invention encompassed by the appended claims.

What is claimed is:
1. A compound of the structural Formula II:

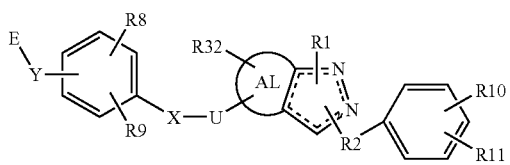

and stereoisomers, pharmaceutically acceptable salts thereof, wherein:
(a) R1 is hydrogen or $C_1$-$C_8$ alkyl;
(b) R31 is selected from the group consisting of hydrogen, hydroxy, cyano, nitro, halo, oxo, $C_1$-$C_6$ alkyl, $C_1$-$C_6$ alkyl-COOR12, $C_1$-$C_6$ alkoxy, $C_1$-$C_6$haloalkyl, $C_1$-$C_6$ haloalkyloxy, $C_3$-$C_7$ cycloalkyl, aryloxy, aryl-$C_{0-4}$-alkyl, heteroaryl, heterocycloalkyl, C(O)R13, COOR14, OC(O)R15, OS(O)$_2$R16, N(R17)$_2$, NR18C(O)R19, NR20SO$_2$R21, SR22, S(O)R23, S(O)$_2$R24, and S(O)2N(R25)2; R12, R13, R14, R15, R16, R17, R18, R19, R20, R21, R22, R23, R24 and R25 are each independently selected from the group consisting of hydrogen, $C_1$-$C_6$ alkyl and aryl;
(c) R2 is a bond;
(d) X is selected from the group consisting of a single bond, O and S;
(e) U is $C_1$-$C_3$ alkyl, and wherein such alkyl is substituted with from one to four substituents each independently selected from R30;
(f) Y is selected from the group consisting of C, O and S;
(g) E is C(R3)(R4)A and wherein
 (i) A is carboxyl;
 (iii) R3 is selected from the group consisting of hydrogen, $C_1$-$C_5$ alkyl, and $C_1$-$C_5$ alkoxy; and
 (iv) R4 is selected from the group consisting of H, $C_1$-$C_5$ alkyl, $C_1$-$C_5$ alkoxy, aryloxy, $C_3$-$C_6$ cycloalkyl, and aryl $C_0$-$C_4$ alkyl, and R3 and R4 are optionally combined to form a $C_3$-$C_4$ cycloalkyl, and wherein alkyl, alkoxy, aryloxy, cycloalkyl and aryl-alkyl are each optionally substituted with one to three substituents each independently selected from R26;
(h) R8 is selected from the group consisting of hydrogen, $C_1$-$C_4$ alkyl, and $C_1$-$C_4$ alkylenyl;
(i) R9 is selected from the group consisting of hydrogen and $C_1$-$C_4$ alkyl; R8 and R9 optionally combine to form a five membered fused bicyclic with the phenyl to which R8 and R9 attach, provided that when R8 and R9 form a fused ring, the group E-Y— is bonded at any available position on the five membered ring of such R8 and R9 fused bicyclic;
(j) R10, is $CF_3$;
(k) R11 is hydrogen;
(l) R30 is selected from the group consisting of $C_1$-$C_6$ alkyl, aryl-$C_{0-4}$-alkyl, aryl-$C_{1-4}$-heteroalkyl, heteroaryl-$C_{0-4}$-alkyl, and $C_3$-$C_6$ cycloalkylaryl-$C_{0-2}$-alkyl, and wherein $C_1$-$C_6$ alkyl, aryl-$C_{0-4}$-alkyl, aryl-$C_{1-4}$-heteroakyl, heteroaryl-$C_{0-4}$-alkyl, and $C_3$-$C_6$ cycloalkylaryl-$C_{0-2}$-alkyl are each optionally substituted with from one to three substituents each independently selected from R31;
(m) R32 is selected from the group consisting of hydrogen, halo, $C_1$-$C_6$ alkyl, $C_1$-$C_6$ haloalkyl, and $C_1$-$C_6$ alkyloxo;
(n) AL is a fused phenyl; and
(o) - - - is each optionally a bond to form a double bond at the indicated position.

2. A compound as claimed by claim 1 wherein X is —O—.
3. A compound as claimed by claim 1 wherein X is —S—.
4. A compound as claimed by claim 2 wherein Y is O.
5. A compound as claimed by claim 2 wherein Y is C.
6. A compound as claimed by claim 2 wherein Y is S.
7. A compound as claimed by claim 2 wherein - - - is a bond to form a double bond at the designated location on Formula II.
8. A compound as claimed by claim 7 wherein A is COOH.
9. A compound as claimed by claim 7, wherein R8 and R9 are each independently selected from the group consisting of hydrogen and $C_1$-$C_3$ alkyl.
10. A compound as claimed by claim 7 wherein R8 is $C_1$-$C_4$ alkylenyl.
11. A compound as claimed by claim 9 wherein R8 and R9 combine to form a fused bicyclic.
12. A compound as claimed by claim 9 wherein R1, R3, and R4 are each independently selected from the group consisting of hydrogen and $C_1$-$C_2$ alkyl.
13. A compound as claimed by claim 1 wherein U is substituted with $C_1$-$C_3$ alkyl.
14. A compound as claimed by claim 1 wherein U is substituted with from one to four substituents each independently selected from the group consisting of R30.
15. A compound as claimed by claim 1 wherein X is S, Y is selected from the group consisting of C and O, and E is CH2COOH.
16. A compound as claimed by claim 9 wherein R32 is hydrogen, R8 is hydrogen and R9 is $C_1$-$C_4$ alkyl.
17. A compound as claimed by claim 1 wherein the compound is selected from the group consisting of
2-Methyl-4-[2-(4-trifluoromethylphenyl)-2H-indazol-7-ylmethylsulfanyl]phenoxyacetic Acid;
3-{2-Methyl-4-[2-(4-trifluoromethylphenyl)-2H-indazol-7-ylmethylsulfanyl]phenyl}propionic Acid;
2-Ethyl-4-[2-(4-trifluoromethylphenyl)-2H-indazol-7-yl-methylsulfanyl]phenoxyacetic Acid;
3-[2-(4-Trifluoromethylphenyl)-2H-indazol-7-ylmethyl-sulfanyl]phenylacetic Acid;
6-[2-(4-Trifluoromethylphenyl)-2H-indazol-7-ylmethyl-sulfanyl]benzo[b]thiophen-3-ylacetic Acid;
3-{2-Methyl-4-[2-(4-trifluoromethylphenyl)-2H-indazol-7-ylmethoxy]phenyl}propionic Acid;
3-{2-Ethyl-4-[2-(4-trifluoromethylphenyl)-2H-indazol-7-ylmethoxy]phenyl}propionic Acid;

(+/−)-2-Methyl-4-{1-[2-(4-trifluoromethylphenyl)-2H-indazol-7-yl]ethylsulfanyl}phenoxyacetic Acid;
(+/−)-2-Methyl-4-{1-[2-(4-trifluoromethylphenyl)-2H-indazol-7-yl]ethylsulfanyl}phenoxyacetic Acid;
(+/−)-3-(2-Methyl-4-{1-[2-(4-trifluoromethylphenyl)-2H-indazol-7-yl]ethylsulfanyl}phenyl)propionic Acid;
(+/−)-2-Ethyl-4-{1-[2-(4-trifluoromethylphenyl)-2H-indazol-7-yl]ethylsulfanyl}phenoxyacetic Acid;
(+/−)-6-{1-[2-(4-Trifluoromethylphenyl)-2H-indazol-7yl]ethylsulfanyl}benzo[b]thiophen-3-ylacetic Acid;
(+/−)-3-(2-Methyl-4 {1-[2-(4-trifluoromethylphenyl)-2H-indazol-7yl]ethoxy}phenyl)propionic Acid;
(+/−)-3-(2-Ethyl-4-{1-[2-(4-trifuoromethylphenyl)-2H-indazol-7-yl]ethoxyphenyl)propionic Acid;
2-Methyl-4-{1-methyl-1-[2-(4-trifluoromethylphenyl)-2H-indazol-7-yl]ethylsulfanyl}phenoxyacetic Acid;
2-Methyl-4-{1-methyl-1-[2-(4-trifluoromethylphenyl)-2H-indazol-7-yl]ethylsulfanyl}phenoxyacetic Acid;
3-(2-Methyl-4-{1-methyl-1-[2-(4-trifluoromethylphenyl)-2H-indazol-7-yl]ethylsulfanyl}phenyl)propionic Acid;
2-Ethyl-4-{1-methyl-1-[2-(4-trifluoromethylphenyl) -2H-indazol-7-yl]ethylsulfanyl}phenoxyacetic Acid;
6-{1-Methyl-1-[2-(4-trifluoromethylphenyl)-2H -indazol-7-yl]ethylsulfanyl}benzo[b]thiophen-3-ylacetic Acid;
2-Methyl-4-[2-(4-trifluoromethylphenyl)-2H-indazol-6-ylmethylsulfanyl]phenoxyacetic Acid;
3-{2-Methyl-4-[2-(4-trifluoromethylphenyl)-2H -indazol-6-ylmethylsulfanyl]phenyl}propionic Acid;
2-Ethyl-4-[2-(4-trifluoromethylphenyl)-2H-indazol-6-ylmethylsulfanyl]phenoxyacetic Acid;
3-{2-Ethyl-4-[2-(4-trifluoromethylphenyl)-2H -indazol-6-ylmethoxy]phenyl}propionic Acid;
6-[2-(4-Trifluoromethylphenyl)-2H-indazol-6-ylmethylsulfanyl]benzo[b]thiophen-3-ylacetic Acid;
3-{2-Methyl-4-[2-(4-trifluoromethylphenyl)-2H -indazol-6-ylmethoxy]phenyl}propionic Acid;
{6-[2-(4-Trifluoromethylphenyl)-2H-indazol-6-ylmethoxy]benzo[b]thiophen-3-yl}acetic Acid;
2-Methyl-4-[2-(4-trifluoromethylphenyl)-2H-indazol-4-ylmethylsulfanyl]phenoxyacetic Acid;
2-Ethyl-4-[2-(4-trifluoromethylphenyl)-2H-indazol-4-yl-methylsulfanyl]phenoxyacetic Acid;
3-{2-Methyl-4-[2-(4-trifluoromethylphenyl)-2H -indazol-4-ylmethylsulfanyl]phenyl}propionic Acid;
6-[2-(4-Trifluoromethylphenyl)-2H-indazol-4-ylmethylsulfanyl]benzo[b]thiophen-3-ylacetic Acid;
2-Methyl-4-[1-(4-trifluoromethyiphenyl)-1H-indazol-4-ylmethylsulfanyl]phenoxyacetic Acid;
2-Ethyl-4-[1-(4-trifluoromethyiphenyl)-1H-indazol-4-yl-methylsulfanyl]phenoxyacetic Acid;
3-{2-Methyl-4-[1-(4-trifluoromethyiphenyl)-1H -indazol-4-ylmethylsulfanyl]phenyl}propionic Acid;
3-{2-Methyl-4-[1-(4-trifluoromethyiphenyl)-1H -indazol-7-ylmethylsulfanyl]phenyl}propionic Acid;
2-Methyl-4-[1-(4-trifluoromethyiphenyl)-1H-indazol-7-ylmethylsulfanyl]phenoxyacetic Acid;
2-Methyl-2-{2-methyl-4-[2-(4-trifluoromethylphenyl)-2H-indazol-7-ylmethylsulfanyl]phenoxy}propionic Acid;
2-Methyl-2-{4-[2-(4-trifluoromethylphenyl)-2H-indazol-7-ylmethylsulfanyl]phenoxy}propionic Acid;
2-Methyl-2-{2-methyl-4-[2-(4-trifluoromethylphenyl)-2H-indazol-7-ylmethoxy]phenoxy}propionic Acid;
2-Methyl-2-{4-[2-(4-trifluoromethylphenyl)-2H-indazol-7-ylmethoxy]phenylsulfanyl}propionic Acid;
2-Methyl-2-{4-[2-(4-trifluoromethylphenyl)-2H-indazol-7-ylmethoxy]phenoxy}propionic Acid;
(+/−)-2-Methyl-2-(2-methyl-4-{1-[2-(4-trifluoromethylphenyl)-2H-indazol-7-yl]ethoxy}phenoxy)propionic Acid;
(+/−)-2-Methyl-2-(2-methyl-4-{1-[2-(4-trifluoromethylphenyl)-2H-indazol-7-yl]ethylsulfanyl}phenoxy)propionic Acid;
(+/−)-2-Methyl-2-(4-{1-[2-(4-trifluoromethylphenyl)-2H-indazol-7-yl]ethylsulfanyl}phenoxy)propionic Acid;
(+/−)-2-Methyl-2-(4-{1-[2-(4-trifluoromethylphenyl)-2H-indazol-7-yl]ethoxy}phenylsulfanyl)propionic Acid;
(+/−)-2-Methyl-2-(4-{1-[2-(4-trifluoromethylphenyl)-2H-indazol-7-yl]ethoxy}phenoxy)propionic Acid;
(2-Ethyl-4-{2-[2-(4-trifluoromethylphenyl)-2H-indazol-7-yl]ethylsulfanyl}phenoxy)acetic Acid;
(2-Methyl-4-{2-[2-(4-trifluoromethylphenyl)-2H-indazol-7-yl]ethylsulfanyl}phenoxy)acetic Acid;
2-Methyl-2-(4-{2-[2-(4-trifluoromethylphenyl)-2H-indazol-7-yl]ethoxy}phenoxy)propionic Acid;
2-Methyl-2-(2-methyl-4-{2-[2-(4-trifluoromethylphenyl)-2H-indazol-7-yl]ethoxy}phenoxy)propionic Acid;
2-Methyl-2-(2-methyl-4-{2-[2-(4-trifluoromethylphenyl)-2H-indazol-7-yl]ethylsulfanyl}phenoxy)propionic Acid;
2-Methyl-2-(4-{2-[2-(4-trifluoromethylphenyl)-2H-indazol-7-yl]ethylsulfanyl}phenoxy)propionic Acid;
2-Methyl-2-{2-methyl-4-[2-(4-trifluoromethylphenyl)-2H-indazol-6-ylmethoxy]phenoxy}propionic Acid;
2-Methyl-2-{4-[2-(4-trifluoromethylphenyl)-2H-indazol-6-ylmethoxy]phenoxy}propionic Acid;
2-Methyl-2-{2-methyl-4-[2-(4-trifluoromethylphenyl)-2H-indazol-6-ylmethylsulfanyl]phenoxy}propionic Acid;
2-Methyl-2-{4-[2-(4-trifluoromethylphenyl)-2H-indazol-6-ylmethylsulfanyl]phenoxy}propionic Acid;
2-Methyl-2-{4-[2-(4-trifluoromethylphenyl)-2H-indazol-6-ylmethoxy]phenylsulfanyl}propionic Acid;
2-Methyl-2-{4-[2-(4-trifluoromethylphenyl)-2H-indazol-6-ylmethoxymethyl]phenoxy}propionic Acid;
(+/−)-2-Methyl-2-(2-methyl-4-{1-[2-(4-trifluoromethylphenyl)-2H-indazol-6-yl]ethoxy}phenoxy)propionic Acid;
(+/−)-2-Methyl-2-(4-{1-[2-(4-trifluoromethylphenyl)-2H-indazol-6-yl]ethoxy}phenoxy)propionic Acid;
(+/−)-2-Methyl-2-(4-{1-[2-(4-trifluoromethylphenyl)-2H-indazol-6yl]ethylsulfanyl}phenoxy)propionic Acid;
(+/−)-2-Methyl-2-(2-methyl-4-{1-[2-(4-trifluoromethylphenyl)-2H-indazol-6-yl]ethylsulfanyl}phenoxy)propionic Acid;
2-Methyl-2-{2-methyl-4-[2-(4-trifluoromethylphenyl)-2H-indazol-5-ylmethoxy]phenoxy}propionic Acid;
2-Methyl-2-{4-[2-(4-trifluoromethylphenyl)-2H-indazol-5-ylmethoxy]phenylsulfanyl}propionic Acid;
2-Methyl-2-{4-[2-(4-trifluoromethylphenyl)-2H-indazol-5-ylmethylsulfanyl]phenoxy}propionic Acid;
2-Methyl-2-{2-methyl-4-[2-(4-trifluoromethylphenyl)-2H-indazol-5-ylmethylsulfanyl]phenoxy}propionic Acid;
2-Methyl-2-{4-[2-(4-trifluoromethylphenyl)-2H-indazol-5-ylmethoxy]phenoxy}propionic Acid;
(+/−)-2-Methyl-2-(2-methyl-4-{1-[2-(4-trifluoromethylphenyl)-2H-indazol-5-yl]ethoxy}phenoxy)propionic Acid;

(+/−)-2-Methyl-2-(4-{1-[2-(4-trifluoromethylphenyl)-2H-indazol-5-yl]ethoxy}phenylsulfanyl)propionic Acid;

(+/−)-2-Methyl-2-(4-{1-[2-(4-trifluoromethylphenyl)-2H-indazol-5-yl]ethylsulfanyl}phenoxy)propionic Acid;

(+/−)-2-Methyl-2-(2-methyl-4-{1-[2-(4-trifluoromethylphenyl)-2H-indazol-5-yl]ethylsulfanyl}phenoxy)propionic Acid;

(+/−)-2-Methyl-2-(4-{1-[2-(4-trifluoromethylphenyl)-2H-indazol-5-yl]ethoxy}phenoxy)propionic Acid;

2-Methyl-2-{2-methyl-4-[2-(4-trifluoromethylphenyl)-2H-indazol-4-ylmethylsulfanyl]phenoxy}propionic Acid;

(+/−)-2-Methyl-2-(2-methyl-4-{1-[2-(4-trifluoromethylphenyl)-2H-indazol-4-yl]ethylsulfanyl}phenoxy)propionic Acid;

(+/−)-2-Methyl-2-(4-{1-[2-(4-trifluoromethylphenyl)-2H-indazol-4-yl]ethylsulfanyl}phenoxy)propionic Acid;

(+/−)-2-Methyl-2-(2-methyl-4-{1-[2-(4-trifluoromethylphenyl)-2H-indazol-4-yl]ethoxy}phenoxy)propionic Acid;

(+/−)-2-Methyl-2-(4-{1-[2-(4-trifluoromethylphenyl)-2H-indazol-4-yl]ethoxy}phenoxy)propionic Acid;

(+/−)-2-Methyl-2-(4-{1-[2-(4-trifluoromethyl-phenyl)-2H-indazol-4-yl]ethoxy}phenylsulfanyl)propionic Acid;

2-Methyl-2-{2-methyl-4-[1-(4-trifluoromethyiphenyl)-1H-indazol-4-ylmethoxy]phenoxy}propionic Acid;

2-Methyl-2-{2-methyl-4-[1-(4-trifluoromethyiphenyl)-1H-indazol-4-ylmethylsulfanyl]phenoxy}propionic Acid;

2-Methyl-2-{4-[1-(4-trifluoromethyiphenyl)-1H-indazol-4-ylmethylsulfanyl]phenoxy}propionic Acid;

2-Methyl-2-{4-[1-(4-trifluoromethyiphenyl)-1H-indazol-4-ylmethoxy]phenylsulfanyl}propionic Acid;

2-Methyl-2-{4-[1-(4-trifluoromethyiphenyl)-1H-indazol-4-ylmethoxy]phenoxy}propionic Acid;

(+/−)-2-Methyl-2-(2-methyl-4-{1-[1-(4-trifluoromethyiphenyl)-1H-indazol-4-yl]ethoxy}phenoxy)propionic Acid;

(+/−)-2-Methyl-2-(2-methyl-4-{1-[1-(4-trifluoromethyiphenyl)-1H-indazol-4-yl]ethylsulfanyl}phenoxy)propionic Acid;

(+/−)-2-Methyl-2-(4-{1-[1-(4-trifluoromethyiphenyl)-1H-indazol-4-yl]ethoxy}phenylsulfanyl)propionic Acid;

(+/−)-2-Methyl-2-(4-{1-[1-(4-trifluoromethyiphenyl)-1H-indazol-4-yl]ethoxy}phenoxy)propionic Acid;

(+/−)-2-Methyl-2-(4-{1-[1-(4-trifluoromethyiphenyl)-1H-indazol-4-yl]ethylsulfanyl}phenoxy)propionic Acid;

(+/−)-2-Methyl-2-(2-methyl-4-{4,4,4-trifluoro-1-[1-(4-trifluoromethyiphenyl)-1H-indazol-4-yl]butoxy}phenoxy)propionic Acid;

(+/−)-2-Methyl-2-(2-methyl-4-{4,4,4-trifluoro-1-[1-(4-trifluoromethyiphenyl)-1H-indazol-4-yl]butylsulfanyl}phenoxy)propionic Acid;

(+/−)-2-Methyl-2-(4-{4,4,4-trifluoro-1-[1-(4-trifluoromethyiphenyl)-1H-indazol-4-yl]butoxy}phenylsulfanyl)propionic Acid;

(+/−)-2-Methyl-2-(4-{4,4,4-trifluoro-1-[1-(4-trifluoromethyiphenyl)-1H-indazol-4-yl]butoxy}phenoxy)propionic Acid;

(+/−)-2-Methyl-2-(2-methyl-4-{phenyl-[1-(4-trifluoromethyiphenyl)-1H-indazol-4-yl]methoxy}phenoxy)propionic Acid;

(+/−)-2-Methyl-2-(2-methyl-4-{phenyl-[1-(4-trifluoromethyiphenyl)-1H-indazol-4-yl]methylsulfanyl}phenoxy)propionic Acid;

(+/−)-2-Methyl-2-(4-{phenyl-[1-(4-trifluoromethyiphenyl)-1H-indazol-4-yl]methoxy}phenylsulfanyl)propionic Acid;

(+/−)-2-Methyl-2-(4-{phenyl-[1-(4-trifluoromethyiphenyl)-1H-indazol-4-yl]methylsulfanyl}phenoxy)propionic Acid;

(+/−)-2-Methyl-2-(4-{phenyl-[1-(4-trifluoromethyiphenyl)-1H-indazol-4-yl]methoxy}phenoxy)propionic Acid;

2-Methyl-2-{2-methyl-4-[1-(4-trifluoromethyiphenyl)-1H-indazol-7-ylmethoxy]phenoxy}propionic Acid;

2-Methyl-2-{4-[1-(4-trifluoromethyiphenyl)-1H-indazol-7-ylmethoxy]phenylsulfanyl}propionic Acid;

2-Methyl-2-{2-methyl-4-[1-(4-trifluoromethyiphenyl)-1H-indazol-7-ylmethylsulfanyl]phenoxy}propionic Acid;

2-Methyl-2-{4-[1-(4-trifluoromethyiphenyl)-1H-indazol-7-ylmethylsulfanyl]phenoxy}propionic Acid; and, 2-Methyl-2-{4-[1-(4-trifluoromethyiphenyl)-1H-indazol-7-ylmethoxy]phenoxy}propionic Acid.

18. A pharmaceutical composition, comprising as an active ingredient, at least one compound as claimed by claim 1 together with a pharmaceutically acceptable carrier or diluent.

19. A method of treating diabetes mellitus in a mammal, comprising the step of administering to the mammal in need thereof a therapeutically effective amount of at least one compound of claim 1.

\* \* \* \* \*